(12) United States Patent
Cai et al.

(10) Patent No.: US 8,044,213 B2
(45) Date of Patent: Oct. 25, 2011

(54) THIAZOLYL-BENZIMIDAZOLES

(75) Inventors: Jianping Cai, West Caldwell, NJ (US); Shaoqing Chen, Bridgewater, NJ (US); Yi Chen, Nutley, NJ (US); Xin-Jie Chu, Livingston, NJ (US); Robert Alan Goodnow, Jr., Gillette, NJ (US); Kang Le, Green Brook, NJ (US); Kin-Chun Luk, North Caldwell, NJ (US); Steven Gregory Mischke, Florham Park, NJ (US); Peter Michael Wovkulich, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 48 days.

(21) Appl. No.: 12/634,771

(22) Filed: Dec. 10, 2009

(65) Prior Publication Data

US 2010/0160308 A1 Jun. 24, 2010

Related U.S. Application Data

(60) Provisional application No. 61/138,564, filed on Dec. 18, 2008.

(51) Int. Cl.
*A61K 31/427* (2006.01)
*C07D 417/04* (2006.01)
*C07D 417/14* (2006.01)

(52) U.S. Cl. ............ 548/181; 514/370; 514/233.8; 514/254.04; 514/322; 544/133; 544/367; 546/199

(58) Field of Classification Search .................. None
See application file for complete search history.

(56) References Cited

U.S. PATENT DOCUMENTS

| 4,322,429 A | 3/1982 | Burow |
| 4,818,270 A | 4/1989 | Grabiak et al. |
| 6,380,180 B1 | 4/2002 | Jensen et al. |
| 7,504,513 B2 | 3/2009 | Boylan et al. |
| 2004/0054186 A1 | 3/2004 | Das et al. |

FOREIGN PATENT DOCUMENTS

| EP | 1486490 | 12/2004 |
| WO | WO 02/12242 | 2/2002 |
| WO | WO 02/062804 | 8/2002 |
| WO | WO 03/070283 | 8/2003 |
| WO | WO 03/072062 | 9/2003 |
| WO | WO 03/093249 | 11/2003 |
| WO | WO 2004/011610 | 2/2004 |
| WO | WO 2004/014899 | 2/2004 |
| WO | WO 2004/043936 | 5/2004 |
| WO | WO 2004/046317 | 6/2004 |
| WO | WO 2004/067000 | 8/2004 |
| WO | WO 2004/074244 | 9/2004 |
| WO | WO 2004/087652 | 10/2004 |
| WO | 2004/113322 | 12/2004 |
| WO | WO 2005/019193 | 3/2005 |
| WO | WO 2005/042505 | 5/2005 |
| WO | WO 2005/042525 | 5/2005 |
| WO | WO 2005/075470 | 8/2005 |
| WO | 2007/030361 | 3/2007 |
| WO | WO 2007/096315 | 8/2007 |

OTHER PUBLICATIONS

Golub et al., Science, vol. 286, Oct. 15, 1999, pp. 531-537.*
Intenrational Search Report for PCT/EP2009/066579 dated Jan. 7, 2011.
Emmitte K et al, Bioorganic & Medicinal Chemistry Letters, 19:3 (2009) 1018-1021 XP025925874.
International Search Report in PCT/EP2009/066579 dated Nov. 10, 2010.

* cited by examiner

*Primary Examiner* — Laura L. Stockton
(74) *Attorney, Agent, or Firm* — George W. Johnston; Patricia S. Rocha-Tramaloni; David E. Wildman

(57) ABSTRACT

The invention is directed to compounds of formula (1)

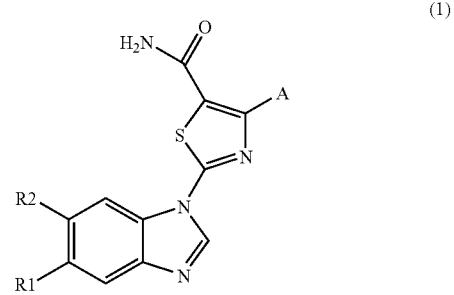

(1)

and pharmaceutically acceptable salts thereof, methods for the preparation thereof, and methods of use thereof.

15 Claims, No Drawings

THIAZOLYL-BENZIMIDAZOLES

PRIORITY TO RELATED APPLICATIONS

This application claims the benefit of U.S. Provisional Application No. 61/138,564, filed Dec. 18, 2008, which is hereby incorporated by reference in its entirety.

BACKGROUND OF THE INVENTION

The present invention is concerned with thiazolyl-benzimidazole derivatives and their pharmaceutically acceptable salts, the manufacture of the aforesaid and their use as therapeutic agents.

PLK1 is a member of the Polo-like kinase family. Polo-like kinases are highly conserved from yeast to humans and play a variety of roles in the G2/M phase transition and in the passage through mitotic phase of the cell cycle. Four Polo-like kinases, PLK1, PLK2 (Snk), PLK3 (Fnk), and PLK4 have been identified in humans. These proteins share extensive homologies across their kinase domains, in C-terminal "Polo" boxes. Using neutralizing antibodies, anti-sense oligos, and dominant-negative protein, PLK1 was shown to be essential for mitosis in vitro cultured cells. Furthermore, down regulation of PLK1 appears to have differential effects in tumor versus "normal" cells in that ablation of PLK1 induced mitotic catastrophe and eventual cell death but G2 arrest in "normal" cells. One plausible explanation is that tumor cells are defective in checkpoint controls and unable to arrest and thus undergo mitotic catastrophe. The roles of PLK2, PLK3, and PLK4 remain elusive.

The expression of PLK1 is restricted to proliferative tissues. Overexpression of PLK1 was detected in solid tumors of various origins (breast, lung, colon, stomach, ovary, smooth muscle, and esophagus) and in non-Hodgkin lymphomas. Furthermore PLK1 has transforming activity; constitutive expression of PLK1 in NIH3T3 cells causes oncogenic focus formation, transformed cells grow in soft agar and form tumors in nude mice.

Therefore, blocking PLK1 kinase activity by a small molecule inhibitor represents a novel approach to target mitosis and may be clearly differentiated from other mitosis-targeting agents on the market such as tubulin binders.

Other therapies which involve the disruption of microtubule formation and degradation through the use of taxanes and vinca alkaloids have become successful ways of treating cancer. Some cancerous cells are able to evade the G2/M cell cycle arrest effect of taxanes and vinca alkaloids. PLK1 inhibition provides a means to target those cells which are able to evade the G2/M cell cycle arresting effect of taxanes and vinca alkaloids.

U.S. Pat. No. 4,818,270 discloses structurally unrelated benzimidazole-thiazole compounds for use as herbicides.

WO200212242 discloses bicyclo-pyrazole compounds that are inhibitors of PLK1. WO200262804 discloses oxazolyl-pyrazole derivatives that are inhibitors of PLK1. WO2003070283 discloses duplex RNAs antisense oligonucleotides that are inhibitors of PLK1. WO2003072062 discloses (E)-2,6-dialkoxystyryl-4-substituted benzylsulfones that are inhibitors of PLK1. WO2003093249 discloses thiazolidinone compounds that are inhibitors of PLK1. WO2004011610 discloses antisense compounds that are inhibitors of PLK1. WO2004014899 discloses thiophene compounds that are inhibitors of PLK1. WO2004043936 discloses pyrimidine compounds that are inhibitors of PLK1. WO2004046317 discloses products and processes for modulating peptide-peptide binding domain interactions including an invention for providing 3-D structures of PLK. WO2004067000 discloses benzothiazole-3-oxides that are inhibitors of PLK1. WO2004074244 discloses pyrimidine compounds that are inhibitors of PLK1. WO2004087652 discloses imidazotriazine compounds that are inhibitors of PLK1. WO2005019193 discloses phenylurea compounds that are inhibitors of PLK1. WO2005042505 discloses thiazolidinones that are inhibitors of PLK1. WO2005042525 discloses pyrimidin-4-yl-3,4-thione compounds that are inhibitors of PLK1. WO2005075470 discloses thiazole compounds that are inhibitors of PLK1.

SUMMARY OF THE INVENTION

According to a first aspect of the invention, there is provided a compound of formula (1):

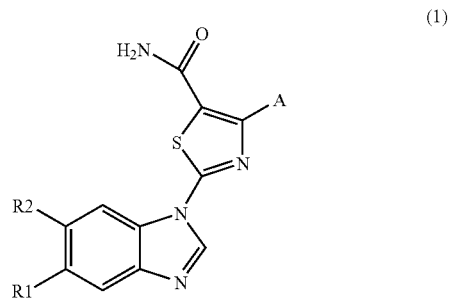

where:
A is selected from the group consisting of phenyl, 2-chlorophenyl, 3-chlorophenyl, 4-chlorophenyl, 2-trifluoromethylphenyl, 3-trifluoromethylphenyl, and 4-trifluoromethylphenyl;
$R_1$ is selected from the group consisting of H, $OCH_3$, and

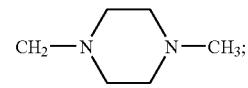

$R_2$ is selected from the group consisting of H and $Z-Q-R_3$, where Z is selected from the group consisting of nothing, O, and C(O), Q is selected from the group consisting of $(CH_2)_m$ and $CH_2CH(OH)CH_2$ and m is an integer from 0 to 4;
$R_3$ is selected from the group consisting of

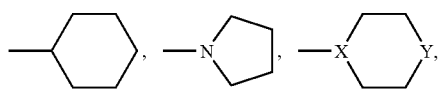

and $-NR_4R_5$;
$R_4$ and $R_5$ are independently selected from the group consisting of H, $CH_3$, $(CH_2)_2OH$, $(CH_2)_2N(CH_3)_2$,

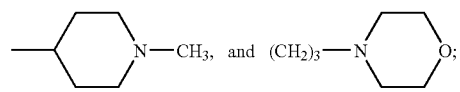

X is selected from the group consisting of CH and N;
Y is selected from the group consisting of C, $OCHR_6$, and $NR_7$;

where

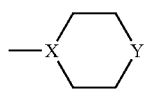

must contain at least one nitrogen atom;
$R_6$ is selected from the group consisting of H, $NH_2$, and $NHC(O)R_8$;
$R_7$ is selected from the group consisting of H, $CH_3$, and $(CH_2)_2OH$,
$R_8$ is selected from the group consisting of OtBu, $OC(CH_3)_2NH_2$, $OC(CH_3)_2NHC(O)OtBu$, and

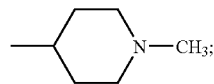

and
pharmaceutically acceptable salts thereof.

In another aspect of the invention relates to pharmaceutical compositions comprising of a compound of formula (1). In one embodiment, the pharmaceutical composition further comprises a pharmaceutically acceptable carrier, diluent, or excipient.

In a third aspect of the invention, there is provided a method for treating a subject afflicted with a disease or condition that responds to modulation of PLK1 activity, comprising administering to the subject an amount of a compound of formula (1) or a pharmaceutically acceptable salt, solvate or physiologically functional derivative thereof, or a composition comprising an amount of a compound of formula (1) or a pharmaceutically acceptable salt, solvate or physiologically functional derivative thereof and one or more pharmaceutically acceptable excipients or adjuvants effective to modulate the activity of PLK1 activity in the subject, wherein the modulation ameliorates the disease or condition.

In a fourth aspect of this invention, there is described a method for inhibiting proliferation of cells. The method involves contacting proliferating cells with an amount of a compound of formula (1) or a pharmaceutically acceptable salt, solvate, or physiologically functional derivative thereof sufficient to inhibit proliferation of such treated cells whereby such cellular treatment inhibits PLK. In another aspect of the present invention, there is described the means to inhibit cells in the stage of mitosis by treating cells with sufficient quantity of a compound of formula (1) or a pharmaceutically acceptable salt, solvate, or physiologically function derivative thereof thereby inhibiting PLK.

DETAILED DESCRIPTION OF THE INVENTION

All patents, patent applications and publications mentioned in the present specification are hereby incorporated by reference in their entirety. In case of a conflict in terminology, the present specification is controlling.

DEFINITIONS

Unless otherwise indicated, the following definitions are set forth to illustrate and define the meaning and scope of the various terms used to describe the invention herein.

The term "halogen" refers to one or more members selected from fluorine, chlorine, bromine, and iodine, preferably to fluorine and chlorine.

The term "pharmaceutically acceptable salts" embraces salts of the compounds of formula (I) with inorganic or organic acids such as hydrochloric acid, hydrobromic acid, nitric acid, sulfuric acid, phosphoric acid, citric acid, formic acid, maleic acid, acetic acid, fumaric acid, succinic acid, tartaric acid, methanesulfonic acid, p-toluenesulfonic acid and the like, which are non-toxic to living organisms.

This term also encompasses carboxylate salts having inorganic cations, such as alkali and alkaline earth metal cations (for example, lithium, sodium, potassium, magnesium, barium and calcium); ammonium cations; or organic cations, for example, dibenzylammonium, benzylammonium, 2-hydroxyethylammonium, bis(2-hydroxyethyl) ammonium, phenylethylbenzylammonium, and the like. Other cations encompassed by the above term include the protonated form of procaine, quinine and N-methylglucosamine, and the protonated forms of basic amino acids such as glycine, ornithine, histidine, phenylglycine, lysine, and arginine.

The term "leaving group" is a chemical group which is removed or replaced during a reaction. Examples of leaving groups are halogen, mesylate and tosylate.

Thus, the invention provides a compound of formula (1)

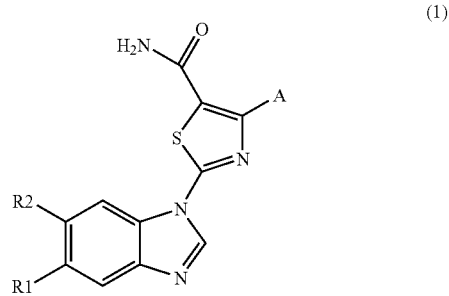

(1)

wherein:
A is selected from the group consisting of phenyl, 2-chlorophenyl, 3-chlorophenyl, 4-chlorophenyl, 2-trifluoromethylphenyl, 3-trifluoromethylphenyl, and 4-trifluoromethylphenyl;
$R_1$ is selected from the group consisting of H, $OCH_3$, and

$R_2$ is selected from the group consisting of H and $Z-Q-R_3$, where Z is selected from the group consisting of nothing, O, and C(O), Q is selected from the group consisting of $(CH_2)_m$ and $CH_2CH(OH)CH_2$ and m is an integer from 0 to 4;
$R_3$ is selected from the group consisting of

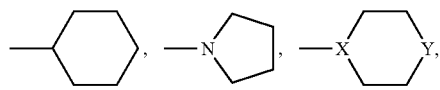

and $-NR_4R_5$;
$R_4$ and $R_5$ are independently selected from the group consisting of H, $CH_3$, $(CH_2)_2OH$, $(CH_2)_2N(CH_3)_2$.

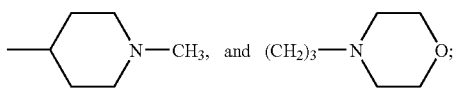

X is selected from the group consisting of CH and N;
Y is selected from the group consisting of O, $CHR_6$, and $NR_7$ where

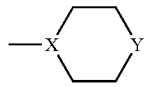

must contain at least one nitrogen atom;
$R_6$ is selected from the group consisting of H, $NH_2$, and $NHC(O)R_8$;
$R_7$ is selected from the group consisting of H, $CH_3$, and $(CH_2)_2OH$;
$R_8$ is selected from the group consisting of OtBu, $OC(CH_3)_2NH_2$, $OC(CH_3)_2NHC(O)OtBu$, and

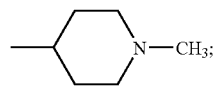

and pharmaceutically acceptable salts thereof.

In another embodiment, the invention is directed to compounds of formula (1) where A is 3-chlorophenyl, $R_1$ is H or $OCH_3$, $R_2$ is $O-(CH_2)_m-R_3$, $R_3$ is

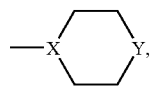

and Y is $NR_7$.

In another embodiment, the invention is directed to compounds of formula (1) where A is 3-chlorophenyl, $R_1$ is H or $OCH_3$, and $R_2$ is $-(CH_2)_m-R_3$.

In another embodiment, the invention is directed to compounds of formula (1) where A is 3-chlorophenyl, $R_1$ is H or $OCH_3$, $R_2$ is $-(CH_2)_m-R_3$, m is 1 and $R_3$ is selected from the group consisting of

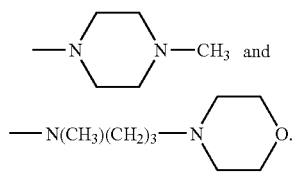

In another embodiment, the invention is directed to compounds of formula (1) where A is 3-chlorophenyl, $R_1$ is H or $OCH_3$, $R_2$ is $O-(CH_2)_m-R_3$, $R_3$ is

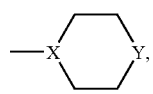

and $R_6$ is selected from the group consisting of H, $CH_3$, and $(CH_2)_2OH$.

In another embodiment, the invention is directed to compounds of formula (1) where A is 3-chlorophenyl, $R_1$ is H or $OCH_3$, $R_2$ is $O-(CH_2)_m-R_3$, $R_3$ is

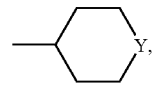

Y is $NR_7$ and $R_7$ is selected from the group consisting of H, $CH_3$, and $(CH_2)_2OH$.

In another embodiment, the invention is directed to compounds of formula (1) where A is 3-chlorophenyl, $R_1$ is H or $OCH_3$, $R_2$ is $O-(CH_2)_m-R_3$, and $R_3$ is

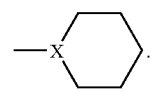

In another embodiment, the invention is directed to compounds of formula (1) where A is 3-chlorophenyl, $R_1$ is H or $OCH_3$, $R_2$ is $O-(CH_2)_m-R_3$, and $R_3$ is

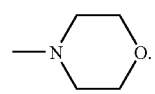

In another embodiment, the invention is directed to compounds of formula (1) where A is 3-chlorophenyl, $R_1$ is H or $OCH_3$, $R_2$ is $-O(CH_2)_m-R_3$, $R_3$ is

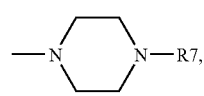

and $R_7$ is selected from the group consisting of H, $CH_3$, and $(CH_2)_2OH$.

In another embodiment, the invention is directed to compounds of formula (1) where A is 3-chlorophenyl, $R_1$ is H or $OCH_3$, $R_2$ is $O-(CH_2)_m-R_3$, and $R_3$ is

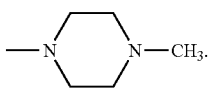

In another embodiment, the invention is directed to compounds of formula (1) where A is 3-chlorophenyl, $R_1$ is H or $OCH_3$, $R_2$ is $O-(CH_2)_m-NR_4R_5$.

In another embodiment, the invention is directed to compounds of formula (1) where A is 3-chlorophenyl, $R_1$ is H or $OCH_3$, $R_2$ is $O-(CH_2)_3-N(CH_2CH_2OH)_2$.

In another embodiment, the invention is directed to compounds of formula (1) where A is 3-chlorophenyl, $R_1$ is H or $OCH_3$, $R_2$ is $O-(CH_2)_3-NHCH_2CH_2OH$.

In another embodiment, the invention is directed to a compound selected from the group consisting of:
2-[6-(4-Methyl-piperazin-1-ylmethyl)-benzoimidazol-1-yl]-4-phenyl-thiazole-5-carboxylic acid amide;
4-(3-Chloro-phenyl)-2-[6-(4-methyl-piperazin-1-ylmethyl)-benzoimidazol-1-yl]-thiazole-5-carboxylic acid amide;

4-(3-Chloro-phenyl)-2-[5-(4-methyl-piperazin-1-ylmethyl)-benzoimidazol-1-yl]-thiazole-5-carboxylic acid amide;

4-(3-Chloro-phenyl)-2-(6-morpholin-4-ylmethyl-benzoimidazol-1-yl)-thiazole-5-carboxylic acid amide;

4-(3-Chloro-phenyl)-2-{6-[4-(2-hydroxy-ethyl)-piperazin-1-ylmethyl]-benzoimidazol-1-yl}-thiazole-5-carboxylic acid amide;

4-(3-Chloro-phenyl)-2-(6-{[(2-dimethylamino-ethyl)-methyl-amino]-methyl}-benzoimidazol-1-yl)-thiazole-5-carboxylic acid amide;

4-(3-Chloro-phenyl)-2-{6-[(1-methyl-piperidin-4-ylamino)-methyl]-benzoimidazol-1-yl}-thiazole-5-carboxylic acid amide;

4-(3-Chloro-phenyl)-2-(6-piperidin-1-ylmethyl-benzoimidazol-1-yl)-thiazole-5-carboxylic acid amide;

4-(3-Chloro-phenyl)-2-{6-[2-(4-methyl-piperazin-1-yl)-ethyl]-benzoimidazol-1-yl}-thiazole-5-carboxylic acid amide;

3-[5-Carbamoyl-4-(3-chloro-phenyl)-thiazol-2-yl]-3H-benzoimidazole-5-carboxylic acid (1-methyl-piperidin-4-yl)-amide;

4-(3-Chloro-phenyl)-2-[6-(4-methyl-piperazine-1-carbonyl)-benzoimidazol-1-yl]-thiazole-5-carboxylic acid amide;

1-{3-[5-Carbamoyl-4-(3-chloro-phenyl)-thiazol-2-yl]-3H-benzoimidazol-5-ylmethyl}-piperidin-4-yl)-carbamic acid tert-butyl ester;

2-[6-(4-Amino-piperidin-1-ylmethyl)-benzoimidazol-1-yl]-4-(3-chloro-phenyl)-thiazole-5-carboxylic acid amide;

1-Methyl-piperidine-4-carboxylic acid (1-{3-[5-carbamoyl-4-(3-chloro-phenyl)-thiazol-2-yl]3H-benzoimidazol-5-ylmethyl}-piperidin-4-yl)-amide;

[1-(1-{3-[5-Carbamoyl-4-(3-chloro-phenyl)-thiazol-2-yl]-3H-benzoimidazol-5-ylmethyl}-piperidin-4-ylcarbamoyl)-1-methyl-ethyl]-carbamic acid tert-butyl ester;

2-{6-[4-(2-Amino-2-methyl-propionylamino)-piperidin-1-ylmethyl]-benzoimidazol-1-yl}-4-(3-chloro-phenyl)-thiazole-5-carboxylic acid amide;

2-[6-(4-Methyl-piperazin-1-ylmethyl)-benzoimidazol-1-yl]-4-(2-trifluoromethyl-phenyl)-thiazole-5-carboxylic acid amide;

4-(4-Chloro-phenyl)-2-[5-(4-methyl-piperazin-1-ylmethyl)-benzoimidazol-1-yl]-thiazole-5-carboxylic acid amide;

4-(4-Chloro-phenyl)-2-[6-(4-methyl-piperazin-1-ylmethyl)-benzoimidazol-1-yl]-thiazole-5-carboxylic acid amide;

4-(2-Chloro-phenyl)-2-[6-(4-methyl-piperazin-1-ylmethyl)-benzoimidazol-1-yl]-thiazole-5-carboxylic acid amide;

4-(3-Chloro-phenyl)-2-[6-(piperidin-4-yloxy)-benzoimidazol-1-yl]-thiazole-5-carboxylic acid amide;

4-(3-Chloro-phenyl)-2-[6-(1-methyl-piperidin-4-yloxy)-benzoimidazol-1-yl]-thiazole-5-carboxylic acid amide;

4-(3-Chloro-phenyl)-2-[6-(piperidin-4-ylmethoxy)-benzoimidazol-1-yl]-thiazole-5-carboxylic acid amide;

4-(3-Chloro-phenyl)-2-[6-(1-methyl-piperidin-4-ylmethoxy)-benzoimidazol-1-yl]-thiazole-5-carboxylic acid amide;

4-(3-Chloro-phenyl)-2-(6-cyclohexyloxy-benzoimidazol-1-yl)-thiazole-5-carboxylic acid amide;

4-(3-Chloro-phenyl)-2-[6-(2-morpholin-4-yl-ethoxy)-benzoimidazol-1-yl]-thiazole-5-carboxylic acid amide;

4-(3-Chloro-phenyl)-2-[6-(2-piperidin-1-yl-ethoxy)-benzoimidazol-1-yl]-thiazole-5-carboxylic acid amide;

4-(3-Chloro-phenyl)-2-{6-[2-(4-methyl-piperazin-1-yl)-ethoxy]-benzoimidazol-1-yl}-thiazole-5-carboxylic acid amide;

4-(3-Chloro-phenyl)-2-[6-(2-dimethylamino-ethoxy)-benzoimidazol-1-yl]-thiazole-5-carboxylic acid amide;

4-(3-Chloro-phenyl)-2-[6-(3-morpholin-4-yl-propoxy)-benzoimidazol-1-yl]-thiazole-5-carboxylic acid amide;

4-(3-Chloro-phenyl)-2-[6-(3-dimethylamino-propoxy)-benzoimidazol-1-yl]-thiazole-5-carboxylic acid amide;

4-(3-Chloro-phenyl)-2-[6-(3-piperidin-1-yl-propoxy)-benzoimidazol-1-yl]-thiazole-5-carboxylic acid amide;

4-(3-Chloro-phenyl)-2-{6-[3-(4-methyl-piperazin-1-yl)-propoxy]-benzoimidazol-1-yl}-thiazole-5-carboxylic acid amide;

4-(3-Chloro-phenyl)-2-[6-(3-pyrrolidin-1-yl-propoxy)-benzoimidazol-1-yl]-thiazole-5-carboxylic acid amide;

2-(6-{3-[Bis-(2-hydroxy-ethyl)-amino]-propoxy}-benzoimidazol-1-yl)-4-(3-chloro-phenyl)-thiazole-5-carboxylic acid amide;

4-(3-Chloro-phenyl)-2-{6-[3-(2-hydroxy-ethylamino)-propoxy]-benzoimidazol-1-yl}-thiazole-5-carboxylic acid amide;

4-(3-Chloro-phenyl)-2-{6-[4-(4-methyl-piperazin-1-yl)-butoxy]-benzoimidazol-1-yl}-thiazole-5-carboxylic acid amide;

4-(3-Chloro-phenyl)-2-[6-(4-morpholin-4-yl-butoxy)-benzoimidazol-1-yl]-thiazole-5-carboxylic acid amide;

4-(3-Chloro-phenyl)-2-{6-[2-hydroxy-3-(4-methyl-piperazin-1-yl)-propoxy]-benzoimidazol-1-yl}-thiazole-5-carboxylic acid amide;

4-(3-Chloro-phenyl)-2-[6-(2-hydroxy-3-morpholin-4-yl-propoxy)-benzoimidazol-1-yl]-thiazole-5-carboxylic acid amide;

4-(3-Chloro-phenyl)-2-[6-(4-morpholin-4-yl-butyl)-benzoimidazol-1-yl]-thiazole-5-carboxylic acid amide;

4-(3-Chloro-phenyl)-2-{5-methoxy-6-[3-(4-methyl-piperazin-1-yl)-propoxy]-benzoimidazol-1-yl}-thiazole-5-carboxylic acid amide;

4-(3-Chloro-phenyl)-2-[5-methoxy-6-(3-morpholin-4-yl-propoxy)-benzoimidazol-1-yl]-thiazole-5-carboxylic acid amide;

4-(3-Chloro-phenyl)-2-{5-methoxy-6-[2-(4-methyl-piperazin-1-yl)-ethoxy]-benzoimidazol-1-yl}-thiazole-5-carboxylic acid amide;

4-(3-Chloro-phenyl)-2-[5-methoxy-6-(2-morpholin-4-yl-ethoxy)-benzoimidazol-1-yl]-thiazole-5-carboxylic acid amide;

4-(3-Chloro-phenyl)-2-[5-methoxy-6-(4-methyl-piperazin-1-ylmethyl)-benzoimidazol-1-yl]-thiazole-5-carboxylic acid amide;

2-[6-(4-Methyl-piperazin-1-ylmethyl)-benzoimidazol-1-yl]-4-(4-trifluoromethyl-phenyl)-thiazole-5-carboxylic acid amide;

2-[6-(4-Methyl-piperazin-1-ylmethyl)-benzoimidazol-1-yl]-4-(3-trifluoromethyl-phenyl)-thiazole-5-carboxylic acid amide;

2-(6-{[Bis-(3-morpholin-4-yl-propyl)-amino]-methyl}-benzoimidazol-1-yl)-4-(3-chloro-phenyl)-thiazole-5-carboxylic acid amide;

4-(3-Chloro-phenyl)-2-(6-{[methyl-(3-morpholin-4-yl-propyl)-amino]-methyl}-benzoimidazol-1-yl)-thiazole-5-carboxylic acid amide.

In another embodiment, the invention is directed to a method for treating a subject afflicted with a disease or condition that responds to modulation of PLK1 activity, comprising administering to the subject an amount of a compound as described above effective to modulate the activity of PLK1 activity in the subject, wherein the modulation ameliorates the disease or condition.

The compounds of general formula 1 in this invention may be derivatized at functional groups to provide derivatives which are capable of conversion back to the parent compound in vivo.

The invention also relates to pharmaceutical compositions comprising a compound as defined above and a pharmaceutically acceptable carrier and/or adjuvant.

The compounds of formula I may be manufactured by the methods given below, by the methods given in the examples or by analogous methods. Based on the present disclosure, appropriate reaction conditions for the individual reaction steps would be apparent to the person skilled in the art. Starting materials are either commercially available or may be prepared by methods analogous to the methods given below or in the examples or by methods known in the art.

The compounds of formula I and/or their pharmaceutically acceptable salts may be used as medicaments, e.g. in the form of pharmaceutical compositions for enteral, parenteral or topical administration. They may be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions may be effected in a manner which will be familiar to any person skilled in the art by bringing the described compounds of formula (I) and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts may be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula 1 can vary within wide limits depending on the disease to be controlled, the age and the individual condition of the patient and the mode of administration, and will, of course, be fitted to the individual requirements in each particular case. For adult patients a daily dosage of about 1 to 1000 mg, especially about 1 to 750 mg, or 1 to 500 mg, or 1 to 250 mg, or 1 to 200 mg, or 1 to 150 mg, or 1 to 100 mg, or 1 to 75 mg, or 1 to 50 mg, or 1 to 25 mg, or 1 to 10 mg, may be administered. Depending on severity of the disease and the precise pharmacokinetic profile the compound could be administered with one or several daily dosage units, e.g. in 1 to 4 dosage units.

The pharmaceutical preparations conveniently contain about 1 to 500 mg, 1 to 250 mg, 1 to 200 mg, 1 to 150 mg, 1 to 100 mg, 1 to 75 mg, 1 to 50 mg, 1 to 25 mg, or 1 to 10 mg of a compound of formula 1.

Compounds of formula (1) may be conveniently prepared by the methods outlined in the schemes below.

Schemes

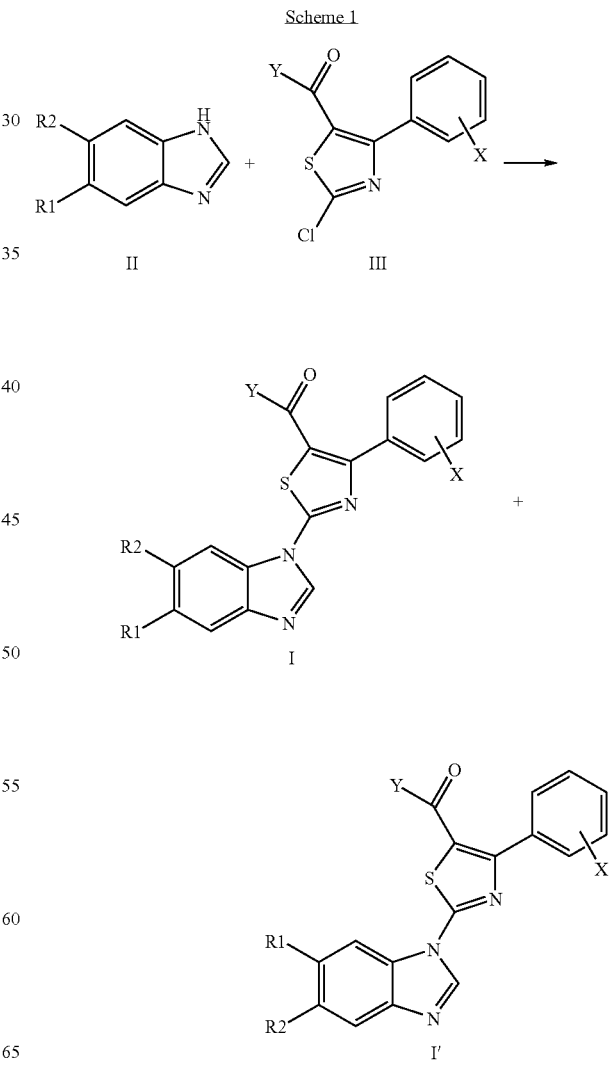

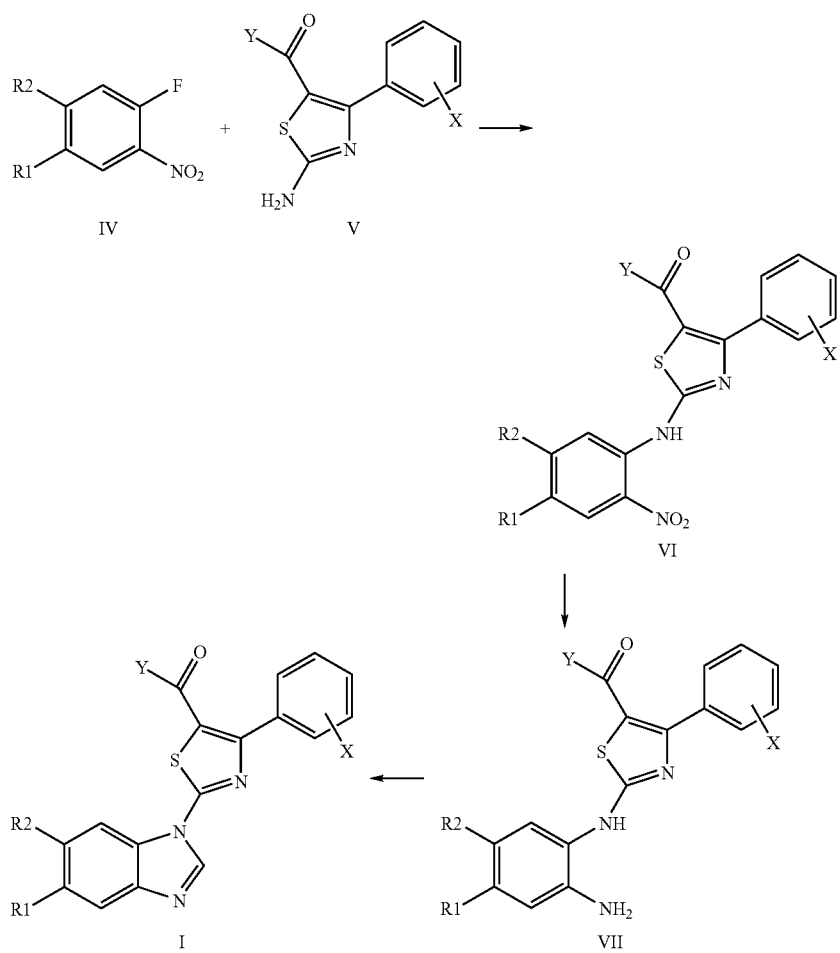

Scheme 2

EXAMPLES

General Methods

In the examples described, temperatures are indicated in degrees C. For mass spectral data, values are given as the MH+/Z ion obtained in the positive mode, electrospray MS measured on a Micromass Platform II mass spectrometer. Unless indicated otherwise, reactions were generally run under an inert atmosphere (argon or nitrogen). Unless indicated otherwise, chromatographic separations were carried using silica gel, solvent mixtures, where indicated are provided as ratio of volumes. In some instances, purifications were carried out using supercritical fluid chromatography (SFC) (Berger Instrument Multi-gram II) using a 3.0×25 cm Daicel Chiralpak OD column or a (R,R)-Whelk-O1 column, eluting with carbon dioxide plus modifier solvent (indicated in parentheses).

Preparation of Compounds (I):

Two general methods were used to prepare the compounds of the invention. The first method, outlined in scheme 1, involves the addition of a preformed, substituted benzimidazole (II) with a substituted 2-chloro-4-phenyl-thiazole-5-carboxylic acid ester (III, Y=O-alkyl) or amide (III, Y=NH$_2$) to form compound I as a mixture of regio-isomers (I and I'). The reaction is carried out in the presence of a base, such as potassium carbonate, cesium carbonate and the like. In some instances R1 and R2 of compound II may be the same as in the final compound I, or, alternatively, may be groups that can be transformed, at some intermediate stage, to another functional group. Examples of this type of functional group conversion are reductive aminations and displacement of leaving groups such as halides or sulfonate esters with an amine. The reductive amination conversion method involves compounds where R1 or R2 contain an aldehyde group or a protected form of an aldehyde, and which are reacted with a primary or secondary amine in the presence of reducing agent such as sodium cyanoborohydride or sodium triacetoxyborohydride. The leaving group displacement conversion involves compounds where R1 or R2 containing an alkyl halide, an alkyl sulfonate ester or an epoxy group react with primary or secondary amines.

The transformation of compound I esters (Y=OR) to the corresponding amide (Y=NH$_2$) is carried in a conventional three step process involving ester hydrolysis to the acid (Y=OH), reaction with standard coupling agents and reaction with ammonia or ammonia salts in the presence of a base.

The second method, outlined in scheme 2, involves the coupling of substituted nitro-benzene (IV) with a substituted 2-amino-4-phenyl-thiazole-5-carboxylic acid ester (V, Y=O-alkyl) or amide (V, Y=NH$_2$) to form 2-(2-nitro-phenylamino)-thiazole-5-carboxylic acid derivative (VI). The nitro group is reduced, under standard conditions such as hydrogenation or zinc metal to the corresponding 2-(2-amino-phenylamino)-thiazole-5-carboxylic acid derivative (VII). Formation of the substituted benzimidazole (I) from compound (VII) is carried out by the cyclodehydration of (VII) with formic acid or trialkoxyorthoformates in acetic acid. Functional group interconversion of the groups R1, R2 and Y are carried in similar fashion as outlined for method 1.

PREPARATION OF INTERMEDIATES

Preparation of 2-amino-thiazoles (V)

The 2-amino-4-phenyl-thiazole-carboxamides were prepared by the general method was used as described by Herschhorn, A., Lerman, L., Weitman, M., Gleenberg, I. O., Nudelman, A., Hizi, A., J., Med., Chem., 2007, 50, 2370-2384.

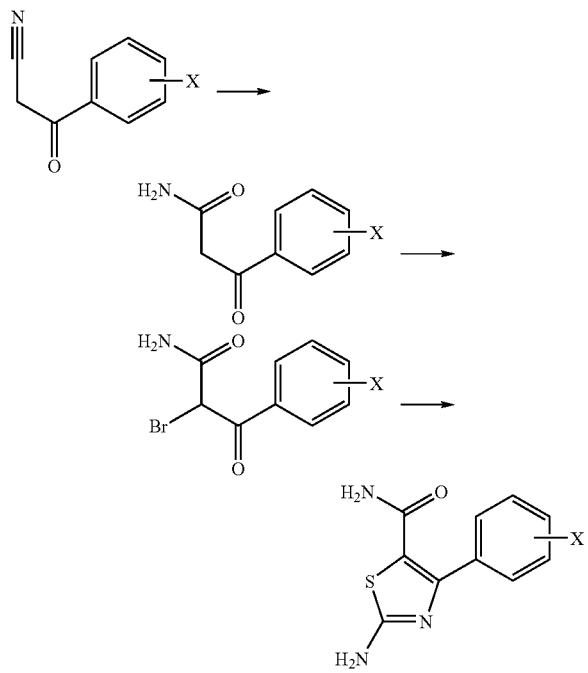

2-Amino-4-(2-trifluoromethyl-phenyl)-thiazole-5-carboxylic acid amide (V.17)

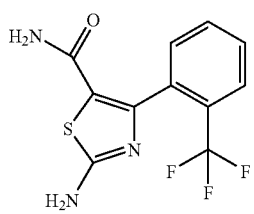

Step 1

To a solution of 20.00 g (0.11 mole) of 2'-(trifluoromethyl) acetophenone in 200 mL of dichloromethane was added 5.5 mL (0.11 mole) of bromine over 90 minutes. A stream of nitrogen was bubbled through the reaction mixture for 15 minutes. The mixture solvent was removed under reduced pressure. The residue was dissolved with ethanol, and then concentrated under reduced pressure to give 27.25 g of 2-bromo-1-(2-trifluoromethyl-phenyl)-ethanone as a yellow oil, which was used in the next step without further purification.

Step 2

A solution of 26.04 g (0.40 mole) of potassium cyanide in 30 mL of water was added to a stirring solution of 27.00 g (0.10 mole) of 2-bromo-1-(2-trifluoromethyl-phenyl)-ethanone in 500 mL of ethanol. The mixture was stirred at room temperature overnight. Water and dichloromethane were added to the mixture. The mixture was then acidified with acetic acid (pH=5-6). The organic layer was separated, washed with brine, dried over anhydrous sodium sulfate and concentrated under reduced pressure. Recrystallization of the residue with ether and hexane gave 14.97 g of 3-oxo-3(2-trifluoromethyl-phenyl)-propionitrile.

Step 3

A solution of 14.5 g (0.068 mole) of 3-oxo-3(2-trifluoromethyl-phenyl)-propionitrile in 340 mL of sulfuric acid was stirred for 5 hours at room temperature. The mixture was slowly poured into ice water with stirring. The mixture was made basic by addition of ammonium hydroxide. The mixture was extracted with ethyl acetate. The organic layer was washed with brine, dried over anhydrous sodium sulfate, filtered and concentrated under reduced pressure to give 13.82 g of 3-oxo-3-(2-trifluoromethyl-phenyl)-propionamide as a yellow solid.

Step 4

A mixture of 13.00 g (0.56 mole) of 3-oxo-3-(2-trifluoromethyl-phenyl)-propionamide and 12.60 g (0.56 mole) of copper (II) bromide in 150 mL of ethyl acetate was heated at reflux for overnight. The mixture was cooled and filtered through short silica gel column, washing the column with ethyl acetate. The filtrate was concentrated under reduced pressure. Purification of the residue by silica gel chromatography, eluting with hexanes-ethyl acetate (gradient, 100:0-70:30) gave 11.50 g of 2-bromo-3-oxo-3-(2-trifluoromethyl-phenyl)-propionamide as a yellow solid.

Step 5

To a solution of 2.80 g (0.37 mole) of thiourea in 1200 mL of ethanol was added 11.40 g (0.37 mole) of 2-bromo-3-oxo-3-(2-trifluoromethyl-phenyl)-propionamide. After stirring at room temperature overnight, the mixture was concentrated under reduced pressure. Purification of the residue by silica gel chromatography, eluting with dichloromethane-methanol (gradient 100:0-80:20) gave 11.80 g of 2-carbamimidoylsulfanyl-3-oxo-3-(2-trifluoromethyl-phenyl)-propionamide as a yellow solid.

Step 6

A mixture of 2.00 g (0.0066 mole) of 2-carbamimidoylsulfanyl-3-oxo-3-(2-trifluoromethyl-phenyl)-propionamide in 80 mL of ethanol was heated to 60 degrees for overnight. The mixture was concentrated under reduce pressure. Purification of the residue by chromatography on C18-reverse phase silica gel, eluting with water-acetonitrile (gradient 100:0-50:50) gave 1.32 g of 2-amino-4-(2-trifluoromethyl-phenyl)-thiazole-5-carboxylic acid amide (V.17) as a yellow solid.

2-Amino-4-(4-chloro-phenyl)-thiazole-5-carboxylic acid amide (V.18)

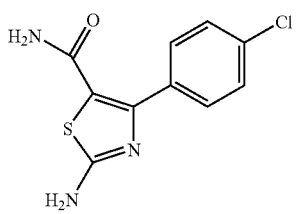

Step 1

A solution of 5.58 g (86 mmole) of potassium cyanide and 1 mL of water was added in one portion to a solution of 8.0 g (34.3 mmole) of α-bromo-p-chloroacetophenone in 50 mL of 95% ethanol. The mixture was stirred at room temperature for 5 hours, then diluted with water and dichloromethane and acidified with acetic acid. The organic layer was washed with brine. The aqueous layers were extracted with dichloromethane. The combined organic layers were dried over anhydrous magnesium sulfate, filtered and concentrated under reduced pressure to give crude 3-(4-chloro-phenyl)-3-oxo-propionitrile which was used in next step without further purification.

Step 2

The crude 3-(4-chloro-phenyl)-3-oxo-propionitrile obtained above was stirred with 100 mL of sulfuric acid at room temperature for 4 hours. The mixture was poured into 500 mL of ice-water and stirred for 30 minutes. The precipitate was collected by filtration, washed with water and dried under reduced pressure to give 5.73 g of 3-(4-chloro-phenyl)-3-oxo-propionamide as a brown solid which was used in next step without further purification.

Step 3

A mixture of 5.73 g (29 mmole) of 3-(4-chloro-phenyl)-3-oxo-propionamide and 9.72 g (43.5 mmole) of copper(II) bromide and 400 mL of ethyl acetate was heated at reflux until the starting material was consumed. After cooling, the mixture was diluted with dichloromethane and filtered through a short plug of silica gel washing with ethyl acetate-dichloromethane (1:1). The filtrate was concentrated under reduced pressure and the residue purified by silica gel chromatography, eluting with ethyl acetate-hexanes (2:3) to give 7.35 g of 2-bromo-3-(4-chloro-phenyl)-3-oxo-propionamide.

Step 4

To a mixture of 7.35 g (26.58 mmole) of 2-bromo-3-(4-chloro-phenyl)-3-oxo-propionamide and 300 mL of ethanol was added 2.02 g (26.58 mmole) of thiourea. The mixture was stirred at room temperature for 4 hours and then concentrated under reduced pressure. The residue was purified by silica gel chromatography, eluting with ethyl acetate-dichloromethane (1:3, then 3:1, then 1:0). Recrystallization of the residue gave 1.11 g of 2-amino-4-(4-chloro-phenyl)-thiazole-5-carboxylic acid amide (V.18) as pale yellow crystals.

2-Amino-4-(2-chloro-phenyl)-thiazole-5-carboxylic acid amide (V.20)

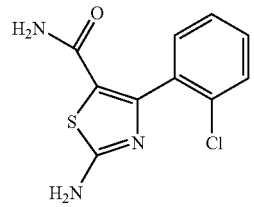

Step 1

A mixture of 17.0 g (94.65 mmole) of 3-(2-chloro-phenyl)-3-oxo-propionitrile and 50 mL of sulfuric acid was stirred at room temperature for 18 hours. The mixture was poured into ice-water and extracted three times with ethyl acetate. The combined organic phases were washed with saturated aqueous sodium carbonate solution and brine, dried over anhydrous magnesium sulfate, filtered and concentrated under reduced pressure. The residue was purified by silica gel chromatography eluting with ethyl acetate-hexanes (gradient 20:80-70:30) to give 14.12 g of 3-(2-chloro-phenyl)-3-oxo-propionamide.

Step 2

A mixture of 14.12 g (71.45 mmole) of 3-(2-chloro-phenyl)-3-oxo-propionamide, 39.15 g (180 mmole) of copper(II) bromide and 100 mL of ethyl acetate was heated at reflux for 2 days. The cooled reaction mixture was then passed through a short silica gel column eluting with ethyl acetate. After concentration under reduced pressure, the residue was purified by silica gel chromatography, eluting with ethyl acetate-hexanes (gradient 5:95-40:60) to give 2.33 g of 2-bromo-3-(2-chloro-phenyl)-3-oxo-propionamide.

Step 3

A mixture of 2.33 g (8.43 mmole) of 2-bromo-3-(2-chloro-phenyl)-3-oxo-propionamide, 0.77 g (10.11 mmole) of thiourea and 20 mL of ethanol was stirred at room temperature for 18 hours. The mixture was then concentrated under reduced pressure. The residue was purified by chromatography on C18 reverse phase silica gel, eluting with acetonitrile-water (gradient 0:100-50:50) to give 0.72 g of 2-amino-4-(2-chloro-phenyl)-thiazole-5-carboxylic acid amide (V.20).

2-Amino-4-(4-trifluoromethyl-phenyl)-thiazole-5-carboxylic acid amide (V.47)

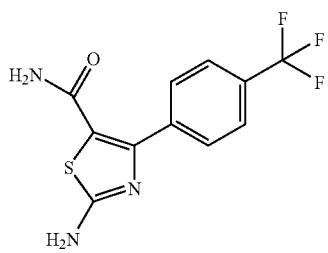

Step 1

A solution of 25.64 g (96.0 mmole) of 2-bromo-1-(4-trifluoromethyl-phenyl)-ethanone, 10.27 g (105.7 mmole) of potassium thiocyanate and 130 mL of ethanol (130 mL) was heated to reflux for 2 hours, and then concentrated under reduced pressure. The residue was taken up in 700 mL of ethyl acetate, washed three times with 75 mL of water, then 75 mL of brine, dried over anhydrous sodium sulfate, filtered and concentrated under reduced pressure to give 22.57 g of 2-thiocyanato-1-(4-trifluoromethyl-phenyl)-ethanone as an orange-brown solid.

Step 2

A mixture of 22.52 g (91.8 mmole) of 2-thiocyanato-1-(4-trifluoromethyl-phenyl)-ethanone 9 mL of 50% aqueous sulfuric acid and 45 mL of acetic acid was heated at reflux for 1.5 hours. The mixture was cooled, poured into 500 mL of ice water and stirred for 30 minutes. The solid was collected by filtration, washing with water, to give 21.33 g of 4-(4-trifluoromethyl-phenyl)-3H-thiazol-2-one as a tan solid.

Step 3

2-chloro-4-(4-trifluoromethyl-phenyl)-thiazole

A mixture of 28.05 g (114.4 mmole) of 4-(4-trifluoromethyl-phenyl)-3H-thiazol-2-one and 85 mL (0.92 mole) of phosphorus oxychloride was heated at reflux for 5 hours. The mixture was cooled and the excess phosphorus oxychloride was removed under reduced pressure. The residue was diluted with ethyl acetate and the slurry was poured onto ice. The mixture was made basic by the addition of saturated aqueous sodium carbonate solution. The ethyl acetate layer was dried over anhydrous sodium sulfate, filtered and concentrated under reduced pressure. The residue was purified by silica gel chromatography eluting with ethyl acetate-hexanes (gradient 10:90-20:80) to give 19.34 g of 2-chloro-4-(4-trifluoromethyl-phenyl)-thiazole as a light brown solid.

Step 4

To a solution of 5.0 g (19.0 mmole) of 2-chloro-4-(4-trifluoromethyl-phenyl)-thiazole and 57 mL of tetrahydrofuran at −78 degrees, was added, over 10 minutes, 9.5 mL of 2.5 M n-butyl lithium in hexanes solution. After 30 minutes, 1.1 mL of 2.5 M n-butyl lithium in hexanes solution was added The mixture was stirred for 2 hours and then 10.63 mL (107.8 mmole) of ethyl chloroformate was added quickly to a rapidly stirring solution. After 15 minutes, the cooling bath was removed and the mixture was stirred at room temperature for 22 minutes. The reaction was quenched by the addition of 75 mL of 1M hydrochloric acid, stirred for 5 minutes and then diluted with 500 mL of ethyl acetate. The ethyl acetate layer was washed twice with 75 mL of water, once with 75 mL of brine, dried over anhydrous sodium sulfate, filtered and concentrated under reduced pressure. The residue was purified by silica gel chromatography, eluting dichloromethane-hexanes (gradient 10:90-50:50) to give 4.94 g of 2-chloro-4-(4-trifluoromethyl-phenyl)-thiazole-5-carboxylic acid ethyl ester as a light yellow solid.

Step 5

To a stirred solution of 2.41 g (7.18 mmole) of 2-chloro-4-(4-trifluoromethyl-phenyl)-thiazole-5-carboxylic acid ethyl ester, 2.4 mL of acetone and 2.4 mL of water was added 2.34 g (35.63 mmole) of sodium azide. The reaction mixture was heated at 70 degrees for 16 hours and then partitioned between 200 mL of ethyl acetate and 75 mL of water. The aqueous layer was extracted twice with 55 mL of ethyl acetate. The combined ethyl acetate layers were washed with 50 mL of brine, dried over anhydrous sodium sulfate, filtered and concentrated under reduced pressure to give 2.44 g of 2-azido-4-(4-trifluoromethyl-phenyl)-thiazole-5-carboxylic acid ethyl ester as a dark amber oil.

Step 6

To a mixture of 2.44 g (7.14 mmole) of 2-azido-4-(4-trifluoromethyl-phenyl)-thiazole-5-carboxylic acid ethyl ester and 45 mL of tetrahydrofuran was added, 3.01 g (71.5 mmole) of lithium hydroxide monohydrate in 33 mL of water. The mixture was stirred at room temperature for 17 hours and then diluted with 300 mL of diethyl ether. The ether layer was extracted three times with 100 mL of water. The combined aqueous phases were acidified by the addition of 1M hydrochloric acid and extracted three times with 100 mL of ethyl acetate. The combined ethyl acetate layers were washed with 50 mL of brine, dried over anhydrous sodium sulfate, filtered and concentrated under reduced pressure to give 1.76 g of 2-azido-4-(4-trifluoromethyl-phenyl)-thiazole-5-carboxylic acid as a light yellow solid.

Step 7

To a solution of 1.76 g (5.60 mmole) of 2-azido-4-(4-trifluoromethyl-phenyl)-thiazole-5-carboxylic acid and 30 mL of dimethylformamide was added 2.75 g (7.01 mmole) of 1-[bis(dimethylamino)methylene]-1H-1,2,3-triazolo[4,5-b]pyridinium, 3-oxide, hexafluorophosphate(1-) (1:1) and 3.0 mL (17.2 mmole) of ethyldiisopropylamine. The mixture was stirred for 18 minutes, then 0.4541 g (8.49 mmole) of ammonium chloride was added. The mixture was concentrated under reduced pressure and diluted with 350 mL of ethyl acetate and 75 mL of water. The ethyl acetate layer was washed with 50 mL of water, 50 mL of saturated aqueous sodium bicarbonate, 50 mL of brine, dried over anhydrous sodium sulfate, filtered, and concentrated under reduced pressure. The residue was purified by silica gel chromatography, eluting with ethyl acetate-hexanes (gradient 10:90-100:0) to give 1.384 g of 2-azido-4-(4-trifluoromethyl-phenyl)-thiazole-5-carboxylic acid amide as a light yellow solid.

Step 8

To a solution of 0.6727 g (2.147 mmole) of 2-azido-4-(4-trifluoromethyl-phenyl)-thiazole-5-carboxylic acid amide, 20 mL of methanol and 20 mL of tetrahydrofuran was added 1.42 g (21.8 mg-atom) of zinc and 2.84 g (53.1 mmole) of ammonium chloride. The mixture was stirred vigorously for 1 hour and then filtered through Diatomaceous earth, washing the pad with methanol and tetrahydrofuran. The filtrate was concentrated under reduced pressure and then diluted with 350 mL of ethyl acetate, washed three times with 75 mL of water, once with brine, dried over anhydrous sodium sulfate, filtered, concentrated under reduced pressure to give 0.6276 g of 2-amino-4-(4-trifluoromethyl-phenyl)-thiazole-5-carboxylic acid amide (V.47) as an off-white solid.

2-Amino-4-(3-trifluoromethyl-phenyl)-thiazole-5-carboxylic acid amide (V.48)

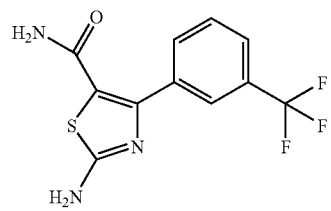

Step 1

A mixture of 10.17 g (36.83 mmole) of 2-bromo-1-(3-trifluoromethyl-phenyl)-ethanone, 4.07 g (41.98 mmole) of potassium thiocyanate and ethanol was heated at reflux for 2 hours. The cooled mixture was concentrated under reduced pressure. The residue was taken up in 225 mL of ethyl acetate, washed three times with 50 mL of water, then 50 mL of brine, dried over anhydrous sodium sulfate, filtered and concentrated under reduced pressure to give 8.85 g of 2-thiocyanato-1-(3-trifluoromethyl-phenyl)-ethanone.

Step 2

A mixture of 26.42 g (107.74 mmole) of 2-thiocyanato-1-(3-trifluoromethyl-phenyl)-ethanone, 11 mL of 50% aqueous sulfuric acid and 55 mL of acetic acid was heated at reflux for 1 hour. The mixture was cooled, poured into 500 mL of ice water mixture and stirred for 30 minutes. The solid was collected by filtration, washing with water to give 24 g of 4-(3-trifluoromethyl-phenyl)-3H-thiazol-2-one as a light orange-brown solid.

Step 3

A mixture of 24.55 g (100.1 mmole) of 4-(3-trifluoromethyl-phenyl)-3H-thiazol-2-one and 75 mL (0.811 mole) of phosphorus oxychloride was heated at reflux for 3 hours. The cooled mixture was concentrated under reduced pressure. The residue was diluted with ethyl acetate and poured onto ice. The mixture was made basic by the addition of saturated sodium carbonate solution. The ethyl acetate layer was dried over anhydrous sodium sulfate, filtered, and concentrated under reduced pressure. The residue was purified by silica gel chromatography, eluting with ethyl acetate-hexanes (gradient 10:90-20:80) to give 17.09 g of 2-chloro-4-(3-trifluoromethyl-phenyl)-thiazole as a light brown solid.

Step 4

To a solution of 10.1 g (38.3 mmole) of 2-chloro-4-(3-trifluoromethyl-phenyl)-thiazole in 120 mL of tetrahydrofuran at −78 degrees was added over 20 minutes, 20 mL of 2.5 M n-butyl lithium in hexanes. The mixture was stirred for 2 hours and then 19 mL (93.4 mmole) of ethyl chloroformate was added quickly. The mixture was stirred for 15 minutes, then the cooling bath was removed. After 25 minutes, the reaction was quenched by the addition of 150 mL of 1M hydrochloric acid. The mixture was stirred for 5 minutes, and then diluted with 1 L of ethyl acetate. The ethyl acetate layer was washed twice with 150 mL of water, once with 100 mL of brine, dried over anhydrous sodium sulfate, filtered and concentrated under reduced pressure. The residue was purified by silica gel chromatography, eluting with dichloromethane-hexanes (gradient 10:90-50:50) to give 5.62 g of 2-chloro-4-(3-trifluoromethyl-phenyl)-thiazole-5-carboxylic acid ethyl ester as a golden oil.

Step 5

To a stirred solution of 2.99 g (8.90 mmole) of 2-chloro-4-(3-trifluoromethyl-phenyl)-thiazole-5-carboxylic acid ethyl ester, 27 mL of acetone and 27 mL of water was added 2.97 g (45.15 mmole) of sodium azide. The mixture was heated at 70 degrees for 11 hours. The mixture was partitioned between 200 mL of ethyl acetate and 75 mL of water. The aqueous layer was extracted twice with 60 mL of ethyl acetate. The combined ethyl acetate layers were washed with 50 mL of brine, dried over anhydrous sodium sulfate, filtered and concentrated under reduced pressure to give 2.97 g of 2-azido-4-(3-trifluoromethyl-phenyl)-thiazole-5-carboxylic acid ethyl ester as a dark brown oil.

Step 6

To a mixture of 3.0 g (8.76 mmole) of 2-azido-4-(3-trifluoromethyl-phenyl)-thiazole-5-carboxylic acid ethyl ester, 54 mL of tetrahydrofuran was added 3.71 g (88.3 mmole) of lithium hydroxide monohydrate in 36 mL of water. The mixture was stirred at room temperature for 3 hours, and then diluted with 350 mL of diethyl ether. The mixture was extracted three times with 100 mL of water. The combined aqueous layers were acidified by addition of 1M hydrochloric acid, and extracted three times with 100 mL of ethyl acetate. The combined ethyl acetate layers were washed with 50 mL of brine, dried over anhydrous sodium sulfate, filtered and concentrated under reduced pressure to give 2.20 g of 2-azido-4-(3-trifluoromethyl-phenyl)-thiazole-5-carboxylic acid as a yellow-orange solid.

Step 7

A solution of 2.20 g (7.01 mmole) of 2-azido-4-(3-trifluoromethyl-phenyl)-thiazole-5-carboxylic acid, 38 mL of dimethylformamide, 3.47 g (8.85 mmole) of 1-[bis(dimethylamino)methylene]-1H-1,2,3-triazolo[4,5-b]pyridinium, 3-oxide, hexafluorophosphate(1-) (1:1) and 3.75 mL (21.53 mmole) of ethyldiisopropylamine was stirred at room temperature for 23 minutes, then 0.5733 g (10.72 mmole) of ammonium chloride was added. The mixture was stirred for 2.25 hours, then concentrated under reduced pressure and partitioned between 300 mL of ethyl acetate and 75 mL of water. The ethyl acetate layer was washed twice with 60 mL of water, twice with 55 mL of saturated aqueous sodium bicarbonate, once with 50 mL of brine, dried over anhydrous sodium sulfate, filtered, concentrated under reduced pressure. The residue was purified by silica gel chromatography, eluting with ethyl acetate-hexanes (gradient 10:90-100-:0) to give 1.841 g 2-azido-4-(3-trifluoromethyl-phenyl)-thiazole-5-carboxylic acid amide as a light yellow solid.

Step 8

To a solution of 0.9035 g (2.884 mmole) of 2-azido-4-(3-trifluoromethyl-phenyl)-thiazole-5-carboxylic acid amide, 27 mL of methanol and 27 mL of tetrahydrofuran, was added 1.91 g (29.21 mg-atom) of zinc and 3.82 g (71.42 mmole) of ammonium chloride. The mixture was stirred vigorously for 1 hour, and then filtered through Diatomaceous earth, washing the filter pad with methanol and tetrahydrofuran. The filtrate was concentrated under reduced pressure, diluted with 350 mL of ethyl acetate and washed three times with 100 mL of water, twice with 50 mL of brine, dried over anhydrous sodium sulfate, filtered, concentrated under reduced pressure to give 0.8527 g of 2-amino-4-(3-trifluoromethyl-phenyl)-thiazole-5-carboxylic acid amide (V.48).

Example 1

2-[6-(4-Methyl-piperazin-1-ylmethyl)-benzoimidazol-1-yl]-4-phenyl-thiazole-5-carboxylic acid amide (I.1)

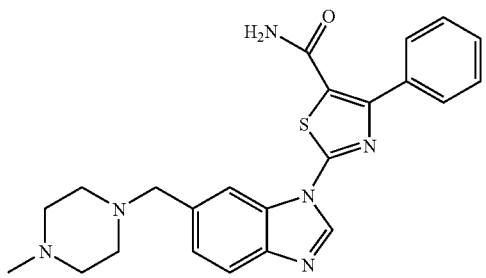

Step 1

A mixture of 0.250 g (1 mmole) of 2-amino-4-phenyl-thiazole-5-carboxylic acid ethyl ester (V.1), 0.215 g (1 mmole) of 4-dimethoxymethyl-2-fluoro-1-nitro-benzene, 0.488 g (1.5 mmole) of cesium carbonate and 5 mL of dimethylformamide was heated at 100 degrees overnight. The cooled mixture was diluted with 30 mL of water and then extracted three times with 20 mL of ethyl acetate. The combined organic layers were washed with brine, dried over anhydrous magnesium sulfate, filtered and concentrated under reduced pressure. The residue was purified by silica gel chromatography, eluting with ethyl acetate-hexanes (gradient 0:100-10:90) to give 0.240 g of 2-(5-dimethoxymethyl-2-nitro-phenylamino)-4-phenyl-thiazole-5-carboxylic acid ethyl ester (VIA a) as an orange solid.

Step 2

A mixture of 0.089 g (0.2 mmole) of 2-(5-dimethoxymethyl-2-nitro-phenylamino)-4-phenyl-thiazole-5-carboxylic acid ethyl ester (VI.1a), 2 mL of actonitrile and 0.5 mL of 1 M hydrochloric acid was stirred at 60 degrees for 30 minutes. The mixture was concentrated under reduced pressure. The residue was diluted with 5 mL of saturated sodium bicarbonate and extracted twice with 20 mL of dichloromethane. The combined organic layers were washed with brine, dried over anhydrous magnesium sulfate, filtered and concentrated under reduced pressure to give 0.080 g of 2-(5-formyl-2-nitro-phenylamino)-4-phenyl-thiazole-5-carboxylic acid ethyl ester (VI.1b) as an orange oil. The crude was carried to the next step reaction without further purification.

Step 3

A mixture of 0.080 g (0.2 mmole) of 2-(5-formyl-2-nitro-phenylamino)-4-phenyl-thiazole-5-carboxylic acid ethyl ester (VI.1b), 2 mL of dichloromethane and 0.027 mL (0.24 mmole) of 1-methyl-piperizine was stirred at ambient temperature for 10 minutes, then 0.064 g (0.3 mmole) of sodium triacetoxyborohydride was added. The mixture was stirred at ambient temperature for 2 hours and was then diluted with 10 mL of dichloromethane. The mixture was washed with 3 mL of saturated sodium bicarbonate. The aqueous layer was extracted twice with 5 mL of dichloromethane. The combined organic layers were washed with brine, dried over anhydrous magnesium sulfate, filtered and concentrated under reduced pressure. The residue was purified by silica gel chromatography, eluting with methanol-dichloromethane (gradient 0:100-5:95) to give 0.066 g of 2-[5-(4-methyl-piperazin-1-ylmethyl)-2-nitro-phenylamino]-4-phenyl-thiazole-5-carboxylic acid ethyl ester (VI.1c) as an orange solid.

Step 4

To a mixture of 0.066 g of 2-[5-(4-methyl-piperazin-1-ylmethyl)-2-nitro-phenylamino]-4-phenyl-thiazole-5-carboxylic acid ethyl ester (VI.1c), 0.5 mL of 1M hydrochloric acid, 2 mL of tetrahydrofuran was added 0.060 g of zinc powder. The suspension was stirred at ambient temperature for 2 hours. The solid was removed by filtration and the filtrate was concentrated under reduced pressure. The residue was diluted with 2 mL of saturated sodium bicarbonate, 10 mL of water and extracted three times with 5 mL of dichloromethane. The combined organic layers were washed with brine, dried over anhydrous magnesium sulfate, filtered and concentrated under reduced pressure to give 2-[2-amino-5-(4-methyl-piperazin-1-ylmethyl)-phenylamino]-4-phenyl-thiazole-5-carboxylic acid ethyl ester (VII.1a) as a yellow oil. This material was carried to next step of reaction without further purification.

Step 5

To a mixture of 2-[2-amino-5-(4-methyl-piperazin-1-ylmethyl)-phenylamino]-4-phenyl-thiazole-5-carboxylic acid ethyl ester (VII.1a) from previous step and 0.2 mL of acetic acid was added 0.2 mL of triethyl orthoformate. The reaction mixture was heated to 60 degrees for 1 hour, and then concentrated under reduced pressure. The residue was diluted with 10 mL of water and 2 mL of saturated sodium bicarbonate and then extracted three times with 5 mL of dichloromethane. The combined organic layers were washed with brine, dried over anhydrous magnesium sulfate, filtered and concentrated under reduced pressure. The residue was purified by silica gel chromatography eluting with methanol-dichloromethane (gradient 0:100-10:90) to give 0.041 g of 2-[6-(4-methyl-piperazin-1-ylmethyl)-benzoimidazol-1-yl]-4-phenyl-thiazole-5-carboxylic acid ethyl ester (I.1a) as a white solid.

Step 6

To a mixture of 0.041 g (0.089 mmole) of 2-[6-(4-methyl-piperazin-1-ylmethyl)-benzoimidazol-1-yl]-4-phenyl-thiazole-5-carboxylic acid ethyl ester (I.1a), 1 mL of tetrahydrofuran and 1 mL of water was added 0.011 g of lithium hydroxide. The reaction mixture was heated to 60 degrees for 30 minutes and then concentrated under reduced pressure. The mixture was diluted with 5 mL of water and then extracted with 5 mL of ethyl acetate. The pH of the aqueous layer was adjusted to ca 7 by addition of 1M hydrochloric acid and then extracted with 5 mL of ethyl acetate. A precipitate formed in aqueous layer after extraction. The solid was collected by filtration and air dried to give 0.025 g of 2-[6-(4-methyl-piperazin-1-ylmethyl)-benzoimidazol-1-yl]-4-phenyl-thiazole-5-carboxylic acid (I.1b) as an off-white solid.

Step 7

To a mixture of 0.022 g (0.05 mmole) of 2-[6-(4-methyl-piperazin-1-ylmethyl)-benzoimidazol-1-yl]-4-phenyl-thiazole-5-carboxylic acid (I.1b), 0.023 g (0.06 mmole) of 1-[bis(dimethylamino)methylene]-1H-1,2,3-triazolo[4,5-b]pyridinium, 3-oxide, hexafluorophosphate(1-) (1:1), 0.004 g of ammonium chloride and 1 mL of dimethylformamide was added 0.026 mL (0.15 mmole) of ethyldiisopropylamine. The mixture was stirred at ambient temperature for 1 hour. Solids were removed by filtration and the filtrate purified by reverse phase silica gel chromatography, eluting with acetonitrile-water (gradient 10:90-90:10) to give 0.014 g of 2-[6-(4-methyl-piperazin-1-ylmethyl)-benzoimidazol-1-yl]-4-phenyl-thiazole-5-carboxylic acid amide (I.1) as a white powder. MH+/Z=433.

Example 2a 4-(3-Chloro-phenyl)-2-[6-(4-methyl-piperazin-1-ylmethyl)-benzoimidazol-1-yl]-thiazole-5-carboxylic acid amide (I.2)

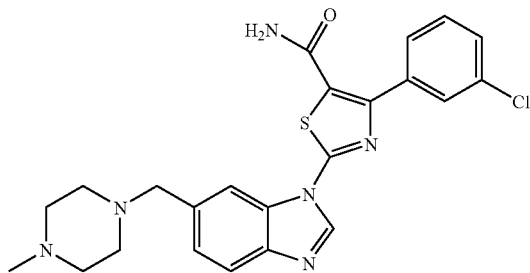

Step 1

A mixture of 0.5 g (2.96 mmole) of 3-fluoro-4-nitrobenzaldehyde, 1 mL of trimethylorthoformate, 0.020 g of p-toluenesulfonic acid monohydrate and 2 mL of methanol was heated at reflux for 1 hour. The mixture was cooled, and 1 mL of saturated aqueous sodium bicarbonate solution was added. The mixture was concentrated under reduced pressure, and the residue was partitioned between 30 mL of ethyl acetate and 30 mL of saturated aqueous sodium bicarbonate solution. The organic layer was washed with brine, dried over anhydrous magnesium sulfate, filtered and concentrated under reduced pressure to give 0.64 g of 4-dimethoxymethyl-2-fluoro-1-nitro-benzene (IV.2a) as a pale yellow oil. This material was used without further purification.

Step 2

A mixture of 2.56 g (11.9 mmole) of 4-dimethoxymethyl-2-fluoro-1-nitro-benzene (IV.2a), 3.00 g (11.85 mmole) of 2-amino-4-(3-chloro-phenyl)-thiazole-5-carboxylic acid amide (V.2), 11.6 g (35.7 mmole) of cesium carbonate and 40 mL of dimethylformamide was stirred at 60 degrees for 3 hours. The mixture was cooled, poured into dilute ammonium chloride solution, and the precipitated yellow solid was collected by filtration, washed with water, and air-dried to give 4.43 g of 4-(3-chloro-phenyl)-2-(5-dimethoxymethyl-2-nitro-phenylamino)-thiazole-5-carboxylic acid amide (VI.2a).

Step 3

A mixture of 4.43 g (9.9 mmole) of 4-(3-chloro-phenyl)-2-(5-dimethoxymethyl-2-nitro-phenylamino)-thiazole-5-carboxylic acid amide (VI.2a), 80 mL of acetonitrile and 20 mL of 1 M hydrochloric acid was heated at 60 degrees for 2 hours. The mixture was diluted with 200 mL of ice-water. The precipitate was collected by filtration, washed with water, and air dried to give 3.3 g of 4-(3-chloro-phenyl)-2-(5-formyl-2-nitro-phenylamino)-thiazole-5-carboxylic acid amide (VI.2b) as an orange solid.

Step 4

To a suspension of the 1.00 g (2.49 mmole) of 4-(3-chloro-phenyl)-2-(5-formyl-2-nitro-phenylamino)-thiazole-5-carboxylic acid amide (VI.2b), 40 mL of saturated aqueous ammonium chloride solution and 40 mL of tetrahydrofuran was added 1 g of zinc powder. The mixture was stirred room temperature for 15 minutes, then another 1 g of zinc powder was added. The mixture was stirred at room temperature for 15 minutes, then 1 g of zinc powder was added, and the mixture was stirred at room temperature for 15 minutes until the organic layer became straw yellow in color. Subsequent manipulations were performed under nitrogen. The mixture was filtered, and the filtrate was partitioned between 30 mL of saturated ammonium chloride solution and tetrahydrofuran (1:1). The organic layer was separated, dried over anhydrous magnesium sulfate, filtered and concentrated under reduced pressure to give a reddish yellow solid. The solid was mixed with 40 mL of acetic acid and 0.82 ml, (4.98 mmole) of triethyl orthoformate, and the mixture was stirred at room temperature for 30 minutes, during which time the mixture became mostly homogeneous. The mixture was filtered and the filtrate was poured into 200 mL of water. The precipitate was collected by filtration, washed with water and air-dried to give 0.73 g of 4-(3-chloro-phenyl)-2-(6-formyl-benzoimidazol-1-yl)-thiazole-5-carboxylic acid amide (I.2a) as a pink solid.

Step 5

A mixture of 0.15 g (0.39 mmole) of 4-(3-chloro-phenyl)-2-(6-formyl-benzoimidazol-1-yl)-thiazole-5-carboxylic acid amide (I.2a), 0.078 g (0.78 mmole) of N-methylpiperazine, 0.411 g (0.195 mmole) of sodium triacetoxyborohydride and 5 mL of dichloromethane was stirred at room temperature for 24 hours, after which 1 mL of saturated aqueous ammonium chloride solution was added. The mixture was stirred at room temperature for 30 minutes, made basic by addition of saturated potassium carbonate solution and partitioned between 30 mL of dichloromethane and 30 mL of dilute potassium carbonate solution. The aqueous layer was extracted twice with 30 mL of dichloromethane. The combined dichloromethane layers were washed with brine, dried over anhydrous magnesium sulfate, filtered and concentrated under reduced pressure. The residue was purified by silica gel chromatography, eluting with methanol-dichloromethane (20:80) to give 0.070 g of a yellow solid. Further purification by SFC (methanol) gave 0.056 g of 4-(3-chloro-phenyl)-2-[6-(4-methyl-piperazin-1-ylmethyl)-benzoimidazol-1-yl]-thiazole-5-carboxylic acid amide (I.2) as a yellow solid. MH+/Z=467.

Example 2b

Method 1

4-(3-Chloro-phenyl)-2-[6-(4-methyl-piperazin-1-ylmethyl)-benzoimidazol-1-yl]-thiazole-5-carboxylic acid amide (I.2)

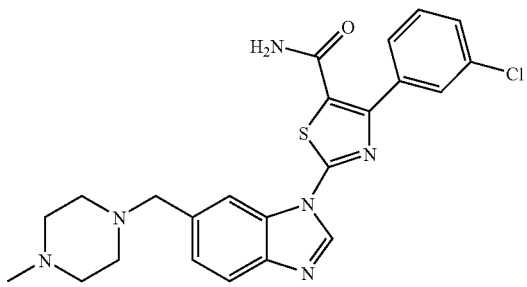

Step 1

To a solution of 0.0292 g (0.2 mmole) of 3H-benzoimidazole-5-carbaldehyde (II.2) and 1 mL of dimethylformamide at 0 degrees was added 0.012 g (0.3 mmole) of sodium hydride. After gas evolution ceased, 0.0604 g (0.2 mmole) of 2-chloro-4-(3-chloro-phenyl)-thiazole-5-carboxylic acid ethyl ester (III.2) was added. The resulting solution was stirred at ambient temperature for 1 hour and then quenched by the addition of 10 mL of water. The mixture was extracted three times with 5 mL of ethyl acetate. The combined organic layers were washed with brine, dried over anhydrous magnesium sulfate, filtered and concentrated under reduced pressure. The residue was purified by silica gel chromatography, eluting with methanol-dichloromethane (gradient 0:100-2:98) to 0.052 g of a mixture of 4-(3-chloro-phenyl)-2-(6-formyl-benzoimidazol-1-yl)-thiazole-5-carboxylic acid ethyl ester (I.2b) and 4-(3-chloro-phenyl)-2-(5-formyl-benzoimidazol-1-yl)-thiazole-5-carboxylic acid ethyl ester (I.2c) as a white solid.

Step 2

To 0.750 g (1.8 mmole) of the mixture of 4-(3-chloro-phenyl)-2-(6-formyl-benzoimidazol-1-yl)-thiazole-5-carboxylic acid ethyl ester (I.2b) and 4-(3-chloro-phenyl)-2-(5-formyl-benzoimidazol-1-yl)-thiazole-5-carboxylic acid ethyl ester (I.2c) and 20 mL of dichloromethane was added 0.22 mL (1.98 mmole) of 1-methyl-piperazine. The mixture was stirred at ambient temperature for 20 minutes, then 0.572 g (2.7 mmole) of sodium triacetoxyborohydride was added. The resulting suspension was stirred for 3 hours and then quenched by addition of 30 ml of water. The mixture was extracted twice with 20 mL dichloromethane. The combined organic layers were washed with brine, dried over anhydrous magnesium sulfate, filtered and concentrated under reduced pressure. The residue was purified by silica gel chromatography, eluting with methanol-dichloromethane (gradient 0:100-8:92) to give (first eluting component) 0.30 g of 4-(3-chloro-phenyl)-2-[6-(4-methyl-piperazin-1-ylmethyl)-benzoimidazol-1-yl]-thiazole-5-carboxylic acid ethyl ester (I.2d) and (second eluting component) 0.31 g of 4-(3-chloro-phenyl)-2-[5-(4-methyl-piperazin-1-ylmethyl)-benzoimidazol-1-yl]-thiazole-5-carboxylic acid ethyl ester (I.2e).

Step 3

To a solution of 0.250 g (0.5 mmole) of 4-(3-chloro-phenyl)-2-[6-(4-methyl-piperazin-1-ylmethyl)-benzoimidazol-1-yl]-thiazole-5-carboxylic acid ethyl ester (I.2d) in 10 mL of tetrahydrofuran and 10 mL of water was added 0.12 g (5 mmole) of lithium hydroxide. The mixture was stirred at ambient temperature for 1 hour. The mixture was concentrated under reduced pressure, 40 mL of water was added and the pH adjusted to 6-7 by the addition of 1M hydrochloric acid. The precipitate was collected by filtration to give 0.145 g of 4-(3-chloro-phenyl)-2-[6-(4-methyl-piperazin-1-ylmethyl)-benzoimidazol-1-yl]-thiazole-5 carboxylic acid (I.2f) as a white solid.

Step 4

To a mixture of 0.048 g (0.1 mmole) of 4-(3-chloro-phenyl)-2-[6-(4-methyl-piperazin-1-ylmethyl)-benzoimidazol-1-yl]-thiazole-5-carboxylic acid, 0.046 g (0.12 mmole) of 1-[bis(dimethylamino)methylene]-1H-1,2,3-triazolo[4,5-b]pyridinium, 3-oxide, hexafluorophosphate(1-) (1:1), 0.008 g (0.15 mmole) of ammonium chloride and 1 mL of dimethylformamide was added 0.052 mL of diisopropylethylamine. The mixture was stirred at ambient temperature for 1 hour, filtered and then purified by reverse phase silica gel chromatography, eluting with acetonitrile-water (gradient 10:90-90:10) to give 0.027 g of 4-(3-chloro-phenyl)-2-[6-(4-methyl-piperazin-1-ylmethyl)-benzoimidazol-1-yl]-thiazole-5-carboxylic acid amide (I.2) as a white solid. MH+/Z=467

Example 3

4-(3-Chloro-phenyl)-2-[5-(4-methyl-piperazin-1-ylmethyl)-benzoimidazol-1-yl]-thiazole-5-carboxylic acid amide (I.3)

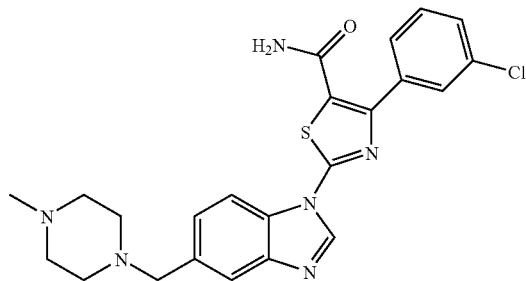

Step 1

To a solution of 0.25 g (0.5 mmole) of 4-(3-chloro-phenyl)-2-[5-(4-methyl-piperazin-1-ylmethyl)-benzoimidazol-1-yl]-thiazole-5-carboxylic acid ethyl ester (I.2e) in 10 mL of tetrahydrofuran and 10 mL of water was added 0.12 g (5 mmole) of lithium hydroxide. The mixture was stirred at ambient temperature for 1 hour. The mixture was concentrated under reduced pressure, 40 mL of water was added and the pH adjusted to 6-7 by the addition of 1M hydrochloric acid. The precipitate was collected by filtration to give 0.120 g of 4-(3-chloro-phenyl)-2-[5-(4-methyl-piperazin-1-ylmethyl)-benzoimidazol-1-yl]-thiazole-5-carboxylic acid (I.3a) as a white solid.

Step 2

To a mixture of 0.048 g (0.1 mmole) of 4-(3-chloro-phenyl)-2-[5-(4-methyl-piperazin-1-ylmethyl)-benzoimidazol-1-yl]-thiazole-5-carboxylic acid (I.3a), 0.046 g (0.12 mmole) of 1-[bis(dimethylamino)methylene]-1H-1,2,3-triazolo[4,5-b]pyridinium, 3-oxide, hexafluorophosphate(1-) (1:1), 0.008 g (0.15 mmole) of ammonium chloride and 1 mL of dimethylformamide was added 0.052 mL (0.3 mmole) of diisopropylethylamine. The mixture was stirred at ambient temperature for 1 hour, then filtered and purified by reverse phase silica gel chromatography, eluting with acetonitrile-water (gradient 10:90-90:10) to give 0.030 g of 4-(3-chloro-phenyl)-2-[5-(4-methyl-piperazin-1-ylmethyl)-benzoimidazol-1-yl]-thiazole-5-carboxylic acid amide (I.3) as a white powder. MH+/Z=467

Example 4

4-(3-Chloro-phenyl)-2-(6-morpholin-4-ylmethyl-benzoimidazol-1-yl)-thiazole-5-carboxylic acid amide (I.4)

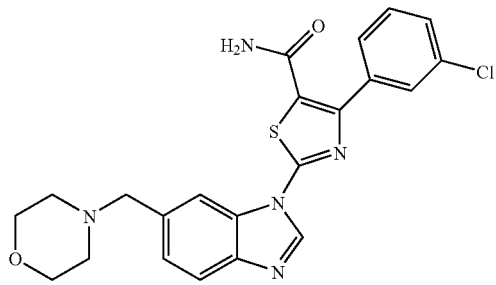

Step 1

A mixture of 0.037 g (0.099 mmole) of 4-(3-chloro-phenyl)-2-(6-formyl-benzoimidazol-1-yl)-thiazole-5-carboxylic acid amide (I.2a), 0.063 g (0.30 mmole) of morpholine, 0.030 g (0.34 mmole) of sodium triacetoxyborohydride and 5 mL of dichloromethane was stirred at room temperature for 24 hours, after which 1 mL of saturated aqueous ammonium chloride solution was added. The mixture was stirred at room temperature for 30 minutes, made basic by addition of saturated potassium carbonate solution and partitioned between 30 mL of dichloromethane and 30 mL of dilute potassium carbonate solution. The aqueous layer was extracted twice with 30 mL of dichloromethane. The combined dichloromethane layers were washed with brine, dried over anhydrous magnesium sulfate, filtered and concentrated under reduced pressure. The residue was purified by silica gel chromatography, eluting with methanol-dichloromethane (5:95) to give 0.027 g of a pink solid. Further purification by SFC (methanol) gave 0.020 g of 4-(3-chloro-phenyl)-2-(6-morpholin-4-ylmethyl-benzoimidazol-1-yl)-thiazole-5-carboxylic acid amide (I.4) as a white solid. MH+/Z=454

Example 5

4-(3-Chloro-phenyl)-2-{6-[4-(2-hydroxy-ethyl)-piperazin-1-ylmethyl]-benzoimidazol-1-yl}-thiazole-5-carboxylic acid amide (I.5)

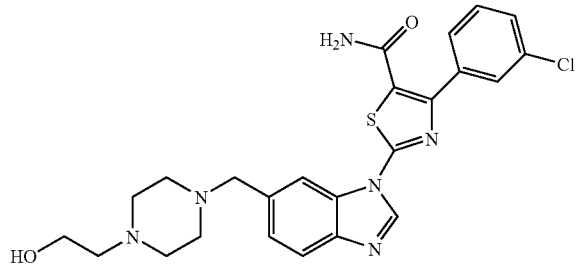

A mixture of 0.050 g (0.13 mmole) of 4-(3-chloro-phenyl)-2-(6-formyl-benzoimidazol-1-yl)-thiazole-5-carboxylic acid amide (I.2a), 0.026 g (0.20 mmole) of N-2-hydroxyethylpiperazine, 0.137 g (0.65 mmole) of sodium triacetoxyborohydride and 5 mL of dichloromethane was stirred at room temperature for 24 hours, after which 1 mL of saturated aqueous ammonium chloride solution was added. The mixture was stirred at room temperature for 30 minutes, made basic by addition of saturated potassium carbonate solution and partitioned between 30 mL of dichloromethane and 30 mL of dilute potassium carbonate solution. The aqueous layer was extracted twice with 30 mL of dichloromethane. The combined dichloromethane layers were washed with brine, dried over anhydrous magnesium sulfate, filtered and concentrated under reduced pressure. The residue was purified by silica gel chromatography, eluting with methanol-dichloromethane-ammonium:hydroxide (10:90:2) to give 0.044 g of a pink solid. Further purification by SFC (methanol) gave 0.032 g of 4-(3-chloro-phenyl)-2-{6-[4-(2-hydroxy-ethyl)-piperazin-1-ylmethyl]-benzoimidazol-1-yl}thiazole-5-carboxylic acid amide (I.5) as an off-white solid. MH+/Z=497

Example 6

4-(3-Chloro-phenyl)-2-(6-{[(2-dimethylamino-ethyl)-methyl-amino]-methyl}-benzoimidazol-1-yl)-thiazole-5-carboxylic acid amide (I.6)

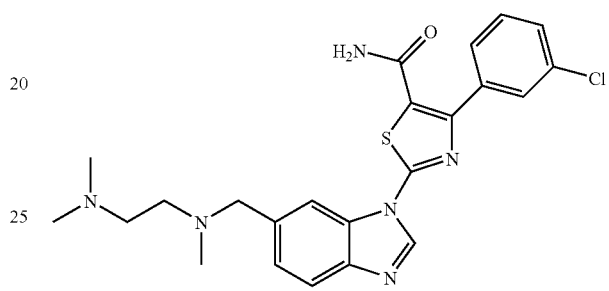

A mixture of 0.065 g (0.17 mmole) of 4-(3-chloro-phenyl)-2-(6-formyl-benzoimidazol-1-yl)-thiazole-5-carboxylic acid amide (I.2a), 0.060 mL of N,N,N'-trimethyl-ethane-1,2-diamine, 0.10 g of sodium triacetoxyborohydride and 5 mL of dichloromethane was stirred at room temperature for 6 hours, after which 1 mL of saturated aqueous ammonium chloride solution was added. The mixture was stirred at room temperature for 30 minutes, made basic by addition of saturated potassium carbonate solution and partitioned between 30 mL of dichloromethane and 30 mL of dilute potassium carbonate solution. The aqueous layer was extracted twice with 30 mL of dichloromethane. The combined dichloromethane layers were washed with brine, dried over anhydrous magnesium sulfate, filtered and concentrated under reduced pressure. The residue was purified by silica gel chromatography, eluting with methanol-dichloromethane-ammonium:hydroxide (10:90:1) to give 0.041 g of 4-(3-chloro-phenyl)-2-(6-{[(2-dimethylamino-ethyl)-methyl-amino]-methyl}-benzoimidazol-1yl)-thiazole-5-carboxylic acid amide (I.6) as a light pink solid. MH+/Z=469

Example 7

4-(3-Chloro-phenyl)-2-{6-[(1-methyl-piperidin-4-ylamino)-methyl]-benzoimidazol-1-yl}-thiazole-5-carboxylic acid amide (I.7)

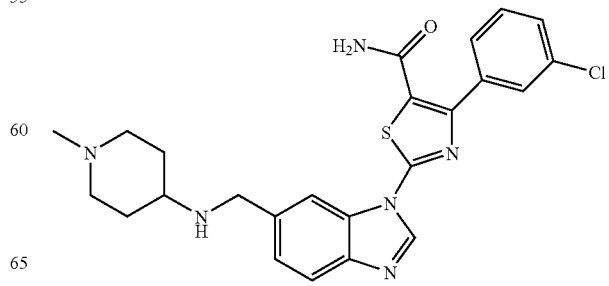

A mixture of 0.060 g (0.15 mmole) of 4-(3-chloro-phenyl)-2-(6-formyl-benzoimidazol-1-yl)-thiazole-5-carboxylic acid amide (I.2a), 0.060 mL of 4-aminopiperidine and 5 mL of methanol was heated at reflux for 1 hour. The mixture was cooled and concentrated under reduced pressure to give 4-(3-chloro-phenyl)(6{[(E/Z)-1-methyl-piperidin-4-ylimino]-methyl}-benzoimidazol-1-yl)-thiazole-5-carboxylic acid amide. The crude imine was dissolved in 10 mL of methanol at room temperature and 0.060 g of sodium borohydride was added. The mixture was stirred at room temperature for 1 hour. The mixture was concentrated under reduced pressure and mixed with 15 mL of 1 M hydrochloric acid and extracted twice with 15 mL of ethyl acetate. The aqueous layer was made basic by addition of potassium carbonate and extracted three times with 15 mL of dichloromethane. The combined organic extracts were dried over anhydrous sodium sulfate, filtered and concentrated under reduced pressure. The residue was dissolved in 10 mL of methanol and then 0.040 mL of acetyl chloride (40 uL) was added dropwise. The mixture was concentrated under reduced pressure. The residue was triturated with ethyl acetate and the solid was collected by filtration and washed with ethyl acetate. The solid was dissolved in 40 mL of water and made basic by addition of potassium carbonate. The mixture was extracted three times with 20 mL of dichloromethane. The combined organic layers were dried over anhydrous sodium sulfate, filtered and concentrated under reduced pressure to give an oil. The oil was triturated with methanol and acetonitrile to give 0.036 g of 4-(3-chloro-phenyl)-2-{6-[(1-methyl-piperidin-4-ylamino)-methyl]-benzoimidazol-1-yl}thiazole-5-carboxylic acid amide (I.7) as a light pink solid. MH+/Z=481

Example 8

4-(3-Chloro-phenyl)-2-(6-piperidin-1-ylmethyl-benzoimidazol-1-yl)-thiazole-5-carboxylic acid amide (I.8)

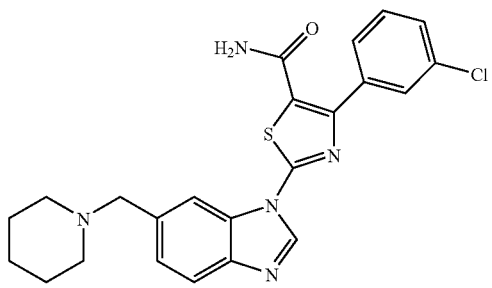

A mixture of 0.150 g (0.39 mmole) of 4-(3-chloro-phenyl)-2-(6-formyl-benzoimidazol-1-yl)-thiazole-5-carboxylic acid amide (I.2a), 0.078 mL of piperidine, 0.414 g of sodium triacetoxyborohydride and 5 mL of dichloromethane was stirred at room temperature for 24 hours, after which 1 mL of saturated aqueous ammonium chloride solution was added. The mixture was stirred at room temperature for 30 minutes, made basic by addition of saturated potassium carbonate solution and partitioned between 30 mL of dichloromethane and 30 mL of dilute potassium carbonate solution. The aqueous layer was extracted twice with 30 mL of dichloromethane. The combined dichloromethane layers were washed with brine, dried over anhydrous magnesium sulfate, filtered and concentrated under reduced pressure. The residue was triturated with dichloromethane to give a pink solid.

Further purification by SFC (methanol) gave 0.050 g of 4-(3-chloro-phenyl)-2-(6-piperidin-1-ylmethyl-benzoimidazol-1-yl)-thiazole-5-carboxylic acid amide (I.8) as a yellow solid. MH+/Z=452

Example 9

4-(3-Chloro-phenyl)-2-{6-[2-(4-methyl-piperazin-1-yl)-ethyl]-benzoimidazol-1-yl}-thiazole-5-carboxylic acid amide (I.9)

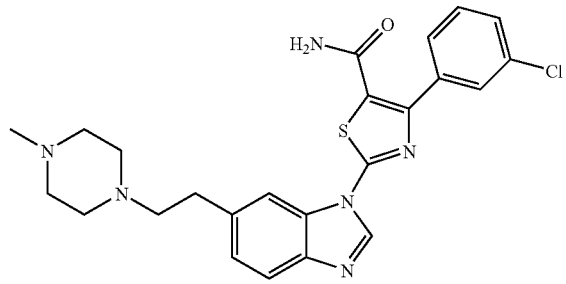

Step 1

A mixture of 0.155 g (1 mmole) of 2-fluoro-4-methyl-1-nitro-benzene, 1 mL of N,N-dimethylformamide dimethylacetal and 3 mL of dimethylformamide (3 mL) was heated in an oil bath at 125 degrees for 1 hour. The mixture was cooled and concentrated under reduced pressure to give a purple solid. Trituration with hexanes gave 0.115 g of [(E/Z)-2-(3-fluoro-4-nitro-phenyl)-vinyl]-dimethylamine (IV.9a) as a purple solid.

Step 2

A mixture of 0.115 g of [(E/Z)-2-(3-fluoro-4-nitro-phenyl)-vinyl]-dimethylamine (IV.9a), 0.105 g (0.55 mmole) of p-toluenesulfonic acid monohydrate and 5 mL of methanol was heated at reflux for 3 hours. The mixture was cooled and concentrated under reduced pressure. The residue was partitioned between 30 mL of ethyl acetate and saturated 30 mL of sodium bicarbonate solution. The aqueous layer was extracted three times with 20 mL of ethyl acetate. The combined organic layers were washed with brine, dried over anhydrous magnesium sulfate, filtered and concentrated under reduced pressure to give 0.110 g of 4-(2,2-dimethoxy-ethyl)-2-fluoro-1-nitro-benzene (IV.9b) as an orange oil.

Step 3

A mixture of 0.625 g (2.73 mmole) of 4-(2,2-dimethoxy-ethyl)-2-fluoro-1-nitro-benzene (IV.9b), 0.630 g (2.73 mmole) of 2-amino-4-(3-chloro-phenyl)-thiazole-5-carboxylic acid amide (V.2), 2.66 g (8.2 mmole) of cesium carbonate and 10 mL of dimethylformamide was stirred at 60 degrees for 3 hours. The mixture was cooled, poured into 50 mL of dilute ammonium chloride solution. The resulting suspension was extracted three times with 20 mL of ethyl acetate. The combined organic layers were washed three times with 20 mL of water, once with 20 mL of brine, dried over anhydrous magnesium sulfate, filtered and concentrated under reduced pressure. The residue was triturated with diethyl ether to give 0.650 g of 4-(3-chloro-phenyl)-2-[5(2,2-dimethoxy-ethyl)-2-nitro-phenylamino]-thiazole-5-carboxylic acid amide (VI.9a) as an orange solid.

Step 4

A mixture of 0.200 g (0.43 mmole) of 4-(3-chloro-phenyl)-2-[5(2,2-dimethoxy-ethyl)-2-nitro-phenylamino]-thiazole-5-carboxylic acid amide (VI.9a) and 3 mL of 96% formic acid was stirred at room temperature for 1 hour. The solution was poured into water and the resulting precipitate was collected by filtration, washed with water and air-dried to give 0.135 g of 4-(3-chloro-phenyl)-2-[2-nitro-5-(2-oxo-ethyl)-phenylamino]-thiazole-5-carboxylic acid amide (VI.9b) as an orange solid. A mixture of 0.135 g of 4-(3-chloro-phenyl)-2-[2-nitro-5-(2-oxo-ethyl)-phenylamino]-thiazole-5-carboxylic acid amide (VI.9b), 0.10 mL of N-methylpiperazine, 0.10 mL of glacial acetic acid, 0.50 g of sodium triacetoxyborohydride and 10 mL of dichloromethane was stirred at room temperature for 16 hours. To the mixture was carefully added 1 mL of 1M hydrochloric acid and stirring was continued at room temperature for 30 minutes. The mixture was partitioned between 30 mL of dichloromethane and 30 mL of saturated aqueous sodium bicarbonate solution. The organic layer was washed once with 30 mL of water, then 30 mL of brine, dried over anhydrous sodium sulfate, filtered and concentrated under reduced pressure. The residue was purified by silica gel chromatography, eluting with methanol-dichloromethane (gradient 15:85-20:80) to give an orange foam. Trituration with diethyl ether gave 0.100 g of 4-(3-chlorophenyl)-2-{5-[2-(4-methyl-piperazin-1-yl)-ethyl]-2-nitro-phenylamino}-thiazole-5-carboxylic acid amide (VI.9c) as an orange solid.

Step 5

A mixture of 0.100 g (0.20 mmole) of 4-(3-chlorophenyl)-2-{5-[2-(4-methyl-piperazin-1-yl)-ethyl]-2-nitro-phenylamino}-thiazole-5-carboxylic acid amide (VI.9c), 0.10 g of 10% Pd—C catalyst and 3 mL of 96% formic acid was stirred under 1 atmosphere of hydrogen for 16 hours. The mixture was filtered through diatomaceous earth and the filtrate was concentrated under reduced pressure. The residue was dissolved in 1 mL of 96% formic acid and heated in an oil bath at 60 degrees for 30 minutes. The cooled mixture was concentrated under reduced pressure and the residue was partitioned between 30 mL of dichloromethane and 30 mL of saturated sodium bicarbonate solution. The aqueous layer was extracted three times with 20 mL of dichloromethane. The combined organic layers were washed with 30 mL of brine, dried over anhydrous sodium sulfate, filtered and concentrated under reduced pressure to give 0.049 g of an off-white solid. Purification by SFC (methanol, triethylamine) gave 0.028 g of 4-(3-chloro-phenyl)-2-{6-[2-(4-methyl-piperazin-1-yl)-ethyl]-benzoimidazol-1-yl}-thiazole-5-carboxylic acid amide (I.9) as an off-white solid. MH+/Z=481

Example 10

3-[5-Carbamoyl-4-(3-chloro-phenyl)-thiazol-2-yl]-3H-benzoimidazole-5-carboxylic acid (1-methyl-piperidin-4-yl)-amide (I.10)

Step 1

A mixture of 0.222 g (1.2 mmole) of 3-fluoro-4-nitrobenzoic acid, 0.30 g (1.2 mmole) of 2-amino-4-(3-chloro-phenyl)-thiazole-5-carboxylic acid amide (V.2), 1.5 g (4.6 mmole) of cesium carbonate and 40 mL of dimethylformamide was stirred at 60 degrees for 16 hours. The mixture was cooled and poured into water. The dark mixture was made acidic by addition of hydrochloric acid, and the resulting orange precipitate was collected by filtration, washing, water to give 0.281 g of 3-[5-carbamoyl-4-(3-chloro-phenyl)-thiazol-2-ylamino]-4-nitro-benzoic acid (VI.10).

Step 2

A mixture of 0.280 g (0.67 mmole) of 3-[5-carbamoyl-4-(3-chloro-phenyl)-thiazol-2-ylamino]-4-nitro-benzoic acid (VI.10), 0.20 g of 10% palladium on carbon catalyst and 3 mL of 96% formic acid was stirred under an atmosphere of hydrogen at room temperature for 16 hours. The mixture was filtered through Diatomaceous earth and the Diatomaceous earth pad was washed with formic acid. The filtrate was concentrated under reduced pressure and the residue was dissolved in 1 mL of tetrahydrofuran and then added dropwise to 50 mL of water. The solid was collected by filtration, washing with water, to give 0.163 g of 3-[5-carbamoyl-4-(3-chloro-phenyl)-thiazol-2-yl]-3H-benzoimidazole-5-carboxylic acid (I.10a).

Step 3

A mixture of 0.060 g (0.15 mmole) of 3-[5-carbamoyl-4-(3-chloro-phenyl)-thiazol-2-yl]-3H-benzoimidazole-5-carboxylic acid (I.10a), 0.06 mL of 4-aminopiperidine, 0.070 g (0.18 mmole) of 1-[bis(dimethylamino)methylene]-1H-1,2,3-triazolo[4,5-b]pyridinium, 3-oxide, hexafluorophosphate (1-) (1:1) and 4 mL of dimethylformamide was stirred at room temperature for 16 hours. The mixture was poured into 50 mL of water and extracted three times with 25 mL of ethyl acetate. The combined organic extracts were washed three times with 20 mL of 1 M hydrochloric acid. The combined aqueous extracts were made basic with potassium carbonate, and the resulting solid collected by filtration, washed with water, and air-dried to give 0.038 g of 3-[5-carbamoyl-4-(3-chloro-phenyl)-thiazol-2-yl]-3H-benzoimidazole-5-carboxylic acid (1-methyl-piperidin-4-yl)-amide (I.10) as a light yellow solid. MH+/Z=495

Example 11

4-(3-Chloro-phenyl)-2-[6-(4-methyl-piperazine-1-carbonyl)-benzoimidazol-1-yl]-thiazole-5-carboxylic acid amide (I.11)

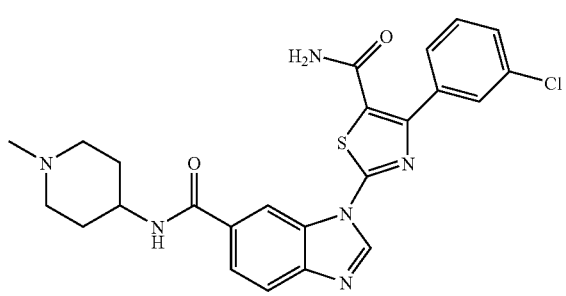

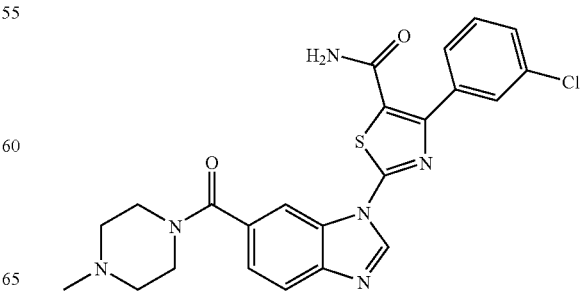

A mixture of 0.05 g (0.15 mmole) of 3-[5-Carbamoyl-4-(3-chloro-phenyl)-thiazol-2-yl]-3H-benzoimidazole-5-carboxylic acid (I.10a), 0.050 mL of N-methyl-piperazine, 0.070 g (0.18 mmole) of 1-[bis(dimethylamino)methylene]-1H-1,2,3-triazolo[4,5-b]pyridinium, 3-oxide, hexafluorophosphate(1-) (1:1) and 4 mL of dimethylformamide was stirred at room temperature for 16 hours. The mixture was poured into 50 mL of water and made acidic by addition of 1 M hydrochloric acid. The aqueous layer was extracted three times with 20 mL of ethyl acetate and then made basic by addition of potassium carbonate solution. The mixture was extracted three times with 20 ml of ethyl acetate. The combined organic extracts were washed with 20 mL of water, 20 mL of brine, dried over anhydrous magnesium sulfate, filtered and concentrated under reduced pressure. The residue was purified by silica gel chromatography, eluting with methanol-dichloromethane (7:93) to give 0.021 g of 4-(3-chloro-phenyl)-2-[6-(4-methyl-piperazine-1-carbonyl)-benzoimidazol-1-yl]-thiazole-5-carboxylic acid amide (I.11) as a yellow solid. MH+/Z=481

Example 12

1-{3-[5-Carbamoyl-4-(3-chloro-phenyl)-thiazol-2-yl]-3H-benzoimidazol-5-ylmethyl}-piperidin-4-yl)-carbamic acid tert-butyl ester (I.12)

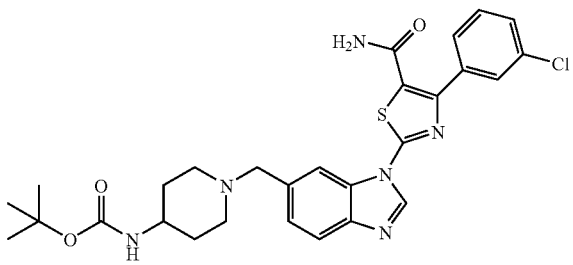

Step 1

A mixture of 3.6 g (15 mmole) of 2-amino-4-(3-chloro-phenyl)-thiazole-5-carboxylic acid amide (V.2), 3.9 g (17.9 mmole) of 4-(dimethoxymethyl)-2-fluoro-1-nitro-benzene (IV.2a), 7.3 g (22.5 mmole) cesium carbonate, and 30 mL of dimethylformamide was heated at 70 degrees for 18 hours. The mixture was cooled, diluted with 150 mL of ethyl acetate and 100 mL of water. The ethyl acetate layer was washed once with 100 mL of brine and dried over anhydrous sodium sulfate. The mixture was filtered and concentrated under reduced pressure. The residue was purified by silica gel chromatography, eluting with hexanes-ethyl acetate (50:50) to give 3.2 g of 4-(3-chloro-phenyl)-2-(5-dimethoxymethyl-2-nitro-phenylamino)-thiazole-5-carboxylic acid amide (VI.2a).

Step 2

A mixture of 3.2 g (7.1 mmole) of 4-(3-chloro-phenyl)-2-(5-dimethoxymethyl-2-nitro-phenylamino)-thiazole-5-carboxylic acid amide (VI.2a), 30 mL of 2M hydrochloric acid and 5 mL of dimethylformamide was stirred at 60 degrees for 3 hours. The mixture was cooled and then concentrated under reduced pressure. The residue was taken up in 100 mL of dichloromethane and washed once with 100 mL of saturated sodium bicarbonate solution, once with 50 mL of brine, and then dried over anhydrous sodium sulfate. The mixture was filtered and concentrated under reduced pressure. The residue was purified by silica gel chromatography, eluting with hexanes-ethyl acetate (50:50) to give 2.5 g of 4-(3-chloro-phenyl)-2-(5-formyl-2-nitro-phenylamino)-thiazole-5-carboxylic acid amide (VI.2b).

Step 3

To a mixture of 0.6 g (1.5 mmole) of 4-(3-chloro-phenyl)-2-(5-formyl-2-nitro-phenylamino)-thiazole-5-carboxylic acid amide (VI.2b) and 0.328 g (1.6 mmole) of piperidin-4-yl-carbamic acid tert-butyl ester in 15 mL of dichloromethane was added 0.477 g (2.3 mmole) of sodium cyanoborohydride. The mixture was stirred for 3 hours, then quenched by the addition of 25 ml of water. The mixture was extracted three times with 50 mL of ethyl acetate. The combined ethyl acetate layers were washed once with 50 mL of brine, dried over anhydrous sodium sulfate, filtered and concentrated under reduced pressure. The residue was purified by silica gel chromatography, eluting with dichloromethane-methanol (gradient 100:0-80:20) to give 0.7 g of (1-{3-[5-carbamoyl-4-(3-chloro-phenyl)-thiazol-2-ylamino]-4-nitro-benzyl}-piperidin-4-yl)-carbamic acid tert-butyl ester (VI.12a).

Step 4

To a suspension of 0.250 g of (1-{3-[5-carbamoyl-4-(3-chloro-phenyl)-thiazol-2-ylamino]-4-nitro-benzyl}-piperidin-4-yl)-carbamic acid tert-butyl ester (VI.12a), 10 mL of tetrahydrofuran, and 10 mL of saturated ammonium chloride solution was added 0.15 g (6.9 mg-atom) of zinc powder. After 15 minutes, another 0.15 g of zinc powder was added. The mixture was stirred for another 10 minutes, then 0.15 g of zinc powder was added. The mixture was filtered, and 30 mL of saturated ammonium chloride solution plus 30 mL of tetrahydrofuran were added to the filtrate. The tetrahydrofuran layer was dried over anhydrous sodium sulfate, filtered and concentrated under reduced pressure to give 0.23 g of (1-{4-amino-3-[5-carbamoyl-4-(3-chloro-phenyl)-thiazol-2-ylamino]-benzyl}-piperidin-4-yl)-carbamic acid tert-butyl ester (VII.12), which was used directly in the next step.

Step 5

A mixture of 0.23 g (0.41 mmole) of (1-{4-amino-3-[5-carbamoyl-4-(3-chloro-phenyl)-thiazol-2-ylamino]-benzyl}-piperidin-4-yl)-carbamic acid tert-butyl ester (VII.12), 0.303 g (2.05 mmole) of triethyl orthoformate and 10 mL of acetic acid was stirred at room temperature for one hour. The mixture was concentrated under reduced pressure. The residue was taken up in 100 mL of dichloromethane, and washed with 100 mL of saturated sodium bicarbonate, then 100 mL of brine, dried over anhydrous sodium sulfate, filtered and concentrated under reduced pressure. The residue was purified by silica gel chromatography, eluting with dichloromethane-methanol (gradient 100:0-90:10) to give 0.180 g of 1-{3-[5-carbamoyl-4-(3-chloro-phenyl)-thiazol-2-yl]-3H-benzoimidazol-5-ylmethyl}-piperidin-4-yl)-carbamic acid tert-butyl ester (I.12) as an off white solid. MH+/Z=567

Example 13

2-[6-(4-Amino-piperidin-1-ylmethyl)-benzoimidazol-1-yl]-4-(3-chloro-phenyl)-thiazole-5-carboxylic acid amide (I.13)

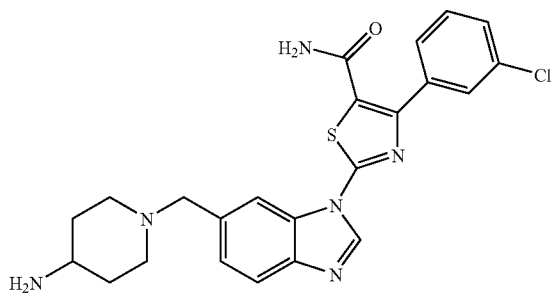

A mixture of 0.145 g of 1-{3-[5-carbamoyl-4-(3-chloro-phenyl)-thiazol-2-yl]-3H-benzoimidazol-5-ylmethyl}-piperidin-4-yl)-carbamic acid tert-butyl ester (I.12), 15 mL of dichloromethane and 1 mL of trifluoroacetic acid was stirred for 2 hours and then concentrated under reduced pressure. The residue was treated with 25 mL of saturated sodium bicarbonate, and extracted three times with 50 mL of dichloromethane. The combined organic layers were washed once with 50 mL of brine, dried over anhydrous sodium sulfate, filtered and concentrated under reduced pressure. The residue was purified by silica gel chromatography, eluting with dichloromethane-methanol (gradient 100:0-80:20) to give 0.10 g of 2-[6-(4-amino-piperidin-1-ylmethyl)-benzoimidazol-1-yl]-4-(3-chloro-phenyl)-thiazole-5-carboxylic acid amide (I.13) as an off white solid. MH+/Z=467

Example 14

1-Methyl-piperidine-4-carboxylic acid (1-{3-[5-carbamoyl-4-(3-chloro-phenyl)-thiazol-2-yl]3H-benzoimidazol-5-ylmethyl}-piperidin-4-yl)-amide (I.14)

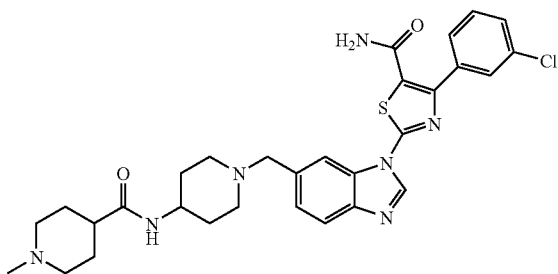

A mixture of 0.120 g (0.26 mmole) of 2-[6-(4-amino-piperidin-1-ylmethyl)-benzoimidazol-1-yl]-4-(3-chloro-phenyl)-thiazole-5-carboxylic acid amide (I.13), 5 mL of dimethylformamide, 0.148 g (0.39 mmole) of 1-[bis(dimethylamino)methylene]-1H-1,2,3-triazolo[4,5-b]pyridinium, 3-oxide, hexafluorophosphate(1-) (1:1), 0.105 g (0.39 mmole) of triethylamine was stirred for 15 minutes, then 0.056 g (0.39 mmole) of 1-methyl-piperidine-4-carboxylic acid was added. After 3 hours, the mixture was taken up in 100 mL of ethyl acetate, washed twice with 100 mL of water, and then once with 100 mL of brine. The ethyl acetate layer was dried over anhydrous sodium sulfate, filtered and concentrated under reduced pressure. The residue was purified by silica gel chromatography, eluting with dichloromethane-(methanol-ammonium hydroxide, (92.8:0.3)) (gradient 100:0-0:100) to give 1-methyl-piperidine-4-carboxylic acid (1-{3-[5-carbamoyl-4-(3-chloro-phenyl)-thiazol-2-yl]3H-benzoimidazol-5-ylmethyl}-piperidin-4-yl)-amide (I.14). This material was taken up in 20 mL of dichloromethane, washed with 20 mL of 1M sodium hydroxide solution. The dichloromethane layer was dried over anhydrous sodium sulfate, filtered and concentrated under reduced pressure to give 0.065 g of 1-methyl-piperidine-4-carboxylic acid (1-{3-[5-carbamoyl-4-(3-chloro-phenyl)-thiazol-2-yl]-3H-benzoimidazol-5-ylmethyl}-piperidin-4-yl)-amide (I.14) as a solid. MH+/Z=592

Example 15

[1-(1-{3-[5-Carbamoyl-4-(3-chloro-phenyl)-thiazol-2-yl]-3H-benzoimidazol-5-ylmethyl}-piperidin-4-ylcarbamoyl)-1-methyl-ethyl]-carbamic acid tert-butyl ester (I.15)

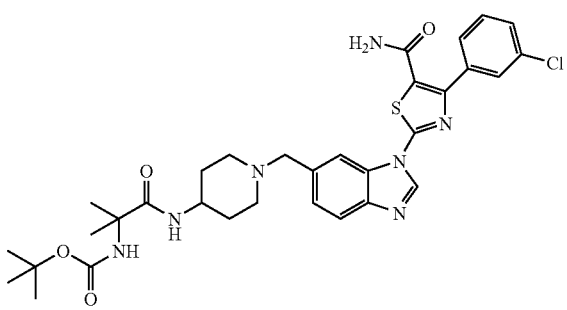

A mixture of 0.360 g (0.77 mmole) of 2-[6-(4-amino-piperidin-1-ylmethyl)-benzoimidazol-1-yl]-4-(3-chloro-phenyl)-thiazole-5-carboxylic acid amide (I.13), 5 mL of dimethylformamide, 0.441 g (1.16 mmole) of 1-[bis(dimethylamino)methylene]-1H-1,2,3-triazolo[4,5-b]pyridinium, 3-oxide, hexafluorophosphate(1-) (1:1), 0.311 g (3.08 mmole) of triethylamine was stirred for 15 minutes, then 0.236 g (1.16 mmole) of 2-tert-butoxycarbonylamino-2-methyl-propionic acid was added. After 3 hours, the mixture was taken up in 100 mL of ethyl acetate, washed twice with 100 mL of water, and then once with 100 mL of brine. The ethyl acetate layer was dried over anhydrous sodium sulfate, filtered and concentrated under reduced pressure. The residue was purified by silica gel chromatography, eluting with dichloromethane-(methanol-ammonium hydroxide, (92.8:0.3)) (gradient 100:0-0:100) to give 0.250 g of 1-methyl-piperidine-4-carboxylic acid (1-{3-[5-carbamoyl-4-(3-chloro-phenyl)-thiazol-2-yl]-3H-benzoimidazol-5-ylmethyl}-piperidin-4-yl)-amide (I.15) as an off white solid. MH+/Z=652

Example 16

2-{6-[4-(2-Amino-2-methyl-propionylamino)-piperidin-1-ylmethyl]-benzoimidazol-1-yl}-4-(3-chloro-phenyl)-thiazole-5-carboxylic acid amide (I.16)

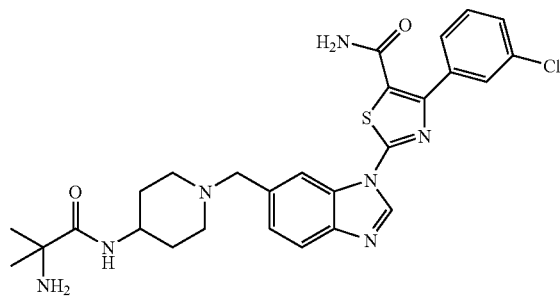

A mixture of 0.20 g (0.31 mmole) of 1-methyl-piperidine-4-carboxylic acid (1-{3-[5-carbamoyl-4-(3-chloro-phenyl)-thiazol-2-yl]3H-benzoimidazol-5-ylmethyl}-piperidin-4-yl)-amide (I.15), 15 mL of dichloromethane and 1 mL of trifluoroacetic acid was stirred for 2 hours then concentrated under reduced pressure. The residue was treated with 25 mL of saturated sodium bicarbonate and extracted three times with 50 mL of dichloromethane. The combined organic layers were washed with brine, dried over anhydrous sodium sulfate, filtered and concentrated under reduced pressure. The residue was purified by silica gel chromatography, eluting with dichloromethane-methanol (gradient 100:0-80:20) to give 0.070 g of 2-{6-[4-(2-amino-2-methyl-propionylamino)-piperidin-1-ylmethyl]-benzoimidazol-1-yl}-4-(3-chloro-phenyl)-thiazole-5-carboxylic acid amide (I.16) as a solid. MH+/Z=552

Example 17

2-[6-(4-Methyl-piperazin-1-ylmethyl)-benzoimidazol-1-yl]-4-(2-trifluoromethyl-phenyl)-thiazole-5-carboxylic acid amide (I.17)

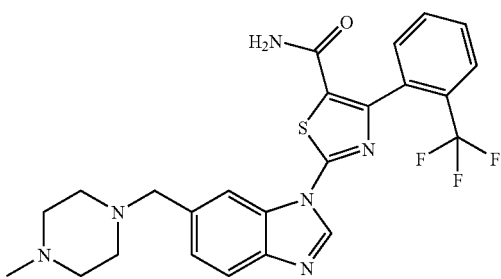

Step 1

A mixture of 0.20 g (0.70 mmole) of 2-amino-4-(2-trifluoromethyl-phenyl)-thiazole-5-carboxylic acid amide (V.17), 0.18 g (0.84 mmole) of 4-dimethoxymethyl-2-fluoro-1-nitrobenzene (IV.2a) and 1.14 g (3.5 mmole) of cesium carbonate in 12 mL of dimethylformamide was heated to 60 degrees for 3 hours, then cooled. The mixture was poured into ice water, extracted three times with ethyl acetate. The combined organic layers were washed with water, brine, dried over anhydrous sodium sulfate, filtered and concentrated under reduced pressure. Purification by silica gel chromatography, eluting with hexanes-ethyl acetate (gradient 100:0-50:50) gave 0.23 g of 2-(5-dimethoxymethyl-2-nitro-phenylamino)-4-(2-trifluoromethyl-phenyl)-thiazole-5-carboxylic acid amide (VI.17a) as a yellow solid.

Step 2

A solution of 0.23 g (0.48 mmole) of 2-(5-dimethoxymethyl-2-nitro-phenylamino)-4-(2-trifluoromethyl-phenyl)-thiazole-5-carboxylic acid amide (VI.17a) in 9 mL mixture of acetonitrile and 2M hydrochloric acid (2:1) was heated at 60 degrees for 3 hours, cooled and concentrated under reduced pressure. The residue was diluted with dichloromethane and saturated sodium bicarbonate. The solid was collected by filtration, washed with water and dried to give 0.14 g of 2-(5-formyl-2-nitro-phenylamino)-4-(2-trifluoromethyl-phenyl)-thiazole-5-carboxylic acid amide (VI.17b) as an orange solid. The filtrate was extracted twice with dichloromethane. The combined dichloromethane layers were washed with brine, dried over anhydrous sodium sulfate, concentrated under reduced pressure to give additional product of 0.046 g as an orange solid. The combined material was used directly in the next step without further purification.

Step 3

To a solution 0.18 g (0.41 mmole) of 2-(5-formyl-2-nitrophenylamino)-4-(2-trifluoromethyl-phenyl)-thiazole-5-carboxylic acid amide (VI.17b) and 0.18 g (0.83 mmole) of sodium triacetoxy-borohydride in 15 mL of dichloromethane was added 0.069 mL (0.62 mmole) of 1-methylpiperazine. The mixture was stirred at room temperature overnight. The mixture was then diluted with dichloromethane, washed with saturated sodium bicarbonate, brine, dried over anhydrous sodium sulfate and concentrated under reduced pressure. Purification of the residue by silica gel chromatography, eluting with dichloromethane-methanol (gradient 100:0-75:25) gave 0.16 g of 2-[5-(4-methyl-piperazin-1-ylmethyl)-2-nitrophenylamino]-4-(2-trifluoromethyl-phenyl)-thiazole-5-carboxylic acid amide (VI.17c) as a yellow solid.

Step 4

A mixture of 0.060 g (0.12 mmole) of 2-[5-(4-methyl-piperazin-1-ylmethyl)-2-nitro-phenylamino]-4-(2-trifluoromethyl-phenyl)-thiazole-5-carboxylic acid amide (VI.17c) in 7 mL of formic acid and 0.007 g of 10% palladium on carbon catalyst was stirred under an atmosphere of hydrogen for 18 hours. The mixture was filtered through a pad of Diatomaceous earth, washing the filter pad with dichloromethane. The filtrate was concentrated under reduced pressure. The residue was diluted with dichloromethane and saturated sodium bicarbonate. The organic layer was washed with brine, dried over anhydrous sodium sulfate and concentrated under reduced pressure. Purification of the residue by silica gel chromatography, eluting with dichloromethane-methanol (gradient 100:0-75:25) gave 0.034 g of 2-[6-(4-methyl-piperazin-1-ylmethyl)-benzoimidazol-1-yl]-4-(2-trifluoromethyl-phenyl)-thiazole-5-carboxylic acid amide (I.17) as a white solid. MH+/Z=501

Example 18

4-(4-Chloro-phenyl)-2-[5-(4-methyl-piperazin-1-ylmethyl)-benzoimidazol-1-yl]thiazole-5-carboxylic acid amide (I.18)

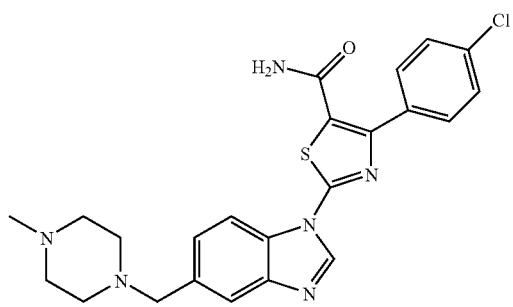

Step 1

To a mixture of 0.10 g (0.39 mmole) of 2-amino-4-(4-chloro-phenyl)-thiazole-5-carboxylic acid amide (V.18), 0.07 g (0.39 mmole) of 4-fluoro-3-nitrobenzaldehyde and 2 mL of dimethylformamide was added 0.19 g (0.59 mmole) of cesium carbonate. The mixture was heated at 120 degrees for 6 hours and then cooled. Water was then added and the suspension stirred at room temperature for one hour. The precipitate was collected by filtration, washed with water and dried under vacuum to give 0.16 g of 4-(4-chloro-phenyl)-2-(4-formyl-2-nitro-phenylamino)-thiazole-5-carboxylic acid amide (VI.18a).

Step 2

To a mixture of 0.10 g (0.24 mmole) of 4-(4-chloro-phenyl)-2-(4-formyl-2-nitro-phenylamino)-thiazole-5-carboxylic acid amide (VI.18a), 0.31 g (1.44 mmole) of sodium triacetoxyborohydride and 5 mL of dichloromethane was added 0.04 mL (0.36 mmole) of 1-methylpiperazine. The mixture was stirred at room temperature for 4 hours and then diluted with dichloromethane, washed with aqueous saturated sodium bicarbonate solution, brine, dried over anhydrous magnesium sulfate, filtered and concentrated under reduced pressure. The residue was purified by silica gel chromatography, eluting with methanol-dichloromethane (gradient 0:100-15:85) to give 0.044 g of 4-(4-chloro-phenyl)-2-[4-(4-methyl-piperazin-1-ylmethyl)-2-nitro-phenylamino]-thiazole-5-carboxylic acid amide (VI.18b).

Step 3

To a solution of 0.044 g (0.09 mmole) of 4-(4-chloro-phenyl)-2-[4-(4-methyl-piperazin-1-ylmethyl)-2-nitro-phenylamino]-thiazole-5-carboxylic acid amide (VI.18b) and 5 mL of formic acid (5 mL) was added 0.005 g of 10% Pd/C. The mixture was hydrogenated for 18 hours. The catalyst was removed by filtration and the filtrate concentrated under reduced pressure. The residue was diluted with dichloromethane, washed with aqueous saturated sodium bicarbonate solution and brine, dried over anhydrous magnesium sulfate, filtered, and concentrated under reduced pressure. The residue was purified by silica gel chromatography eluting with methanol-dichloromethane (gradient 20:80-40:60) to give 0.025 g of solid material. Recrystallization from acetonitrile-dichloromethane gave 0.019 g of 4-(4-chloro-phenyl)-2-[5-(4-methyl-piperazin-1-ylmethyl)-benzoimidazol-1-yl]-thiazole-5-carboxylic acid amide (I.18) as white needles. MH+/Z=467

Example 19

4-(4-Chloro-phenyl)-2-[6-(4-methyl-piperazin-1-ylmethyl)-benzoimidazol-1-yl]-thiazole-5-carboxylic acid amide (I.19)

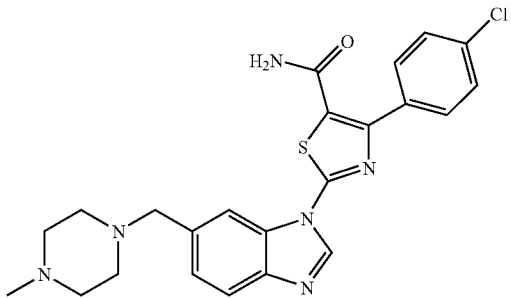

Step 1

A mixture of 0.89 g (3.51 mmole) of 2-amino-4-(4-chloro-phenyl)-thiazole-5-carboxylic acid amide (V.18), 0.91 g (4.21 mmole) of 4-dimethoxymethyl-2-fluoro-1-nitrobenzene, 5.70 g (17.55 mmole) of cesium carbonate (5.70 g, 17.55 mmole) and 10 mL of dimethylformamide was heated at 70 degrees for 2 days. The reaction mixture was diluted with ethyl acetate and water. The precipitate was collected by filtration, washed with water and dried under vacuum to give 0.55 g of 4-(4-chloro-phenyl)-2-(5-dimethoxymethyl-2-nitro-phenylamino)-thiazole-5-carboxylic acid amide (VI.19a).

Step 2

A mixture of 0.20 g (0.45 mmole) of 4-(4-chloro-phenyl)-2-(5-dimethoxy-methyl-2-nitro-phenylamino)-thiazole-5-carboxylic acid amide (VI.19a) and 9 mL of acetonitrile-aqueous 1M HCl (2:1) was heated at 60 degrees for 2 hours, then 8 mL of ethanol-aqueous 6M HCl (1:1) was added, and mixture heated at 60 degrees for one day. The solution was concentrated under reduced pressure and the residue was diluted with dichloromethane and aqueous saturated sodium bicarbonate solution. The organic phase was washed with brine, dried over anhydrous magnesium sulfate and concentrated under reduced pressure to give 0.16 g of 4-(4-chloro-phenyl)-2-(5-formyl-2-nitro-phenylamino)-thiazole-5-carboxylic acid amide (VI.19b).

Step 3

To a mixture of 0.16 g (0.40 mmole) of 4-(4-chloro-phenyl)-2-(5-formyl-2-nitro-phenylamino)-thiazole-5-carboxylic acid amide (VI.19b), 0.51 g (2.38 mmole) of sodium triacetoxy-borohydride and 15 mL of dichloromethane was added 0.07 mL (0.60 mmole) of 1-methylpiperazine. The mixture was stirred at room temperature for 18 hours. The mixture was diluted with dichloromethane and washed with saturated aqueous sodium bicarbonate solution and brine, dried over anhydrous magnesium sulfate, filtered, and concentrated under reduced pressure. The residue was purified by silica gel chromatography, eluting with methanol-dichloromethane (gradient 0:100-15:85) to give 0.16 g of 4-(4-chloro-phenyl)-2-[5-(4-methyl-piperazin-1-ylmethyl)-2-nitro-phenylamino]-thiazole-5-carboxylic acid amide (VI.19c).

Step 4

To a mixture of 0.16 g (0.33 mmole) of 4-(4-chloro-phenyl)-2-[5-(4-methyl-piperazin-1-ylmethyl)-2-nitro-phenylamino]-thiazole-5-carboxylic acid amide (VI.19c) and 15 mL of formic acid was added 0.02 g of 10% Pd/C. The mixture was hydrogenated for 18 hours. The catalyst was removed by filtration and the solution concentrated under reduced pressure. The residue was diluted with dichloromethane and washed with aqueous saturated sodium bicarbonate solution and brine, dried over anhydrous magnesium sulfate, filtered, and concentrated under reduced pressure. The residue was purified by silica gel chromatography, eluting with methanol-dichloromethane (gradient 5:95-25:75) to give 0.12 g of a solid. This solid was recrystallized from acetonitrile-dichloromethane to give 0.080 g of 4-(4-chloro-phenyl)-2-[6-(4-methyl-piperazin-1-ylmethyl)-benzoimidazol-1-yl]-thiazole-5-carboxylic acid amide (I.19) as white needles. MH+/Z=467

Example 20

4-(2-Chloro-phenyl)-2-[6-(4-methyl-piperazin-1-ylmethyl)-benzoimidazol-1-yl]-thiazole-5-carboxylic acid amide (I.20)

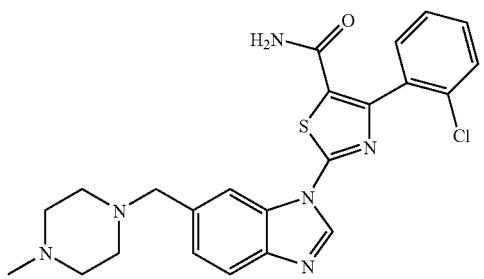

Step 1

A mixture of 0.15 g (0.60 mmole) of 2-amino-4-(2-chloro-phenyl)-thiazole-5-carboxylic acid amide (V.20), 0.15 g (0.72 mmole) of 4-dimethoxymethyl-2-fluoro-1-nitrobenzene, 0.99 g (3.0 mmole) of cesium carbonate and 10 mL of dimethylformamide was heated at 70 degrees for one day. The reaction mixture was diluted with ethyl acetate and water. The precipitate was collected by filtration, washed with water and dried under vacuum to give 0.24 g of 4-(2-chloro-phenyl)-2-(5-dimethoxymethyl-2-nitro-phenylamino)-thiazole-5-carboxylic acid amide (VI.20a).

Step 2

A mixture of 0.24 g (0.53 mmole) of 4-(2-chloro-phenyl)-2-(5-dimethoxy-methyl-2-nitro-phenylamino)-thiazole-5-carboxylic acid amide (VI.20a) and 12 mL of acetonitrile-2M HCl (2:1) was heated at 60 degrees for 3 hours. The solution was concentrated under reduced pressure. The residue was diluted with dichloromethane and saturated aqueous sodium bicarbonate solution. The precipitate was collected by filtration, washed with water and dried under vacuum to give 0.050 g of 4-(2-chloro-phenyl)-2-(5-formyl-2-nitro-phenylamino)-thiazole-5-carboxylic acid amide (VI.20b). The filtrate was extracted twice with dichloromethane. The combined organic layers were washed with brine, dried over anhydrous magnesium sulfate, filtered, and concentrated to give 0.15 g of 4-(2-chloro-phenyl)-2-(5-formyl-2-nitro-phenylamino)-thiazole-5-carboxylic acid amide (VI.20b).

Step 3

To a mixture of 0.20 g (0.50 mmole) of 4-(2-chloro-phenyl)-2-(5-formyl-2-nitro-phenylamino)-thiazole-5-carboxylic acid amide (VI.20b), 0.63 g (3.0 mmole) of sodium triacetoxyborohydride and 15 mL of dichloromethane was added 0.12 mL (1.08 mmole) of 1-methylpiperazine. The mixture was stirred at room temperature for 3 days. The mixture was diluted with dichloromethane, washed with saturated aqueous sodium bicarbonate solution and brine, dried over anhydrous magnesium sulfate, filtered and concentrated under reduced pressure. The residue was purified by silica gel chromatography, eluting with methanol-dichloromethane (gradient 0:100-15:85) to give 0.20 g of 4-(2-chloro-phenyl)-2-[5-(4-methyl-piperazin-1-ylmethyl)-2-nitro-phenylamino]-thiazole-5-carboxylic acid amide (VI.20c).

Step 4

To a solution of 0.20 g (0.33 mmole) of 4-(2-chloro-phenyl)-2-[5-(4-methyl-piperazin-1-ylmethyl)-2-nitro-phenylamino]-thiazole-5-carboxylic acid amide (VI.20c) and 10 mL of formic acid was added 0.02 g of 10% Pd/C. The mixture was hydrogenated for 18 hours. The catalyst was removed by filtration and the solution was concentrated under reduced pressure. The mixture was diluted with dichloromethane, washed with saturated aqueous sodium bicarbonate solution and brine, dried over anhydrous magnesium sulfate, filtered and concentrated under reduced pressure. The residue was purified by silica gel chromatography, eluting with methanol-dichloromethane (gradient 0:100-20:80) to give 0.12 g of a solid. The solid was recrystallized from acetonitrile-dichloromethane to give 0.10 g of 4-(2-chloro-phenyl)-2-[6-(4-methyl-piperazin-1-ylmethyl)-benzoimidazol-1-yl]-thiazole-5-carboxylic acid amide (I.20) as white crystalline material. MH+/Z=467

Example 21

4-(3-Chloro-phenyl)-2-[6-(piperidin-4-yloxy)-benzoimidazol-1-yl]-thiazole-5-carboxylic acid amide (I.21)

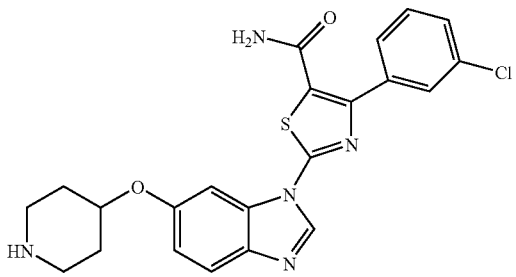

Step 1

To a mixture of 5.0 g (31.80 mmole) of 3-fluoro-4-nitrophenol, 8.32 g (41.31 mmole) of 4-hydroxy-piperidine-1-carboxylic acid tert-butyl ester and 14.32 g (54.06 mmole) of triphenylphosphine in 100 mL of tetrahydrofuran was added 8.4 mL (54.06 mmole) of diethyl azodicarboxylate. The mixture was stirred at room temperature for 18 hours and then concentrated under reduced pressure. The residue was purified by silica gel chromatography eluting with ethyl acetate-hexanes (gradient 0:100-40:60) to give 6.94 g of 4-(3-fluoro-4-nitro-phenoxy)-piperidine-1-carboxylic acid tert-butyl ester (IV.21a).

Step 2

To a mixture of 0.35 g (1.38 mmole) of 2-amino-4-(3-chloro-phenyl)-thiazole-5-carboxylic acid amide (V.2), 0.56 g (1.66 mmole) of 4-(3-fluoro-4-nitro-phenoxy)-piperidine-1-carboxylic acid tert-butyl ester (IV.21a) and 10 mL of dimethylformamide was added 2.24 g (6.90 mmole) of cesium carbonate. The mixture was heated at 70 degrees for 5 hours and then diluted with ethyl acetate and water. The aqueous phase was extracted three times with ethyl acetate. The combined organic layers were washed with water and brine, dried over anhydrous magnesium sulfate, filtered and concentrated under reduced pressure. The residue was purified by silica gel chromatography eluting with ethyl acetate-hexanes (gradient 0:100-40:60) to give 0.37 g of 4-{3-[5-carbamoyl-4-(3-chloro-phenyl)-thiazole-2-ylamino]-4-nitro-phenoxy}-piperidine-1-carboxylic acid tert-butyl ester (VI.21).

Step 3

To 0.14 g (0.25 mmole) of 4-{3-[5-carbamoyl-4-(3-chloro-phenyl)-thiazole-2-ylamino]-4-nitro-phenoxy}-piperidine-1-carboxylic acid tert-butyl ester (VI.21), 6 mL of acetonitrile, 6 mL of ethanol and 2 mL of 1M hydrochloric acid was added 0.32 g (4.97 mg-atom) of zinc powder. The mixture was stirred at room temperature for 18 hours. The solid was filtered off and the filtrate was concentrated under reduced pressure. The residue was diluted with ethyl acetate and saturated aqueous sodium bicarbonate solution. The organic phase was washed with brine, dried over anhydrous magnesium sulfate, filtered, and concentrated under reduced pressure to give 4-{3-[5-carbamoyl-4-(3-chloro-phenyl)-thiazole-2-ylamino]-4-nitro-phenoxy}-piperidine-1-carboxylic acid tert-butyl ester (VII.21).

Step 4

The crude 4-{3-[5-carbamoyl-4-(3-chloro-phenyl)-thiazole-2-ylamino]-4-nitro-phenoxy}-piperidine-1-carboxylic acid tert-butyl ester (VII.21) was dissolved in 4 mL of acetic acid and 0.14 mL (0.84 mmole) of triethyl orthoformate. The mixture was heated at 70 degrees for 2 hours. The reaction mixture was concentrated under reduced pressure. The residue was diluted with ethyl acetate and saturated aqueous sodium carbonate solution. The organic phase was washed with brine, dried over anhydrous magnesium sulfate, filtered and concentrated under reduced pressure. The residue was purified by silica gel chromatography, eluting with ethyl acetate-dichloromethane (gradient 50:50-100:0) to give 0.10 g of 4-{3-[5-carbamoyl-4-(3-chloro-phenyl)-thiazole-2-yl]-3H-benzoimidazol-5-yloxy}-piperidine-1-carboxylic acid tert-butyl ester (I.21a).

Step 5

To 0.10 g (0.18 mmole) of 4-{3-[5-carbamoyl-4-(3-chloro-phenyl)-thiazole-2-yl]-3H-benzoimidazol-5-yloxy}-piperidine-1-carboxylic acid tert-butyl ester (I.21a) in 5 mL of dichloromethane at 0 degrees, was added 5 mL of dichloromethane-trifluoroacetic acid (1:1). The mixture was stirred at 0 degrees for 1 hour and then concentrated under reduced pressure. The residue was diluted with dichloromethane and washed with saturated aqueous sodium carbonate solution, brine, dried over anhydrous magnesium sulfate, filtered, and concentrated under reduced pressure. The residue was recrystallized from methanol to give 0.050 g 4-(3-chloro-phenyl)- 2-[6-(piperidin-4-yloxy)-benzoimidazol-1-yl]-thiazole-5-carboxylic acid amide (I.21). MH+/Z=454

Example 22

4-(3-Chloro-phenyl)-2-[6-(1-methyl-piperidin-4-yloxy)-benzoimidazol-1-yl]-thiazole-5-carboxylic acid amide (I.22)

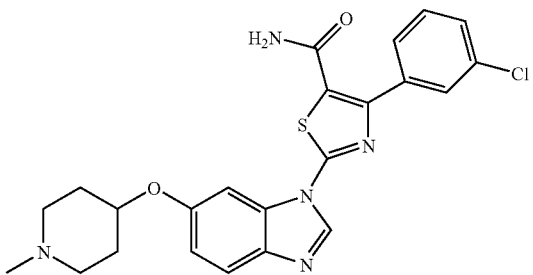

To a mixture of 0.041 g (0.09 mmole) 4-(3-chloro-phenyl)-2-[6-(piperidin-4-yloxy)-benzoimidazol-1-yl]-thiazole-5-carboxylic acid amide (I.21), 0.0135 mL of 37% aqueous formaldehyde solution, 0.0062 mL (0.11 mmole) of acetic acid and 2.1 mL of methanol-dichloromethane (2:5) was added 0.029 g (0.14 mmole) of sodium triacetoxy-borohydride. The mixture was stirred at room temperature for 18 hours. The solution was concentrated under reduced pressure. The residue was diluted with dichloromethane-ethyl acetate and washed with aqueous 1M sodium hydroxide solution and brine, dried over anhydrous magnesium sulfate, filtered and concentrated under reduced pressure. The residue was purified by silica gel chromatography, eluting with methanol-dichloromethane (gradient 10:90-20:80) to give 0.034 g of 4-(3-chloro-phenyl)-2-[6-(1-methyl-piperidin-4-yloxy)-benzoimidazol-1-yl]-thiazole-5-carboxylic acid amide (1.22). MH+/Z=468

Example 23

4-(3-Chloro-phenyl)-2-[6-(piperidin-4-ylmethoxy)-benzoimidazol-1-yl]-thiazole-5-carboxylic acid amide (I.23)

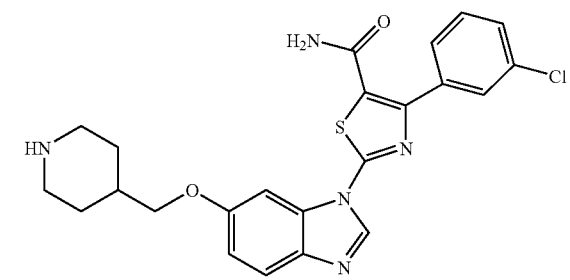

Step 1

To a mixture of 1.0 g (6.37 mmole) of 3-fluoro-4-nitrophenol, 1.78 g (8.27 mmole) of 4-hydroxymethyl-piperidine-1-carboxylic acid tert-butyl ester, 2.81 g (10.71 mmole) of triphenylphosphine and 50 mL of tetrahydrofuran was added 1.67 mL (10.71 mmole) of diethylazodicarboxylate. The mixture was stirred at room temperature for 18 hours and then concentrated under reduced pressure. The residue was purified by silica gel chromatography eluting with ethyl acetate-hexanes (gradient 0:100-40:60) to give 2.16 g of 4-(3-fluoro-4-nitro-phenoxymethyl)-piperidine-1-carboxylic acid tert-butyl ester (IV.23).

Step 2

To a mixture of 0.35 g (1.38 mmole) of 2-amino-4-(3-chloro-phenyl)-thiazole-5-carboxylic acid amide (V.2), 0.59 g (1.66 mmole) of 4-(3-fluoro-4-nitro-phenoxymethyl)-piperidine-1-carboxylic acid tert-butyl ester (IV.23) and 10 mL of dimethylformamide was added 2.24 g (6.90 mmole) of cesium carbonate. The mixture was heated at 70 degrees for 5 hours and then diluted with ethyl acetate and water. The aqueous phase was extracted three times with ethyl acetate. The combined organic phases were washed with water and brine, dried over anhydrous magnesium sulfate, filtered, and concentrated under reduced pressure. The residue was purified by silica gel chromatography eluting with ethyl acetate-hexanes (gradient 0:100-40:60) to give 0.15 g of 4-{3-[5-carbamoyl-4-(3-chloro-phenyl)-thiazole-2-ylamino]-4-nitro-phenoxymethyl}-piperidine-1-carboxylic acid tert-butyl ester (VI.23).

Step 3

To 0.15 g (0.25 mmole) of 4-{3-[5-carbamoyl-4-(3-chloro-phenyl)-thiazole-2-ylaminomethyl]-4-nitro-phenoxy}-piperidine-1-carboxylic acid tert-butyl ester (VI.23), 6 mL of acetonitrile, 6 mL of ethanol and 2 mL of 1M hydrochloric acid was added 0.32 g (4.97 mg-atom) of zinc powder. The mixture was stirred at room temperature for 18 hours. The solid was filtered off and the filtrate was concentrated under reduced pressure. The residue was diluted with ethyl acetate and saturated aqueous sodium bicarbonate. The organic phase was washed with brine, dried over anhydrous magnesium sulfate, filtered, and concentrated under reduced pressure to give 4-{3-[5-carbamoyl-4-(3-chloro-phenyl)-thiazole-2-ylamino]-4-nitro-phenoxymethyl}-piperidine-1-carboxylic acid tert-butyl ester (VII.23).

Step 4

The crude 4-{3-[5-carbamoyl-4-(3-chloro-phenyl)-thiazole-2-ylamino]-4-nitro-phenoxymethyl}-piperidine-1-carboxylic acid tert-butyl ester (VII.23) was dissolved in 4 mL of acetic acid and 0.14 mL (0.84 mmole) of triethyl orthoformate. The mixture was heated at 70 degrees for 2 hours and then concentrated under reduced pressure. The residue was diluted with ethyl acetate and saturated aqueous sodium carbonate. The organic phase was washed with brine, dried over anhydrous magnesium sulfate, filtered, and concentrated under reduced pressure. The residue was purified by silica gel chromatography eluting with ethyl acetate-dichloromethane (gradient 50:50-100:0) to give 0.13 g of 4-{3-[5-carbamoyl-4-(3-chloro-phenyl)-thiazole-2-yl]-3H-benzoimidazol-5-yloxymethyl}-piperidine-1-carboxylic acid tert-butyl ester (I.23a).

Step 5

To 0.13 g (0.23 mmole) of 4-{3-[5-carbamoyl-4-(3-chloro-phenyl)-thiazole-2-yl]-3H-benzoimidazol-5-yloxymethyl}-piperidine-1-carboxylic acid tert-butyl ester (I.23a) in 5 mL of dichloromethane at 0 degrees, was added 5 mL of dichloromethane-trifluoroacetic acid (1:1). The mixture was stirred at 0 degrees for 1 hour and then concentrated under reduced pressure. The residue was diluted with dichloromethane, washed with saturated aqueous sodium carbonate solution and brine, dried over anhydrous magnesium sulfate, filtered, and concentrated under reduced pressure. The residue was recrystallized from methanol to give 0.10 g of 4-(3-chloro-phenyl)-2-[6-(piperidin-4-ylmethoxy)-benzoimidazol-1-yl]-thiazole-5-carboxylic acid amide (I.23). MH+/Z=468

Example 24

4-(3-Chloro-phenyl)-2-[6-(1-methyl-piperidin-4-ylmethoxy)-benzoimidazol-1-yl]-thiazole-5-carboxylic acid amide (I.24)

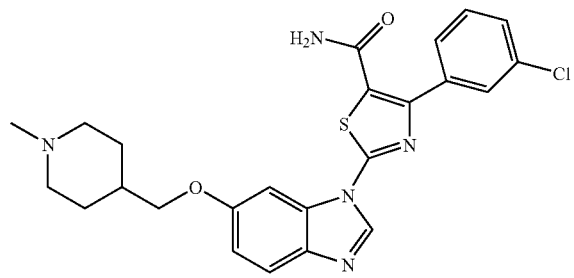

To a mixture of 0.030 g (0.06 mmole) of 4-(3-chloro-phenyl)-2-[6-(piperidin-4-ylmethoxy)-benzoimidazol-1-yl]-thiazole-5-carboxylic acid amide (I.23), 0.0095 mL (0.13 mmole) of 37% aqueous formaldehyde solution, 0.0041 mL (0.070 mmole) of acetic acid and 2.1 mL of methanol-dichloromethane (2:5) was added 0.019 g (0.090 mmole) of sodium triacetoxyborohydride. The mixture was stirred at room temperature for 18 hours and then concentrated under reduced pressure. The residue was diluted with dichloromethane and ethyl acetate, washed with aqueous 1M sodium hydroxide solution and brine, dried over anhydrous magnesium sulfate, filtered, and concentrated under reduced pressure. The residue was recrystallized from methanol-dichloromethane to give 0.015 g of 4-(3-chloro-phenyl)-2-[6-(1-methyl-piperidin-4-ylmethoxy)-benzoimidazol-1-yl]-thiazole-5-carboxylic acid amide (I.24). MH+/Z=482

Example 25

4-(3-Chloro-phenyl)-2-(6-cyclohexyloxy-benzoimidazol-1-yl)-thiazole-5-carboxylic acid amide (I.25)

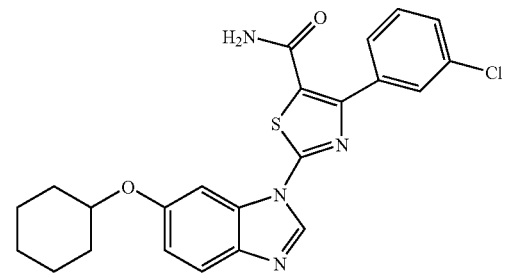

Step 1

To a mixture of 3.14 g (20 mmole) of 3-fluoro-4-nitrophenol, 100 mL of acetonitrile and 8.3 g (60 mmole) of potassium carbonate was added 2.5 mL (21 mmole) of benzyl bromide. The mixture was heated to reflux for 1 hour, then cooled and concentrated under reduced pressure. The residue was stirred with 100 mL for 30 minutes. The solid was collected by filtration and air dried to give 4.76 g of 4-benzyloxy-2-fluoro-1-nitro-benzene as a yellow solid.

Step 2

To a mixture of 2.57 g (10 mmole) of 4-benzyloxy-2-fluoro-1-nitro-benzene, 2.83 g (10 mmole) of 2-amino-4-(3-chloro-phenyl)-thiazole-5-carboxylic acid ethyl ester and 20 mL of dimethylformamide was added 16.25 g (50 mmole) of cesium carbonate. The mixture was heated at 100 degrees for 1 hour. The reaction was allowed to cool to room temperature and then 500 mL of water was added. The mixture was stirred for 15 minutes and the resulting yellow solid collected by filtration to give 5.09 g of 2-(5-benzyloxy-2-nitro-phenylamino)-4-(3-chloro-phenyl)-thiazole-5-carboxylic acid ethyl ester (VI.25).

Step 3

To a mixture of 5.09 g (10 mmole) of 2-(5-benzyloxy-2-nitro-phenylamino)-4-(3-chloro-phenyl)-thiazole-5-carboxylic acid ethyl ester (VI.25), 100 mL of tetrahydrofuran and 20 mL of 1M hydrochloric acid, was added portionwise, 10 g of zinc powder. The mixture was stirred at ambient temperature for 2 hours. The solid was removed by filtration, the filtrate was concentrated under reduced pressure and 200 mL of water was added to the residue. The pH was adjusted to 9 by addition of 15% sodium hydroxide. The precipitate was collected by filtration to give crude 2-(2-amino-5-benzyloxy-phenylamino)-4-(3-chloro-phenyl)-thiazole-5-carboxylic acid ethyl ester (VII.25). This material was carried through to next reaction without further purification.

Step 4

A mixture of the 2-(2-amino-5-benzyloxy-phenylamino)-4-(3-chloro-phenyl)-thiazole-5-carboxylic acid ethyl ester (VII.25) from previous step, 50 mL of acetic acid, 5 mL of triethyl orthoformate was heated to 50 degrees for 1 hour. The mixture was concentrated under reduced pressure and the residue taken up in 200 mL of dichloromethane. The mixture was washed with 100 mL saturated sodium bicarbonate. The aqueous layer was extracted twice with 100 mL of dichloromethane. The combined organic layers were washed with brine, dried over anhydrous magnesium sulfate, filtered and concentrated under reduced pressure. The residue was triturated with diethyl ether to afford 3.5 g of 2-(6-benzyloxy-benzoimidazol-1-yl)-4-(3-chloro-phenyl)-thiazole-5-carboxylic acid ethyl ester (I.25a) as an off-white solid.

Step 5

A mixture of 3.5 g (7.14 mmole) of 2-(6-benzyloxy-benzoimidazol-1-yl)-4-(3-chloro-phenyl)-thiazole-5-carboxylic acid ethyl ester (I.25a), 50 mL of tetrahydrofuran, 50 mL of water and 0.857 g (35.7 mmole) of lithium hydroxide was heated at 60 degrees for 3 hours. The mixture was concentrated under reduced pressure, and then 100 mL of water was added. The pH was adjusted to ca. 3-4 by the addition of hydrochloric acid. The resulting precipitate was collected by filtration to give 3.3 g of 2-(6-benzyloxy-benzoimidazol-1-yl)-4-(3-chloro-phenyl)-thiazole-5-carboxylic acid (I.25b) as a white solid.

Step 6

To a mixture of 3.3 g (7.16 mmole) of 2-(6-benzyloxy-benzoimidazol-1-yl)-4-(3-chloro-phenyl)-thiazole-5-carboxylic acid (I.25b), 20 mL of dimethylformamide and 3.26 g (8.59 mmole) of 1-[bis(dimethylamino)methylene]-1H-1,2,3-triazolo[4,5-b]pyridinium, 3-oxide, hexafluorophosphate(1-) (1:1) was added 0.759 g (14.52 mmole) of ammonium chloride followed by 3.74 mL (21.48 mmole) of ethyldiisopropylamine. The mixture was stirred at ambient temperature for 1 hour and then diluted with 500 mL of water. The suspension was stirred for 30 minutes. The precipitate was collected by filtration to afford 3.2 g of 2-(6-benzyloxy-benzoimidazol-1-yl)-4-(3-chloro-phenyl)-thiazole-5-carboxylic acid amide as an off-white solid (I.25c).

Step 7

To a mixture of 3.2 g (6.96 mmole) of 2-(6-benzyloxy-benzoimidazol-1-yl)-4-(3-chloro-phenyl)-thiazole-5-carboxylic acid amide (I.25c) and 50 mL of dichloromethane at 0 degrees was added, dropwise, 5.86 mL (56 mmole) of boron trifluoride-dimethylsulfide complex. The mixture was stirred at ambient temperature for 1 hour and then 50 mL of water was added. The mixture was stirred vigorously for 1 hour. The precipitate was collected by filtration to give 2.6 g of 4-(3-chloro-phenyl)-2-(6-hydroxy-benzoimidazol-1-yl)-thiazole-5-carboxylic acid amide (I.25d) as an off-white solid.

Step 8

To a mixture of 0.051 g (0.2 mmole) of toluene-4-sulfonic acid cyclohexyl ester, 0.037 g (0.1 mmole) of 4-(3-chloro-phenyl)-2-(6-hydroxy-benzoimidazol-1-yl)-thiazole-5-carboxylic acid amide (I.25d) and 1 mL of dimethylformamide was added 0.163 g (0.5 mmole) of cesium carbonate. The mixture was heated at 100 degrees for 30 minutes. The mixture was cooled, the solid was removed by filtration and the filtrate purified by reverse phase silica gel chromatography, eluting with acetonitrile-water (gradient 40:60-100:0) to give 0.027 g of 4-(3-chloro-phenyl)-2-(6-cyclohexyloxy-benzoimidazol-1-yl)-thiazole-5-carboxylic acid amide (I.25) as a white powder. MH+/Z=453

Example 26

4-(3-Chloro-phenyl)-2-[6-(2-morpholin-4-yl-ethoxy)-benzoimidazol-1-yl]-thiazole-5-carboxylic acid amide (I.26)

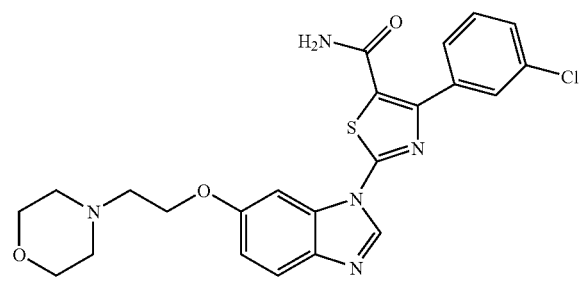

Step 1

To a mixture of 0.656 g (5 mmole) of 2-morpholin-4-yl-ethanol and 20 mL of dichloromethane at 0 degrees was added 2.49 g (7.5 mmole) of carbon tetrabromide and then 1.57 g (6 mmole) of triphenylphosphine. The mixture was stirred at ambient temperature overnight. The mixture was concentrated under reduced pressure and 50 mL of hexanes was added. The solid was removed by filtration and the filtrate was concentrated under reduced pressure. Purification of the residue by silica gel chromatography, eluting with ethyl acetate-hexanes (gradient 0:100-30:70) gave 0.580 g of 4-(2-bromo-ethyl)-morpholine as a colorless oil.

Step 2

To a mixture of 0.037 (0.1 mmole) of 4-(3-chloro-phenyl)-2-(6-hydroxy-benzoimidazol-1-yl)-thiazole-5-carboxylic acid amide (I.25d), 0.039 g (0.2 mmole) of 4-(2-bromo-ethyl)-morpholine and 1 mL of dimethylformamide was added 0.16 g (0.5 mmole) of cesium carbonate. The mixture was heated at 100 degrees for 3 hours. The mixture was cooled, the solid was removed by filtration and the filtrate purified by reverse phase silica gel chromatography, eluting with acetonitrile-water (gradient 30:70-100:0) to give 0.014 g of 4-(3-chloro-phenyl)-2-[6-(2-morpholin-4-yl-ethoxy)-benzoimidazol-1-yl]-thiazole-5-carboxylic acid amide (I.26) as a white powder. MH+/Z=484

Example 27

4-(3-Chloro-phenyl)-2-[6-(2-piperidin-1-yl-ethoxy)-benzoimidazol-1-yl]-thiazole-5-carboxylic acid amide (I.27)

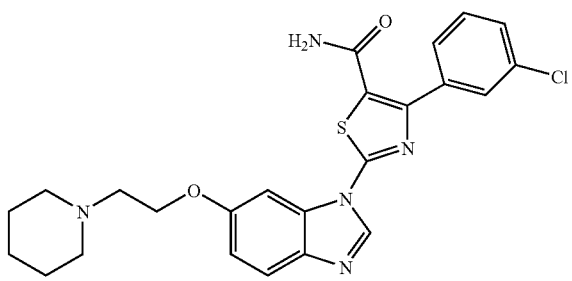

Step 1

To a mixture of 0.573 g (4 mmole) of 2-piperidin-1-yl-ethanol and 8 mL of pyridine at 0 degrees was added 0.763 g (4 mmole) of p-toluenesulphonyl chloride. The mixture was stirred at ambient temperature for 3 hours. The mixture was concentrated under reduced pressure and 10 mL of water was added. The mixture was extracted twice with 10 mL of dichloromethane. The combined organic layers were washed with brine, dried over anhydrous magnesium sulfate, filtered and concentrated under reduced pressure to give toluene-4-sulfonic acid 2-piperidin-1-yl-ethyl ester as a purple oil, which was carried to next step without further purification.

Step 2

To a mixture of 0.037 g (0.1 mmole) of 4-(3-chloro-phenyl)-2-(6-hydroxy-benzoimidazol-1-yl)-thiazole-5-carboxylic acid amide (I.25d), 0.060 g (0.2 mmole) of toluene-4-sulfonic acid 2-piperidin-1-yl-ethyl ester and 1 mL of dimethylformamide was added 0.160 g (0.5 mmole) of cesium carbonate. The reaction mixture was heated at 100 degrees for 3 hours. The mixture was cooled, the solid was removed by filtration and the filtrate purified by reverse phase silica gel chromatography, eluting with acetonitrile-water (gradient 30:70-100:0) to give 0.027 g of 4-(3-chloro-phenyl)-2-[6-(2-piperidin-1-yl-ethoxy)-benzoimidazol-1-yl]-thiazole-5-carboxylic acid amide (I.27) as a white powder. MH+/Z=482

Example 28

4-(3-Chloro-phenyl)-2-{6-[2-(4-methyl-piperazin-1-yl)-ethoxy]-benzoimidazol-1-yl}-thiazole-5-carboxylic acid amide (I.28)

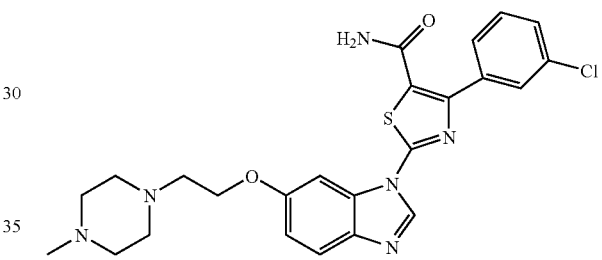

Step 1

To a mixture of 0.371 g (1 mmole) of 4-(3-chloro-phenyl)-2-(6-hydroxy-benzoimidazol-1-yl)-thiazole-5-carboxylic acid amide (I.25d), 1.63 g (5 mmole) of cesium carbonate and 3 mL of dimethylformamide was added 0.249 mL (3 mmole) of 1-bromo-2-chloro-ethane. The mixture was heated at 100 degrees for 30 minutes. The cooled mixture was diluted with 20 mL of water and the resulting precipitate collected by filtration and then air dried. The solid was triturated with acetonitrile to give 0.269 g of 2-[6-(2-chloro-ethoxy)-benzoimidazol-1-yl]-4-(3-chloro-phenyl)-thiazole-5-carboxylic acid amide (I.28a) as a yellow solid.

Step 2

A mixture of 0.043 g (0.1 mmole) of 2-[6-(2-chloro-ethoxy)-benzoimidazol-1-yl]-4-(3-chloro-phenyl)-thiazole-5-carboxylic acid amide (I.28a), 1 mL of dimethylformamide, 0.069 g (0.5 mmole) of potassium carbonate, 0.001 g of potassium iodide and 0.033 mL (0.3 mmole) of 1-methyl-piperazine was stirred at 100 degrees for 6 hours. The mixture was cooled, the solid was removed by filtration and the filtrate purified by reverse phase silica gel chromatography, eluting with acetonitrile-water (gradient 30:70-100:0) to give 0.038 g of 4-(3-chloro-phenyl)-2-{6-[2-(4-methyl-piperazin-1-yl)- ethoxy]-benzoimidazol-1-yl}-thiazole-5-carboxylic acid amide (I.28) as a white solid. MH+/Z=497

Example 29

4-(3-Chloro-phenyl)-2-[6-(2-dimethylamino-ethoxy)-benzoimidazol-1-yl]-thiazole-5-carboxylic acid amide (I.29)

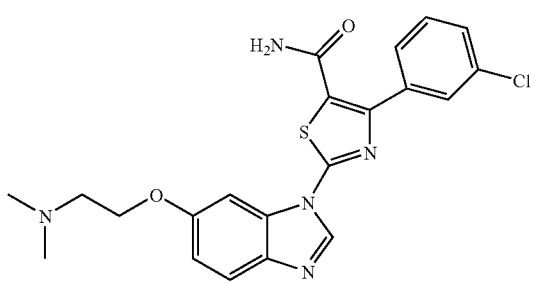

A mixture of 0.043 g (0.1 mmole) of 2-[6-(2-chloro-ethoxy)-benzoimidazol-1-yl]-4-(3-chloro-phenyl)-thiazole-5-carboxylic acid amide (I.28a), 1 mL of dimethylformamide, 0.069 g (0.5 mmole) of potassium carbonate, 0.001 g of potassium iodide and 0.150 mL (0.3 mmole) of dimethylamine was stirred at 100 degrees for 6 hours. The mixture was cooled, the solid was removed by filtration and the filtrate purified by reverse phase silica gel chromatography, eluting with acetonitrile-water (gradient 30:70-100:0) to give 0.034 g of 4-(3-chloro-phenyl)-2-[6-(2-dimethylamino-ethoxy)-benzoimidazol-1-yl]-thiazole-5-carboxylic acid amide (I.29) as a white powder. MH+/Z=442

Example 30

4-(3-Chloro-phenyl)-2-[6-(3-morpholin-4-yl-propoxy)-benzoimidazol-1-yl]-thiazole-5-carboxylic acid amide (I.30)

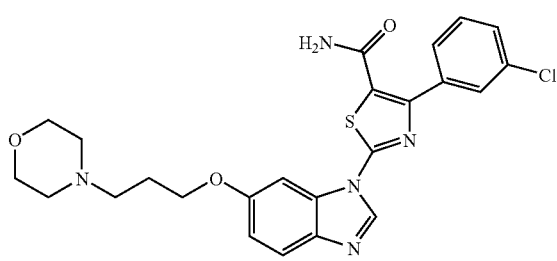

Step 1

To a mixture of 0.145 g (1 mmole) of 3-morpholin-4-yl-propan-1-ol and 5 mL of pyridine was added 0.001 g of 4-dimethylaminopyridine and 0.210 g (1.1 mmole) of p-toluenesulphonyl chloride. The mixture was stirred at ambient temperature overnight and then concentrated under reduced pressure. The residue was taken up in 10 mL of dichloromethane and washed once with 5 mL of saturated sodium bicarbonate, twice with 5 mL of water, and then brine, dried over anhydrous magnesium sulfate, filtered and concentrated under reduced pressure to give 0.22 g of toluene-4-sulfonic acid 3-morpholin-4-yl-propyl ester as a colorless oil.

Step 2

A mixture of 0.037 g (0.1 mmole) of 4-(3-chloro-phenyl)-2-(6-hydroxy-benzoimidazol-1-yl)-thiazole-5-carboxylic acid amide (I.25d), 0.060 g (0.2 mmole) of toluene-4-sulfonic acid 3-morpholin-4-yl-propyl ester, 1 mL of dimethylformamide and 0.160 g (0.5 mmole) of cesium carbonate was heated at 100 degrees for 30 minutes. The mixture was cooled, the solid was removed by filtration and the filtrate purified by reverse phase silica gel chromatography, eluting with acetonitrile-water (gradient 20:80-100:0) to give 0.028 g of 4-(3-chloro-phenyl)-2-[6-(3-morpholin-4-yl-propoxy)-benzoimidazol-1-yl]-thiazole-5-carboxylic acid amide (I.30) as a white powder. MH+/Z=498

Example 31

4-(3-Chloro-phenyl)-2-[6-(3-dimethylamino-propoxy)-benzoimidazol-1-yl]-thiazole-5-carboxylic acid amide (I.31)

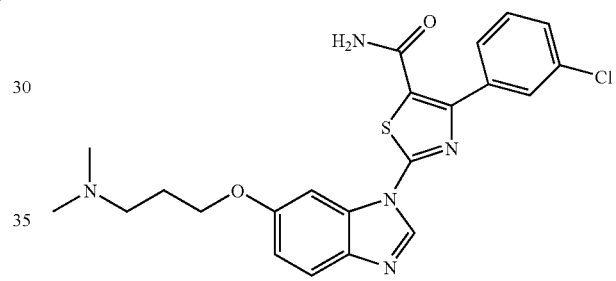

Step 1

To a mixture of 0.206 g (2 mmole) of 3-dimethylamino-propan-1-ol, and 2 mL of pyridine (2 ml) was added 0.001 g of 4-dimethylaminopyridine and 0.381 g (2 mmole) of p-toluenesulphonyl chloride. The mixture was stirred at ambient temperature overnight and then concentrated under reduced pressure. The residue was taken up in 10 mL of dichloromethane and washed once with 5 mL of saturated sodium bicarbonate, twice with 5 mL of water, and then brine, dried over anhydrous magnesium sulfate, filtered and concentrated under reduced pressure to give 0.085 g of toluene-4-sulfonic acid 3-dimethylamino-propyl ester as a colorless oil.

Step 2

A mixture of 0.037 g (0.1 mmole) of 4-(3-chloro-phenyl)-2-(6-hydroxy-benzoimidazol-1-yl)-thiazole-5-carboxylic acid amide (I.25d), 0.051 g (0.2 mmole) of toluene-4-sulfonic acid 3-dimethylamino-propyl ester, 1 mL of dimethylformamide and 0.160 g (0.5 mmole) of cesium carbonate was heated at 100 degrees for 30 minutes. The mixture was cooled, the solid was removed by filtration and the filtrate purified by reverse phase silica gel chromatography, eluting with acetonitrile-water (gradient 30:70-100:0) to give 0.018 g of 4-(3-chloro-phenyl)-2-[6-(3-dimethylamino-propoxy)-benzoimidazol-1-yl]-thiazole-5-carboxylic acid amide (I.31) as a white powder. MH+/Z=456

Example 32

4-(3-Chloro-phenyl)-2-[6-(3-piperidin-1-yl-propoxy)-benzoimidazol-1-yl]-thiazole-5-carboxylic acid amide (I.32)

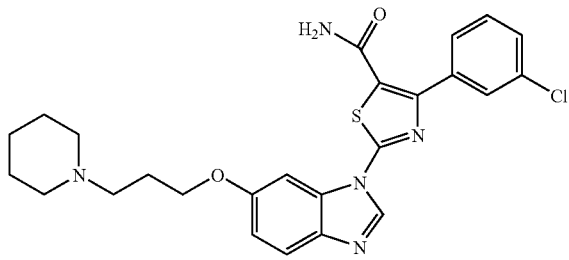

Step 1

To a mixture of 0.286 g (2 mmole) of 3-piperidin-1-yl-propan-1-ol, and 2 mL of pyridine was added 0.001 g of 4-dimethylaminopyridine and 0.381 g (2 mmole) of p-toluenesulphonyl chloride. The mixture was stirred at ambient temperature overnight and then concentrated under reduced pressure. The residue was taken up in 20 mL of dichloromethane and washed once with 10 mL of saturated sodium bicarbonate, twice with 10 mL of water, and then brine, dried over anhydrous magnesium sulfate, filtered and concentrated under reduced pressure to give 0.384 g of toluene-4-sulfonic acid 3-piperidin-1-yl-propyl ester as a pink solid.

Step 2

A mixture of 0.037 g (0.1 mmole) of 4-(3-chloro-phenyl)-2-(6-hydroxy-benzoimidazol-1-yl)-thiazole-5-carboxylic acid amide (I.25d), 0.060 g (0.2 mmole) of toluene-4-sulfonic acid 3-piperidin-1-yl-propyl ester, 1 mL of dimethylformamide and 0.160 g (0.5 mmole) of cesium carbonate was heated at 100 degrees for 30 minutes. The mixture was cooled, the solid was removed by filtration and the filtrate purified by reverse phase silica gel chromatography, eluting with acetonitrile-water (gradient 40:60-100:0) to give 0.035 g of 4-(3-chloro-phenyl)-2-[6-(3-piperidin-1-yl-propoxy)-benzoimidazol-1-yl]-thiazole-5-carboxylic acid amide (I.32) as a white powder. MH+/Z=496

Example 33

4-(3-Chloro-phenyl)-2-{6-[3-(4-methyl-piperazin-1-yl)-propoxy]-benzoimidazol-1-yl}-thiazole-5-carboxylic acid amide (I.33)

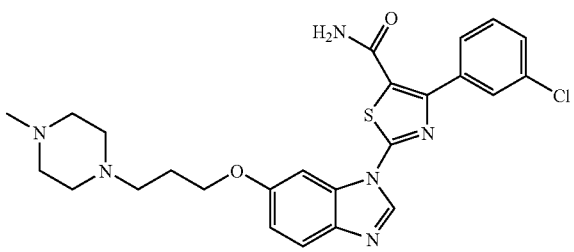

Step 1

To a mixture of 0.158 g (1 mmole) of 3-(4-methyl-piperazin-1-yl)-propan-1-ol, and 5 mL of pyridine was added 0.001 g of 4-dimethylaminopyridine and 0.190 g (1 mmole) of p-toluenesulphonyl chloride. The mixture was stirred at ambient temperature overnight and then concentrated under reduced pressure. The residue was taken up in 20 mL of dichloromethane and washed once with 10 mL of saturated sodium bicarbonate, twice with 10 mL of water, and then brine, dried over anhydrous magnesium sulfate, filtered and concentrated under reduced pressure to give 0.248 g of 3-(4-methyl-piperazin-1-yl)-propyl ester as a colorless oil.

Step 2

A mixture of 0.037 g (0.1 mmole) of 4-(3-chloro-phenyl)-2-(6-hydroxy-benzoimidazol-1-yl)-thiazole-5-carboxylic acid amide (I.25d), 0.062 g (0.2 mmole) of toluene-4-sulfonic acid 3-(4-methyl-piperazin-1-yl)-propyl ester, 1 mL of dimethylformamide and 0.160 g (0.5 mmole) of cesium carbonate was heated at 100 degrees for 20 minutes. The mixture was cooled, the solid was removed by filtration and the filtrate purified by reverse phase silica gel chromatography, eluting with acetonitrile-water (gradient 40:60-100:0) to give 0.025 g of 4-(3-chloro-phenyl)-2-{6-[3-(4-methyl-piperazin-1-yl)-propoxy]-benzoimidazol-1-yl}-thiazole-5-carboxylic acid amide (I.33) as a white powder. MH+/Z=511

Example 34

4-(3-Chloro-phenyl)-2-[6-(3-pyrrolidin-1-yl-propoxy)-benzoimidazol-1-yl]-thiazole-5-carboxylic acid amide (I.34)

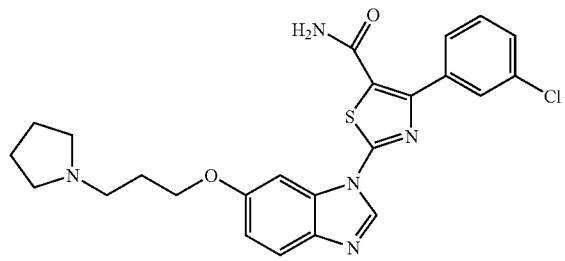

Step 1

A mixture of 0.370 g (1 mmole) of 4-(3-chloro-phenyl)-2-(6-hydroxy-benzoimidazol-1-yl)-thiazole-5-carboxylic acid amide (I.25d), 3 mL of dimethylformamide, 1.6 g (5 mmole) of cesium carbonate and 0.297 mL (3 mmole) of 1-bromo-3-chloro-propane was heated at 100 degrees for 1 hour. The cooled mixture was diluted with 20 mL of water and the resulting precipitate collected by filtration. The solid was triturated with diethyl ether to give 0.355 g of 2-[6-(3-chloro-propoxy)-benzoimidazol-1-yl]-4-(3-chloro-phenyl)-thiazole-5-carboxylic acid amide (I.34a) as a brown solid.

Step 2

A mixture of 0.043 g (0.1 mmole) of 2-[6-(3-chloro-propoxy)-benzoimidazol-1-yl]-4-(3-chloro-phenyl)-thiazole-5-carboxylic acid amide (I.34a), 1 mL of dimethylformamide, 0.069 g (0.5 mmole) of potassium carbonate, 0.001 g of potassium iodide and 0.025 mL (0.3 mmole) of pyrrolidine was stirred at 100 degrees for 6 hours. The mixture was concentrated under reduced pressure, and diluted with 20 mL of water. The precipitate was collected by filtration and the solid triturated with diethyl ether to give 0.036 g of 4-(3-chloro-phenyl)-2-[6-(3-pyrrolidin-1-yl-propoxy)-benzoimidazol-1-yl]-thiazole-5-carboxylic acid amide (I.34) as a white solid. MH+/Z=482

Example 35

2-(6-{3-[Bis-(2-hydroxy-ethyl)-amino]-propoxy}-benzoimidazol-1-yl)-4-(3-chloro-phenyl)-thiazole-5-carboxylic acid amide (I.35)

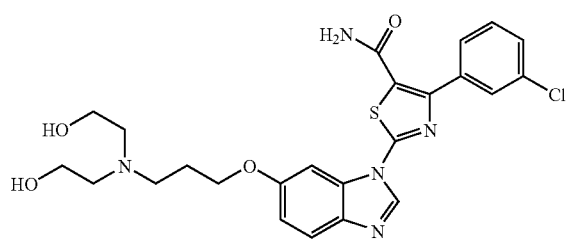

A mixture of 0.043 g (0.1 mmole) of 2-[6-(3-chloro-propoxy)-benzoimidazol-1-yl]-4-(3-chloro-phenyl)-thiazole-5-carboxylic acid amide (I.34a), 1 mL of dimethylformamide, 0.069 g (0.5 mmole) of potassium carbonate, 0.001 g of potassium iodide and 0.029 mL (0.3 mmole) of 2-(2-hydroxy-ethylamino)-ethanol was stirred at 100 degrees for 3 hours. The mixture was concentrated under reduced pressure, and diluted with 20 mL of water. The precipitate was collected by filtration and the solid triturated with diethyl ether to give 0.029 g of 2-(6-{3-[bis-(2-hydroxy-ethyl)-amino]-propoxy}-benzoimidazol-1-yl)-4-(3-chloro-phenyl)-thiazole-5-carboxylic acid amide (I.35) as a white powder. MH+/Z=516

Example 36

4-(3-Chloro-phenyl)-2-{6-[3-(2-hydroxy-ethylamino)-propoxy]-benzoimidazol-1-yl}-thiazole-5-carboxylic acid amide (I.36)

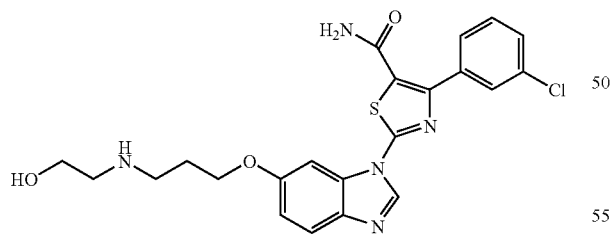

A mixture of 0.043 g (0.1 mmole) of 2-[6-(3-chloro-propoxy)-benzoimidazol-1-yl]-4-(3-chloro-phenyl)-thiazole-5-carboxylic acid amide (I.34a), 1 mL of dimethylformamide, 0.069 g (0.5 mmole) of potassium carbonate, 0.001 g of potassium iodide and 0.011 mL (0.2 mmole) of 2-aminoethanol was stirred at 100 degrees for 6 hours. The mixture was cooled, the solid was removed by filtration and the filtrate purified by reverse phase silica gel chromatography, eluting with acetonitrile-water (gradient 20:80-100:0) to give 0.031 g of 2-(6-{3-[bis-(2-hydroxy-ethyl)-amino]-propoxy}-benzoimidazol-1-yl)-4-(3-chloro-phenyl)-thiazole-5-carboxylic acid amide (I.36) as a white powder. MH+/Z=472

Example 37

4-(3-Chloro-phenyl)-2-{6-[4-(4-methyl-piperazin-1-yl)-butoxy]-benzoimidazol-1-yl}-thiazole-5-carboxylic acid amide (I.37)

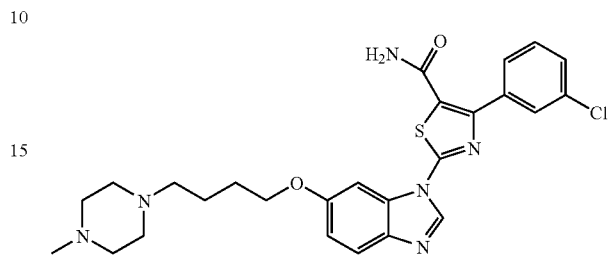

Step 1

A mixture of 0.185 g (0.5 mmole) of 4-(3-chloro-phenyl)-2-(6-hydroxy-benzoimidazol-1-yl)-thiazole-5-carboxylic acid amide (I.25d), 1.5 mL of dimethylformamide, 0.813 g (2.5 mmole) of cesium carbonate and 0.173 mL (1.5 mmole) of 1-bromo-4-chloro-butane was heated at 100 degrees for 1 hour. The mixture was concentrated under reduced pressure, diluted with water and the resulting precipitate collected by filtration. The solid was triturated with diethyl ether to give 0.279 g of 2-[6-(4-chloro-butoxy)-benzoimidazol-1-yl]-4-(3-chloro-phenyl)-thiazole-5-carboxylic acid amide (I.37a) as a light brown solid.

Step 2

A mixture of 0.023 g (0.05 mmole) of 2-[6-(4-chloro-butoxy)-benzoimidazol-1-yl]-4-(3-chloro-phenyl)-thiazole-5-carboxylic acid amide (I.37a), 0.5 mL of dimethylformamide, 0.035 g (0.25 mmole) of potassium carbonate, 0.001 g of potassium iodide and 0.017 mL (0.15 mmole) of 1-methyl-piperazine was stirred at 100 degrees for 3 hours. The mixture was concentrated under reduced pressure, and diluted with 20 mL of water. The precipitate was collected by filtration and the solid triturated with diethyl ether to give 0.018 g of 4-(3-chloro-phenyl)-2-{6-[4-(4-methyl-piperazin-1-yl)-butoxy]-benzoimidazol-1-yl}-thiazole-5-carboxylic acid amide (I.37) as a white powder. MH+/Z=525

Example 38

4-(3-Chloro-phenyl)-2-[6-(4-morpholin-4-yl-butoxy)-benzoimidazol-1-yl]-thiazole-5-carboxylic acid amide (I.38)

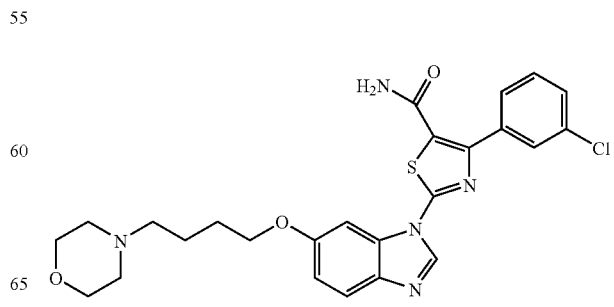

A mixture of 0.023 g (0.05 mmole) of 2-[6-(4-chlorobutoxy)-benzoimidazol-1-yl]-4-(3-chloro-phenyl)-thiazole-5-carboxylic acid amide (I.37a), 0.5 mL of dimethylformamide, 0.035 g (0.25 mmole) of potassium carbonate, 0.001 g of potassium iodide and 0.013 mL (0.15 mmole) of morpholine was stirred at 100 degrees for 3 hours. The mixture was concentrated under reduced pressure, and diluted with 20 mL of water. The precipitate was collected by filtration and the solid triturated with diethyl ether to give 0.019 g of 4-(3-chloro-phenyl)-2-{6-[4-(4-methyl-piperazin-1-yl)-butoxy]-benzoimidazol-1-yl}-thiazole-5-carboxylic acid amide (I.38) as a white powder. MH+/Z=512

Example 39

4-(3-Chloro-phenyl)-2-{6-[2-hydroxy-3-(4-methyl-piperazin-1-yl)-propoxy]-benzoimidazol-1-yl}-thiazole-5-carboxylic acid amide (I.39)

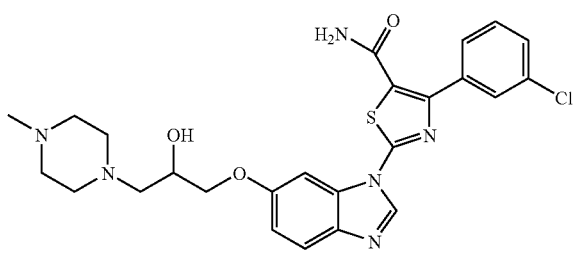

Step 1

A mixture of 0.037 g (0.1 mmole) of 4-(3-chloro-phenyl)-2-(6-hydroxy-benzoimidazol-1-yl)-thiazole-5-carboxylic acid amide (I.25d), 0.5 mL of dimethylformamide, 0.069 g (0.5 mmole) of potassium carbonate, 0.001 g of potassium iodide and 0.012 mL (0.15 mmole) of 2-chloromethyl-oxirane was heated at 100 degrees for 3 hours. The mixture was concentrated under reduced pressure, diluted with 20 mL of water and the resulting precipitate collected by filtration. The solid was triturated with diethyl ether to give 0.032 g of 4-(3-chloro-phenyl)-2-(6-oxiranylmethoxy-benzoimidazol-1-yl)-thiazole-5-carboxylic acid amide (I.39a) as a white solid.

Step 2

A mixture of 0.021 g (0.05 mmole) of 4-(3-chloro-phenyl)-2-(6-oxiranylmethoxy-benzoimidazol-1-yl)-thiazole-5-carboxylic acid amide (I.39a), 0.5 mL of dimethylformamide, 0.035 g (0.25 mmole) of potassium carbonate and 0.017 mL (0.15 mmole) of 1-methyl-piperazine was heated at 100 degrees for 5 hours. The mixture was cooled, the solid was removed by filtration and the filtrate purified by reverse phase silica gel chromatography, eluting with acetonitrile-water (gradient 20:80-100:0) to give 0.015 g of 4-(3-chloro-phenyl)-2-{6-[2-hydroxy-3-(4-methyl-piperazin-1-yl)-propoxy]-benzoimidazol-1-yl}-thiazole-5-carboxylic acid amide (I.39) as a white powder. MH+/Z=527

Example 40

4-(3-Chloro-phenyl)-2-[6-(2-hydroxy-3-morpholin-4-yl-propoxy)-benzoimidazol-1-yl]-thiazole-5-carboxylic acid amide (I.40)

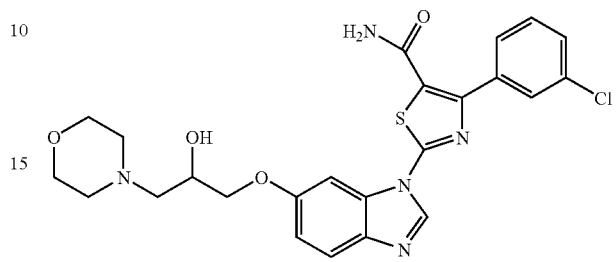

A mixture of 0.021 g (0.05 mmole) of 4-(3-chloro-phenyl)-2-(6-oxiranylmethoxy-benzoimidazol-1-yl)-thiazole-5-carboxylic acid amide (I.39a), 0.5 mL of dimethylformamide, 0.035 g (0.25 mmole) of potassium carbonate and 0.009 mL (0.1 mmole) of morpholine was heated at 100 degrees for 3 hours. The mixture was cooled, the solid was removed by filtration and the filtrate purified by reverse phase silica gel chromatography, eluting with acetonitrile-water (gradient 20:80-100:0) to give 0.012 g of 4-(3-chloro-phenyl)-2-{6-[2-hydroxy-3-(4-methyl-piperazin-1-yl)-propoxy]-benzoimidazol-1-yl}-thiazole-5-carboxylic acid amide (I.40) as a white powder. MH+/Z=514

Example 41

4-(3-Chloro-phenyl)-2-[6-(4-morpholin-4-yl-butyl)-benzoimidazol-1-yl]-thiazole-5-carboxylic acid amide (I.41)

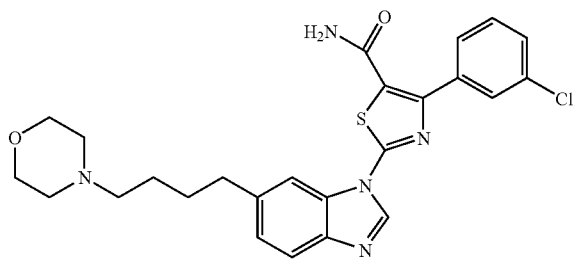

Step 1

A mixture of 2.82 g (10 mmole) of 2-amino-4-(3-chloro-phenyl)-thiazole-5-carboxylic acid ethyl ester, 9.75 g (30 mmole) of cesium carbonate, 20 mL of dimethylformamide, and 2.15 g (10 mmole) of 4-dimethoxymethyl-2-fluoro-1-nitro-benzene was heated at 80 degrees for 1 hour. The cooled mixture was diluted with 200 mL of water and extracted three times with 100 mL of dichloromethane. The combined organic layers were washed with brine, dried over anhydrous magnesium sulfate, filtered and concentrated under reduced pressure. The residue was purified with silica gel chromatography, eluting with ethyl acetate-hexanes (gradient 0:100-10:90) to give 3.4 g of 4-(3-chloro-phenyl)-2-(5-dimethoxymethyl-2-nitro-phenylamino)-thiazole-5-carboxylic acid ethyl ester (VI.41a) as a yellow solid.

Step 2

A mixture of 3.4 g (0.71 mmole) of 4-(3-chloro-phenyl)-2-(5-dimethoxymethyl-2-nitro-phenylamino)-thiazole-5-carboxylic acid ethyl ester (VI.41a), 80 mL of acetonitrile and 20 mL of 1M hydrochloric acid was heated 60 degrees for 30 minutes. The mixture was concentrated under reduced pressure, 200 mL of water was added and the pH was adjusted to 9 by the addition of 15% sodium hydroxide solution. The precipitate was collected by filtration to give 3.0 g of 4-(3-chloro-phenyl)-2-(5-formyl-2-nitro-phenylamino)-thiazole-5-carboxylic acid ethyl ester (VI.41b) as a white solid.

Step 3

To mixture of 3.0 g of 4-(3-chloro-phenyl)-2-(5-formyl-2-nitro-phenylamino)-thiazole-5-carboxylic acid ethyl ester (VI.41b), 40 mL of tetrahydrofuran and 20 mL of saturated ammonium chloride solution, was added in three equal portions, at 30 minute intervals, 9 g of zinc powder. After the third portion of zinc powder was added, the orange color disappeared and the mixture turned clear. The solid was removed by filtration. The organic layer was separated. The aqueous layer was extracted twice with 30 mL of dichloromethane. The combined organic layers were washed with brine, dried over anhydrous magnesium sulfate, filtered and concentrated under reduced pressure. The residue was stirred with 30 mL of acetic acid and 3 mL of trimethyl orthoformate for 1 hour. The mixture was concentrated under reduced pressure, 100 mL of water was and the pH adjusted to 9 by addition of 15% sodium hydroxide solution. The precipitate was collected by filtration and purified by silica gel chromatography, eluting with methanol-dichloromethane (gradient 0:100-2:98) to give 2.3 g of 4-(3-chloro-phenyl)-2-(6-formyl-benzoimidazol-1-yl)-thiazole-5-carboxylic acid ethyl ester (I.41a) as an off-white solid.

Step 4

To a suspension of 0.983 g (2 mmole) of (3-benzyloxypropyl)triphenylphosphonium bromide and 20 mL of tetrahydrofuran at −78 degrees was added 1.33 mL (2.4 mmole) of 1.8 M phenyllithium solution. The mixture was stirred for 10 minutes and then 0.823 g (2 mmole) of 4-(3-chloro-phenyl)-2-(6-formyl-benzoimidazol-1-yl)-thiazole-5-carboxylic acid ethyl ester (I.41a) was added. The reaction was allowed to warm up to room temperature, stirred for 2 hours and then quenched by the addition of 10 mL of saturated ammonium chloride solution. The layers were separated. The aqueous layer was extracted twice with 20 mL of ethyl acetate. The combined organic layers were washed with brine, dried over anhydrous magnesium sulfate, filtered and concentrated under reduced pressure. The residue was purified by silica gel chromatography, eluting with methanol-dichloromethane (gradient 0:100-1.5:98.5) to give 0.568 g of 2-[6-(-benzyloxy-but-1-enyl)-benzoimidazol-1-yl]-4-(3-chloro-phenyl)-thiazole-5-carboxylic acid ethyl ester (I.41b) as a yellow solid.

Step 5

A mixture of 0.568 g of 2-[6-(-benzyloxy-but-1-enyl)-benzoimidazol-1-yl]-4-(3-chloro-phenyl)-thiazole-5-carboxylic acid ethyl ester (I.41b), 5 mL of tetrahydrofuran, 5 mL of ethanol, and 0.30 g of 10% palladium on carbon catalyst was hydrogenated at 50 psi overnight. The catalyst was removed by filtration and the filtrate was concentrated under reduced pressure. The residue was purified by silica gel chromatography, eluting with methanol-dichloromethane (gradient 0:100-2:98) to give 0.434 g of 2-[6-(4-benzyloxy-butyl)-benzoimidazol-1-yl]-4-(3-chloro-phenyl)-thiazole-5-carboxylic acid ethyl ester (I.41c) as white solid.

Step 6

To a mixture of 0.434 g (0.795 mmole) of 2-[6-(4-benzyloxy-butyl)-benzoimidazol-1-yl]-4-(3-chloro-phenyl)-thiazole-5-carboxylic acid ethyl ester (I.41c) and 5 mL of acetonitrile at 0 degrees was added dropwise 0.836 mL (0.795 mmole) of boron trifluoride-dimethyl sulfide complex. The mixture was stirred at ambient temperature for 2 hours and then concentrated under reduced pressure. Saturated sodium bicarbonate was added to the residue and the mixture was extracted three times with 15 mL of dichloromethane. The combined organic layers were washed with brine, dried over anhydrous magnesium sulfate, filtered and concentrated under reduced pressure. The residue was purified by silica gel chromatography, eluting with methanol-dichloromethane (gradient 0:100-3:97) to give 0.266 g of 4-(3-chloro-phenyl)-2-[6-(4-hydroxy-butyl)-benzoimidazol-1-yl]-thiazole-5-carboxylic acid ethyl ester (I.41d) as a white solid.

Step 7

To a solution of 0.266 g (0.583 mmole) of 4-(3-chloro-phenyl)-2-[6-(4-hydroxy-butyl)-benzoimidazol-1-yl]-thiazole-5-carboxylic acid ethyl ester (I.41d), 0.152 mL (0.875 mmole) of ethyldiisopropylamine and 5 mL of dichloromethane at 0 degrees was added 0.054 mL (0.7 mmole) of methanesulfonyl chloride. The mixture was stirred at ambient temperature for 1 hour and then diluted with 30 mL of dichloromethane. The mixture was washed with 10 mL of saturated sodium bicarbonate, brine, dried over anhydrous magnesium sulfate, filtered and concentrated under reduced pressure. The residue was purified by silica gel chromatography, eluting with methanol-dichloromethane (gradient 0:100-2:98) to give 0.248 g of 4-(3-chloro-phenyl)-2-[6-(4-methanesulfonyloxy-butyl)-benzoimidazol-1-yl]-thiazole-5-carboxylic acid ethyl ester (I.41e) as a yellow solid.

Step 8

A mixture of 0.107 g (0.2 mmole) of 4-(3-chloro-phenyl)-2-[6-(4-methanesulfonyloxy-butyl)-benzoimidazol-1-yl]-thiazole-5-carboxylic acid ethyl ester (I.41e), 0.138 g (1 mmole) of potassium carbonate, 2 mL of acetonitrile and 0.035 mL (0.4 mmole) of morpholine was refluxed for 6 hours. The solid was removed by filtration and the filtrate concentrated under reduced pressure. The residue was purified by silica gel chromatography, eluting with methanol-dichloromethane (gradient 0:100-5:95) to give 0.078 g of 4-(3-chloro-phenyl)-2-[6-(4-morpholin-4-yl-butyl)-benzoimidazol-1-yl]-thiazole-5-carboxylic acid ethyl ester (I.41f) as a yellow solid.

Step 9

To a mixture of 0.078 g (0.15 mmole) of 4-(3-chloro-phenyl)-2-[6-(4-morpholin-4-yl-butyl)-benzoimidazol-1-yl]-thiazole-5-carboxylic acid ethyl ester (I.41f), 2 mL of tetrahydrofuran and 2 mL of water was added 0.034 g (1.49 mmole) of lithium hydroxide. The mixture was stirred at ambient temperature for 2 hours, then concentrated under reduced pressure and diluted with 5 mL of water. The pH was adjusted to ca. 6-7 by addition of 3M hydrochloric acid. The precipitate was collected by filtration to give 0.054 g of 4-(3-chloro-phenyl)-2-[6-(4-morpholin-4-yl-butyl)-benzoimidazol-1-yl]-thiazole-5-carboxylic acid (I.41 g) as a white solid.

Step 10

To a mixture of 0.050 g (0.1 mmole) of 4-(3-chloro-phenyl)-2-[6-(4-morpholin-4-yl-butyl)-benzoimidazol-1-yl]-thiazole-5-carboxylic acid (I.41 g), 1 mL of dimethylformamide and 0.0418 g (0.11 mmole) of 1-[bis(dimethylamino)methylene]-1H-1,2,3-triazolo[4,5-b]pyridinium, 3-oxide, hexafluorophosphate(1-) (1:1) was added 0.016 g (0.3 mmole) of ammonium chloride and 0.052 mL (0.3 mmole) of ethyldiisopropylamine. The mixture was stirred at ambient temperature for 1 hour. The solid was removed by filtration and the filtrate was purified by reverse phase silica gel chromatography, eluting with acetonitrile-water (gradient 20:80-100:0) to give 0.032 g of 4-(3-chloro-phenyl)-2-[6-(4-morpholin-4-yl-butyl)-benzoimidazol-1-yl]-thiazole-5-carboxylic acid amide (I.41) as a white powder. MH+/Z=496

Example 42

4-(3-Chloro-phenyl)-2-{5-methoxy-6-[3-(4-methyl-piperazin-1-yl)-propoxy]-benzoimidazol-1-yl}-thiazole-5-carboxylic acid amide (I.42)

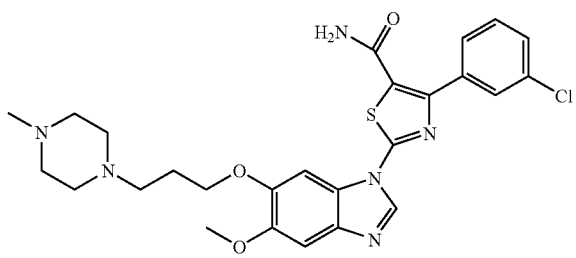

Step 1

A mixture of 0.350 g (1.87 mmole) of 5-fluoro-2-methoxy-4-nitro-phenol, 0.568 g (2.25 mmole) of (3-bromo-propoxy)-tert-butyl-dimethyl-silane, 1.29 g (9.35 mmole) of potassium carbonate and 5 mL of dimethylformamide was heated at 60 degrees for 3 hours. The mixture was cooled, poured into 50 mL of dilute ammonium chloride solution and extracted three times with 25 mL of ethyl acetate. The combined organic extracts were washed three times with 25 mL of water, once with 25 mL of brine, dried over anhydrous magnesium sulfate, filtered and concentrated under reduced pressure. The residue was purified by silica gel chromatography, eluting with dichloromethane-hexanes (60:40) to give 0.469 g of tert-butyl-[3-(5-fluoro-2-methoxy-4-nitro-phenoxy)-propoxy]-dimethyl-silane (IV.42) as a white solid.

Step 2

A mixture of 0.469 g (1.31 mmole) of tert-butyl-[3-(5-fluoro-2-methoxy-4-nitro-phenoxy)-propoxy]-dimethyl-silane (IV.42), 0.331 g (1.31 mmole) of 2-amino-4-(3-chloro-phenyl)-thiazole-5-carboxylic acid amide (V.2), 1.28 g (3.93 mmole) of cesium carbonate and 5 mL of dimethylformamide was heated at 70 degrees for 3 hours. The mixture was cooled and 3 mL of 6M hydrochloric acid was added dropwise. Stirring was continued for 15 minutes. The mixture was poured into 50 mL of water, and the precipitated orange solid was collected by filtration, washed with water, and air-dried to give 0.535 g of 4-(3-chloro-phenyl)-2-[5-(3-hydroxy-propoxy)-4-methoxy-2-nitro-phenylamino]-thiazole-5-carboxylic acid amide (VI.42).

Step 3

A mixture of 0.200 g (0.42 mmole) of 4-(3-chloro-phenyl)-2-[5-(3-hydroxy-propoxy)-4-methoxy-2-nitro-phenylamino]-thiazole-5-carboxylic acid amide (VI.42), 0.150 g of 10% palladium on carbon catalyst, and 4 mL of 96% formic acid was stirred under 1 atmosphere of hydrogen at room temperature for 16 hours. The mixture was filtered through Diatomaceous earth, and the Diatomaceous earth pad was washed with formic acid. The filtrate was heated at reflux for 1 hour, cooled and concentrated under reduced pressure. The residue was dissolved in 4 mL of dimethylsulfoxide and 0.30 g of potassium hydroxide in 1 mL of water was added dropwise. The mixture was stirred at room temperature for 1 hour and then diluted with 10 mL of water. The resulting precipitate was collected by filtration and washed with water to give 0.105 g of 4-(3-chloro-phenyl)-2-[6-(3-hydroxy-propoxy)-5-methoxy-benzoimidazol-1-yl]-thiazole-5-carboxylic acid amide (I.42a) as a purple solid.

Step 4

To a mixture of 0.067 g (0.15 mmole) of 4-(3-chloro-phenyl)-2-[6-(3-hydroxy-propoxy)-5-methoxy-benzoimidazol-1-yl]-thiazole-5-carboxylic acid amide (I.42a), 0.036 g (0.36 mmole) of triethylamine and 2 mL of dimethylformamide at 0 degrees was added, 0.020 g (0.18 mmole) of methanesulfonyl chloride. The mixture was stirred for 1 hour and then 1 mL of saturated ammonium chloride solution was added dropwise. The mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was heated at 80 degrees for 1 hour with 2 mL of dimethylformamide and 0.080 mL of N-methylpiperazine. The mixture was cooled, poured into 25 mL of water extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was purified by silica gel chromatography, eluting with methanol-dichloromethane (25:75) to give 0.026 g of 4-(3-chloro-phenyl)-2-{5-methoxy-6-[3-(4-methyl-piperazin-1-yl)-propoxy]-benzoimidazol-1-yl}thiazole-5-carboxylic acid amide (I.42) as a pink solid. MH+/Z=541

Example 43

4-(3-Chloro-phenyl)-2-[5-methoxy-6-(3-morpholin-4-yl-propoxy)-benzoimidazol-1-yl]-thiazole-5-carboxylic acid amide (I.43)

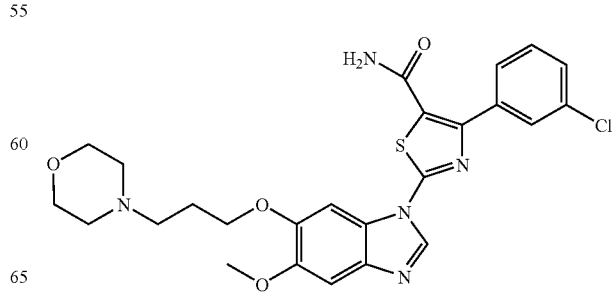

To a mixture of 0.070 g (0.15 mmole) of 4-(3-chloro-phenyl)-2-[6-(3-hydroxy-propoxy)-5-methoxy-benzoimidazol-1-yl]-thiazole-5-carboxylic acid amide (I.42a), 0.039 g (0.30 mmole) of ethyldiisopropylamine and 3 mL of dimethylformamide at 0 degrees was added 0.021 g (0.18 mmole) of methanesulfonyl chloride. Stirring was continued for 1 hour and then 1 mL of saturated ammonium chloride solution was added. The mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was heated at 80 degrees for 1 hour with 2 mL of dimethylformamide and 0.080 mL of morpholine. The cooled mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was purified by silica gel chromatography, eluting with methanol-dichloromethane (8:92) to give 0.021 g of 4-(3-chloro-phenyl)-2-[5-methoxy-6-(3-morpholin-4-yl-propoxy)-benzoimidazol-1-yl]-thiazole 5-carboxylic acid amide (I.43) as a pink solid. MH+/Z=528

Example 44

4-(3-Chloro-phenyl)-2-{5-methoxy-6-[2-(4-methyl-piperazin-1-yl)-ethoxy]-benzoimidazol-1-yl}-thiazole-5-carboxylic acid amide (I.44)

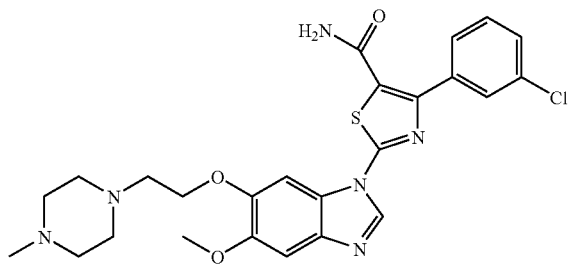

Step 1

A mixture of 0.374 g (2 mmole) of 5-fluoro-2-methoxy-4-nitro-phenol, 0.439 g (2.10 mmole) of 2-(2-bromo-ethoxy)-tetrahydro-pyran, 0.828 g (6.0 mmole) of potassium carbonate and 5 mL of dimethylformamide was heated at 80 degrees for 4 hours. The cooled mixture was poured into 50 mL of dilute ammonium chloride solution and extracted three times with 25 mL of ethyl acetate. The combined organic extracts were washed three times with 25 mL of water, once with 25 mL of brine, dried over anhydrous magnesium sulfate, filtered and concentrated under reduced pressure. The residue was purified by silica gel chromatography, eluting with ethyl acetate-hexanes (gradient 20:80-30:70) to give 0.370 g of 2-[2-(5-fluoro-2-methoxy-4-nitro-phenoxy)-ethoxy]-tetrahydro-pyran (IV.44) as a yellow oil.

Step 2

A mixture of 0.370 g of 2-[2-(5-fluoro-2-methoxy-4-nitro-phenoxy)-ethoxy]-tetrahydro-pyran (IV.44), 0.296 g (1.17 mmole) of 2-amino-4-(3-chloro-phenyl)-thiazole-5-carboxylic acid amide (V.2), 1.14 g (3.51 mmole) of cesium carbonate and 5 mL of dimethylformamide was heated at 70 degrees for 3 hours. The cooled mixture was poured into 30 mL of dilute ammonium chloride solution and the precipitated orange solid was collected by filtration, washed with water, and air-dried to give 0.470 g 4-(3-chloro-phenyl)-2-{4-methoxy-2-nitro-5-[2-(tetrahydro-pyran-2-yloxy)-ethoxy]-phenylamino}-thiazole-5-carboxylic acid amide (VI.44).

Step 3

A mixture of 0.470 g (0.86 mmole) of 4-(3-chloro-phenyl)-2-{4-methoxy-2-nitro-5-[2-(tetrahydro-pyran-2-yloxy)-ethoxy]-phenylamino}-thiazole-5-carboxylic acid amide (VI.44), 0.250 g of 10% palladium on carbon catalyst and 3 mL of 96% formic acid was stirred under 1 atmosphere of hydrogen for 16 hours. The mixture was filtered through diatomaceous earth and the diatomaceous earth pad was washed with formic acid. The filtrate was heated at reflux for 2 hours, cooled and concentrated under reduced pressure. The residue was dissolved in 5 mL of dimethylsulfoxide and 0.20 g of potassium hydroxide in 1 mL of water was added dropwise. The mixture was stirred at room temperature for 30 minutes and then diluted with 50 mL of water. The resulting precipitate was collected by filtration and washed with water to give 0.190 g of 4-(3-chloro-phenyl)-2-[6-(2-hydroxy-ethoxy)-5-methoxy-benzoimidazol-1-yl]-thiazole-5-carboxylic acid amide (I.44a) as a purple solid.

Step 4

To a mixture of 0.070 g (0.15 mmole) of 4-(3-chloro-phenyl)-2-[6-(2-hydroxy-ethoxy)-5-methoxy-benzoimidazol-1-yl]-thiazole-5-carboxylic acid amide (I.44a), 0.041 g (0.242 mmole) of ethyldiisopropylamine and 3 mL of dimethylformamide 0 degrees was added 0.027 g (0.24 mmole) of methanesulfonyl chloride. Stirring was continued for 1 hour and then 1 mL of saturated ammonium chloride solution was added dropwise. The mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was heated at 80 degrees for 1 hour with 2 mL of dimethylformamide and 0.080 g of N-methylpiperazine. The mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was purified by silica gel chromatography, eluting with methanol-dichloromethane (gradient 12:88-17:83) to give 0.023 g of 4-(3-chloro-phenyl)-2-{5-methoxy-6-[2-(4-methyl-piperazin-1-yl)-ethoxy]-benzoimidazol-1-yl}thiazole-5-carboxylic acid amide (I.44) as a pink solid. MH+/Z=527

Example 45

4-(3-Chloro-phenyl)-2-[5-methoxy-6-(2-morpholin-4-yl-ethoxy)-benzoimidazol-1-yl]-thiazole-5-carboxylic acid amide (I.45)

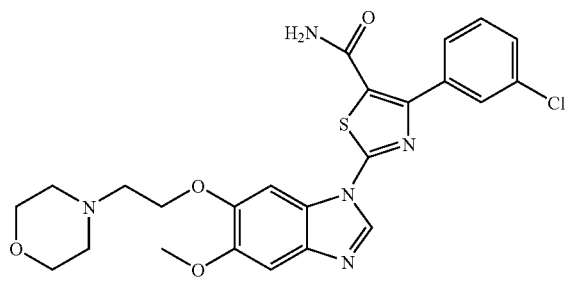

To a mixture of 0.070 g (0.15 mmole) of 4-(3-chloro-phenyl)-2-[6-(2-hydroxy-ethoxy)-5-methoxy-benzoimidazol-1-yl]-thiazole-5-carboxylic acid amide (I.44a), 0.041 g (0.242 mmole) of ethyldiisopropylamine and 3 mL of dimethylformamide 0 degrees was added 0.027 g (0.24 mmole) of methanesulfonyl chloride. Stirring was continued for 1 hour and then 1 mL of saturated ammonium chloride solution was added dropwise. The mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was heated at 80 degrees for 1 hour with 2 mL of dimethylformamide and 0.080 mL of morpholine. The mixture was poured into 25 mL of water and extracted three times with 20 mL of ethyl acetate. The combined organic extracts were washed three times with 25 mL of water, once with 25 mL of saturated sodium bicarbonate solution, once with 25 mL of brine, dried over anhydrous magnesium sulfate, filtered and concentrated under reduced pressure. The residue was purified by silica gel chromatography, eluting with methanol-dichloromethane (6:94) to give 0.017 g of 4-(3-chloro-phenyl)-2-[5-methoxy-6-(2-morpholin-4-yl-ethoxy)-benzoimidazol-1-yl]-thiazole-5-carboxylic acid amide (I.45) as a pink solid. MH+/Z=514

Example 46

4-(3-Chloro-phenyl)-2-[5-methoxy-6-(4-methyl-piperazin-1-ylmethyl)-benzoimidazol-1-yl]-thiazole-5-carboxylic acid amide (I.46)

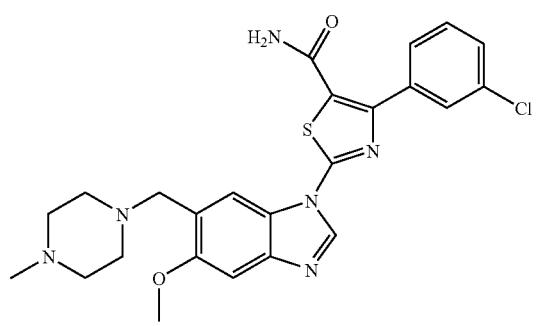

Step 1

To a mixture of 0.500 g (3.57 mmole) of 5-fluoro-2-hydroxy-benzaldehyde, 0.694 g (6.4 mmole) of triethylamine, and 5 mL of dichloromethane at 0 degrees was added dropwise, 0.444 g (3.90 mmole) of methanesulfonyl chloride. Stirring was continued for 15 minutes. The mixture was diluted with 30 mL of dichloromethane and washed with 20 mL of saturated ammonium chloride solution, 20 mL of water, 20 mL of brine, dried over anhydrous sodium sulfate, filtered and concentrated under reduced pressure to give 0.760 g of methanesulfonic acid 4-fluoro-2-formyl-phenyl ester as a yellow oil.

Step 2

To a mixture of 0.760 g (3.49 mmole) of methanesulfonic acid 4-fluoro-2-formyl-phenyl ester and 10 mL of methanol at 0 degrees was added, portionwise over 10 minutes, 0.200 g (5.4 mmole) of sodium borohydride. The mixture was stirred at 0 degrees for 10 minutes and then concentrated under reduced pressure. The residue was partitioned between 50 mL of ethyl acetate and 50 mL of water while 1 M hydrochloric acid was carefully added. The mixture was stirred at room temperature until gas evolution ceased. The aqueous layer was extracted three times with 20 mL of ethyl acetate. The combined organic layers were washed with 30 mL of brine, dried over anhydrous magnesium sulfate, filtered and concentrated under reduced pressure to give 0.740 g of methanesulfonic acid 4-fluoro-2-hydroxymethyl-phenyl ester as a yellow oil.

Step 3

To a mixture of 7.53 g (34 mmole) of methanesulfonic acid 4-fluoro-2-hydroxymethyl-phenyl ester and 60 mL of concentrated sulfuric acid at 0 degrees was added dropwise, a cold mixture of 2.5 mL of concentrated nitric acid and 3 mL of concentrated sulfuric acid. The mixture was poured on ice and extracted three times with 50 mL of ethyl acetate. The combined organic layers were washed with brine, dried over anhydrous magnesium sulfate, filtered and concentrated under reduced pressure. The residue was triturated with diethyl ether to give 3.5 g of methanesulfonic acid 4-fluoro-5-nitro-2-sulfooxymethyl-phenyl ester as a white solid. The white solid was heated to reflux for 1 hour with 100 mL of methanol, 2 mL of trimethylorthoformate and 0.10 g of p-toluenesulfonic acid monohydrate. The mixture was neutralized by addition of saturated sodium bicarbonate solution and then concentrated under reduced pressure. The residue was partitioned between 200 mL of ethyl acetate and 100 mL of saturated sodium bicarbonate solution. The organic layer was dried over anhydrous magnesium sulfate, filtered and concentrated under reduced pressure to give 2.6 g of methanesulfonic acid 4-fluoro-2-hydroxymethyl-5-nitro-phenyl ester as a white solid.

Step 4

A mixture of 2.71 g (10.2 mmole) of methanesulfonic acid 4-fluoro-2-hydroxymethyl-5-nitro-phenyl ester, 12 g of manganese dioxide and dichloromethane was stirred at room temperature for 16 hours. The mixture was filtered through Diatomaceous earth, and the filter cake was washed with tetrahydrofuran. The filtrate was concentrated under reduced pressure. The residue was heated at reflux for 1 hour with 100 mL of methanol and 0.5 g of p-toluene sulfonic acid monohydrate. The mixture was cooled, neutralized with saturated sodium bicarbonate solution and concentrated under reduced pressure. The residue was dissolved in 100 mL of dichloromethane and washed with saturated sodium bicarbonate solution. The dichloromethane layer was concentrated under reduced pressure to give 2.13 g of methanesulfonic acid 2-dimethoxymethyl-4-fluoro-5-nitro-phenyl ester (IV.46a) as a yellow oil.

Step 5

To a mixture of 0.348 g (1.13 mmole) of methanesulfonic acid 2-dimethoxymethyl-4-fluoro-5-nitro-phenyl ester (IV.46a) and 4 mL of dimethylsulfoxide, cooled briefly in an ice bath, was added dropwise a cold solution of 0.10 g of potassium hydroxide in 1 mL of dimethylsulfoxide-water (1:1). The resulting dark red mixture was stirred at room temperature for 15 minutes and then was made acidic by addition of 1 M hydrochloric acid to give a yellow mixture. The mixture was partitioned between 50 mL of ethyl acetate and 50 mL of water. The aqueous layer was extracted three times with 25 mL of ethyl acetate. The combined organic layers were washed three times with 30 mL of water, once with 30 mL of brine, dried over anhydrous magnesium sulfate, filtered and concentrated under reduced pressure to give 0.195 g of 5-fluoro-2-hydroxy-4-nitro-benzaldehyde (IV.46b) as a yellow solid.

Step 6

To a suspension of 0.524 g (3.80 mmole) of potassium carbonate, 0.5 mL of iodomethane and 8 mL of dimethylformamide was added, dropwise, a solution of 0.141 g (0.76 mmole) of 5-fluoro-2-hydroxy-4-nitro-benzaldehyde (IV.46b) in 1 mL of dimethylformamide. The resulting dark red solution was stirred at room temperature for 3 hours. The mixture was poured into 50 mL of water and extracted three times with 25 mL of ethyl acetate. The combined organic layers were washed three times with 25 mL of water, once with 25 mL of brine, dried over anhydrous magnesium sulfate, filtered and concentrated under reduced pressure to give 0.143 g of 5-fluoro-2-methoxy-4-nitro-benzaldehyde (IV.46c) as a yellow solid.

Step 7

A mixture of 0.210 g (1.06 mmole) of 5-fluoro-2-methoxy-4-nitro-benzaldehyde (IV.46c), 1 mL of trimethylorthoformate, 0.025 g of p-toluenesulfonic acid monohydrate and 5 mL of methanol was heated at reflux for one hour. The mixture was cooled, neutralized by addition of saturated sodium bicarbonate solution and concentrated under reduced pressure. The residue was partitioned between ethyl acetate and saturated sodium bicarbonate solution. The organic layer was dried over anhydrous magnesium sulfate, filtered and concentrated under reduced pressure to give 0.243 g of 1-dimethoxymethyl-5-fluoro-2-methoxy-4-nitro-benzene (IV.46d) as a yellow oil.

Step 8

A mixture of 0.240 g (0.98 mmole) of 1-dimethoxymethyl-5-fluoro-2-methoxy-4-nitro-benzene (IV.46d), 0.248 g (0.98 mmole) of 2-amino-4-(3-chloro-phenyl)-thiazole-5-carboxylic acid amide (V.2), 0.956 g (2.94 mmole) of cesium carbonate and 5 mL of dimethylformamide was heated at 60 degrees for 3 hours. The mixture was cooled, poured into dilute ammonium chloride solution, and the precipitated orange solid was collected by filtration, washed with water, and air dried to give 0.286 g of 4-(3-chloro-phenyl)-2-(5-dimethoxymethyl-4-methoxy-2-nitro-phenylamino)-thiazole-5-carboxylic acid amide (VI.46a).

Step 9

A mixture of 0.200 g (0.42 mmole) of 4-(3-chloro-phenyl)-2-(5-dimethoxymethyl-4-methoxy-2-nitro-phenylamino)-thiazole-5-carboxylic acid amide (VI.46a), 6 mL of acetonitrile, 2 mL of 6 M hydrochloric acid heated at reflux for 2 hours. The mixture was diluted with 200 mL of ice-water and the purple precipitate was collected by filtration, washed with water, and air dried to give 0.140 g of 4-(3-chloro-phenyl)-2-(5-formyl-4-methoxy-2-nitro-phenylamino)-thiazole-5-carboxylic acid amide (VI.46b).

Step 10

To a suspension of 0.100 g (0.23 mmole) of 4-(3-chloro-phenyl)-2-(5-formyl-4-methoxy-2-nitro-phenylamino)-thiazole-5-carboxylic acid amide (VI.46b), 3 mL of saturated ammonium chloride solution and 3 mL of tetrahydrofuran was added 0.100 g of zinc powder. The mixture was stirred room temperature until the organic layer became straw yellow in color (1 hour). The mixture was filtered, and the filtrate was partitioned between 30 mL of saturated ammonium chloride solution and 30 mL of tetrahydrofuran. The organic layer was dried over anhydrous magnesium sulfate, filtered and concentrated under reduced pressure to give a red solid. The solid was stirred at room temperature with 5 mL of glacial acetic acid and 0.05 mL of trimethylorthoformate for 1 hour and then concentrated under reduced pressure. The residue was partitioned between 50 mL of ethyl acetate and 50 ml, of potassium carbonate solution. The organic layer was dried over anhydrous magnesium sulfate, filtered and concentrated under reduced pressure to give 0.053 g of 4-(3-chloro-phenyl)-2-(6-formyl-5-methoxy-benzoimidazol-1-yl)-thiazole-5-carboxylic acid amide (I.46a) as a yellow solid.

Step 11

A mixture of 0.053 g (0.13 mmole) of 4-(3-chloro-phenyl)-2-(6-formyl-5-methoxy-benzoimidazol-1-yl)-thiazole-5-carboxylic acid amide (I.46a), 0.030 mL of N-methylpiperazine, 0.050 g of sodium triacetoxyborohydride and 5 mL of dichloromethane was stirred at room temperature for 16 hours. The mixture was partitioned between 50 mL of dilute aqueous potassium carbonate solution and 50 mL of dichloromethane. The organic layer was separated and the aqueous layer was extracted three times with 20 mL of dichloromethane. The combined organic layers were washed with 30 mL of brine, dried over anhydrous sodium sulfate, filtered and concentrated under reduced pressure. The residue was purified by silica gel chromatography, eluting with methanol-dichloromethane (gradient 15:85-20:80) to give 0.016 g of 4-(3-chloro-phenyl)-2-[5-methoxy-6-(4-methyl-piperazin-1-ylmethyl)-benzoimidazol-1-yl]-thiazole-5-carboxylic acid amide (I.46) as a pink solid. MH+/Z=497

Example 47

2-[6-(4-Methyl-piperazin-1-ylmethyl)-benzoimidazol-1-yl]-4-(4-trifluoromethyl-phenyl)-thiazole-5-carboxylic acid amide (I.47)

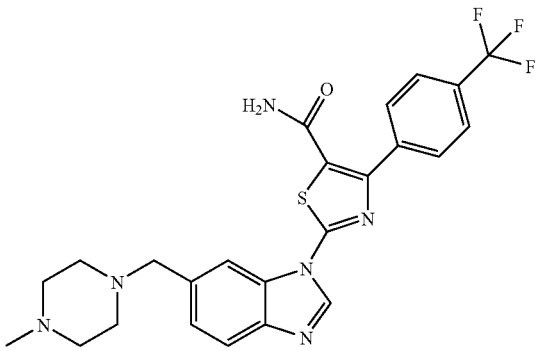

Step 1

A mixture of 0.1171 g (0.40 mmole) of 2-amino-4-(4-trifluoromethyl-phenyl)-thiazole-5-carboxylic acid amide (V.47), 0.0892 g (0.414 mmole) of 4-dimethoxymethyl-2-fluoro-1-nitro-benzene, 6 mL of dimethylformamide and 0.6741 g (2.069 mmole) of cesium carbonate was heated at 60 degrees for 5 hours. The cooled mixture was added to dilute aqueous ammonium chloride. The precipitate was collected by filtration to give 0.1771 g of 2-(5-dimethoxymethyl-2-nitro-phenylamino)-4-(4-trifluoromethyl-phenyl)-thiazole-5-carboxylic acid amide (VI.47a).

Step 2

A mixture of 0.9023 g (1.87 mmole) of 2-(5-dimethoxymethyl-2-nitro-phenylamino)-4-(4-trifluoromethyl-phenyl)-thiazole-5-carboxylic acid amide, 34 mL of acetonitrile and 17 mL of 1M hydrochloric acid was heated at 60 degrees for 2 hours. The cooled mixture was diluted with 50 mL of water. The resulting precipitate was collected by filtration, washed with water and dried to give 0.5766 g of 2-(5-formyl-2-nitro-phenylamino)-4-(4-trifluoromethyl-phenyl)-thiazole-5-carboxylic acid amide (VI.47b) as an orange-red solid.

Step 3

A mixture of 0.1041 g (0.239 mmole) of 2-(5-formyl-2-nitro-phenylamino)-4-(4-trifluoromethyl-phenyl)-thiazole-5-carboxylic acid amide (VI.47b), 5 mL of dichloromethane, 0.0781 g (0.772 mmole) of 1-methyl piperazine and 0.2665 (1.195 mmole) of sodium triacetoxyborohydride was stirred for 15 hours. The mixture was treated with 1 mL of saturated ammonium chloride, followed by 10 mL of saturated sodium bicarbonate and 5 mL of dichloromethane. The mixture was stirred for 45 minutes. The aqueous layer was extracted twice with dichloromethane. The combined organic layers were dried over anhydrous sodium sulfate, filtered, and concentrated under reduced pressure. The residue was purified by silica gel chromatography, eluting with methanol-dichloromethane (gradient 1:99-20:80) to give 0.074 g of 2-[5-(4-methyl-piperazin-1-ylmethyl)-2-nitro-phenylamino]-4-(4-trifluoromethyl-phenyl)thiazole-5-carboxylic acid amide (VI.47c) as a light orange solid.

Step 4

A mixture of 0.072 g (0.138 mmole) of 2-[5-(4-methyl-piperazin-1-ylmethyl)-2-nitro-phenylamino]-4-(4-trifluoromethyl-phenyl)thiazole-5-carboxylic acid amide (VI.47c), 0.0696 g of 10% palladium on carbon catalyst, and 6 mL of 96% formic acid was stirred under one atmosphere of hydrogen for 17 hours. The mixture was filtered through Diatomaceous earth and the filter pad was washed with tetrahydrofuran. The filtrate was concentrated under reduced pressure. The residue was purified by reverse phase silica gel chromatography, eluting with acetonitrile-water-trifluoroacetic acid (gradient 10:90:0.1-60:40:0.1) to give 2-[6-(4-methyl-piperazin-1-ylmethyl)-benzoimidazol-1-yl]-4-(4-trifluoromethyl-phenyl)thiazole-5-carboxylic acid amide trifluoroacetic acid salt (I.47a). This salt was partitioned between 10 mL of saturated sodium carbonate solution and 150 mL of ethyl acetate. The organic layer was washed with 15 mL of water, then 15 mL of brine, dried over anhydrous sodium sulfate, filtered and concentrated under reduced pressure to give 0.0401 g of 2-[6-(4-methyl-piperazin-1-ylmethyl)-benzoimidazol-1-yl]-4-(4-trifluoromethyl-phenyl)thiazole-5-carboxylic acid amide (I.47) as a white solid. MH+/Z=501.

Example 48

2-[6-(4-Methyl-piperazin-1-ylmethyl)-benzoimidazol-1-yl]-4-(3-trifluoromethyl-phenyl)-thiazole-5-carboxylic acid amide (I.48)

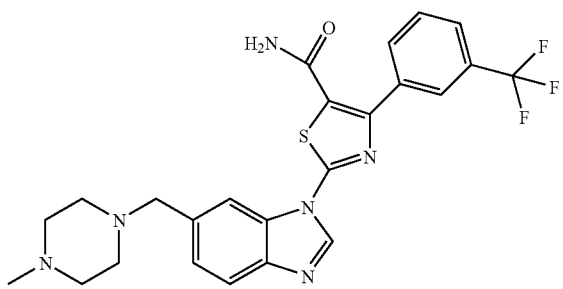

Step 1

A mixture of 0.5691 g (1.981 mmole) of 2-amino-4-(3-trifluoromethyl-phenyl)-thiazole-5-carboxylic acid amide (V.48), 0.4515 g (2.098 mmole) of 4-dimethoxymethyl-2-fluoro-1-nitro-benzene 29 mL of dimethylformamide and 3.2215 g (9.877 mmole) of cesium carbonate was heated at 56 degrees for 4 hours. The cooled mixture was poured into dilute aqueous ammonium chloride solution. The precipitate was collected by filtration, washed with water, and dried to give 0.8344 g of 2-(5-dimethoxymethyl-2-nitro-phenylamino)-4-(3-trifluoromethyl-phenyl)-thiazole-5-carboxylic acid amide (VI.48a) as a brown-orange solid.

Step 2

A mixture of 0.4154 g (0.861 mmole) of 2-(5-dimethoxymethyl-2-nitro-phenylamino)-4-(3-trifluoromethyl-phenyl)-thiazole-5-carboxylic acid amide, 16 mL of acetonitrile and 8 mL of 1M hydrochloric acid was heated at 60 degrees for 1.5 hours. The cooled mixture diluted with 50 mL of water. The precipitate was collected by filtration, washed with water and dried to give 0.3198 g of 2-(5-formyl-2-nitro-phenylamino)-4-(3-trifluoromethyl-phenyl)-thiazole-5-carboxylic acid amide (VI.48b) as an orange solid.

Step 3

A mixture of 0.1289 g (0.295 mmole) of 2-(5-formyl-2-nitro-phenylamino)-4-(3-trifluoromethyl-phenyl)-thiazole-5-carboxylic acid amide (VI.48b), 6.5 mL of dichloromethane, 0.1 mL (0.892 mmole) of 1-methyl piperazine and 0.3321 g (1.489 mmole) of sodium triacetoxyborohydride was stirred for 16 hours. The mixture was quenched by the addition of 1 mL of saturated ammonium chloride, 1 mL of water and 5 mL of dichloromethane, followed by the addition of 10 mL of saturated sodium bicarbonate solution and 20 mL of dichloromethane. The mixture was stirred for 45 minutes and then diluted with 75 mL of dichloromethane and 5 mL of water. The aqueous layer was extracted twice with dichloromethane. The combined dichloromethane layers were dried over anhydrous sodium sulfate, filtered, and concentrated under reduced pressure. The residue was purified by silica gel chromatography, eluting with methanol-dichloromethane (gradient 1:99-20:80) to give 0.127 g of 2-[5-(4-methyl-piperazin-1-ylmethyl)-2-nitro-phenylamino]-4-(3-trifluoromethylphenyl)-thiazole-5-carboxylic acid amide (VI.48c) as a yellow-orange solid.

Step 4

A mixture of 0.1244 g (0.239 mmole) of 2-[5-(4-methyl-piperazin-1-ylmethyl)-2-nitro-phenylamino]-4-(3-trifluoromethylphenyl)-thiazole-5-carboxylic acid amide (VI.48c), 0.1186 g of 10% palladium on carbon catalyst and 10.4 mL of 96% formic acid was stirred under one atmosphere of hydrogen for 16 hours. The mixture was filtered through diatomaceous earth and the filter pad was washed with tetrahydrofuran. The filtrate was concentrated under reduced pressure. The residue was purified by reverse phase silica gel chromatography, eluting with acetonitrile-water-trifluoroacetic acid (gradient 10:90:0.1-60:40:0.1) to give 0.0693 g of 2-[6-(4-methyl-piperazin-1-ylmethyl)-benzoimidazol-1-yl]-4-(3-trifluoromethyl-phenyl)thiazole-5-carboxylic acid amide trifluoroacetic acid salt (I.48a). This salt was partitioned between 10 mL of saturated sodium carbonate solution and 150 mL of ethyl acetate. The organic layer was washed with 15 mL of water, then 15 mL of brine, dried over anhydrous sodium sulfate, filtered and concentrated under reduced pressure to give 0.0693 g of 2-[6-(4-methyl-piperazin-1-ylmethyl)-benzoimidazol-1-yl]-4-(3-trifluoromethyl-phenyl)thiazole-5-carboxylic acid amide (I.48) as a white solid. MH+/Z=501.

Example 49

2-(6-{[Bis-(3-morpholin-4-yl-propyl)-amino]-methyl}-benzoimidazol-1-yl)-4-(3-chloro-phenyl)-thiazole-5-carboxylic acid amide (I.49)

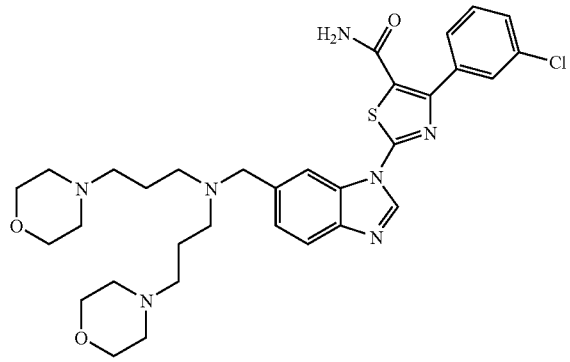

Step 1

A mixture of 0.455 g (1.13 mmole) of 4-(3-chloro-phenyl)-2-(5-formyl-2-nitro-phenylamino)-thiazole-5-carboxylic acid amide (VI.2b), 0.860 g (2.26 mmole) of bis-(3-morpholin-4-yl-propyl)-amine trihydrochloride and 50 mL of dichloromethane was stirred for 20 minutes, then 0.479 g 2.26 mmole) of sodium triacetoxy borohydride was added. The mixture was stirred for 4 days, then quenched by the addition of 50 mL of saturated sodium bicarbonate solution. The mixture was extracted three times with 50 mL of dichloromethane. The combined dichloromethane layers were washed with 50 mL of brine, dried over anhydrous sodium sulfate, filtered and concentrated under reduced pressure. The residue was purified by silica gel chromatography, eluting with dichloromethane-methanol (90:10) to give 0.210 g of 2-(5-{[bis-(3-morpholin-4-yl-propyl)-amino]-methyl}-2-nitro-phenylamino)-4-(3-chloro-phenyl)-thiazole-5-carboxylic acid amide (VI.49a).

Step 2

To a mixture of 0.150 g (0.23 mmole) of 2-(5-{[bis-(3-morpholin-4-yl-propyl)-amino]-methyl}-2-nitro-phenylamino)-4-(3-chloro-phenyl)-thiazole-5-carboxylic acid amide (VI.49a), 20 mL of tetrahydrofuran, and 20 mL of saturated ammonium chloride solution was added 0.089 g (1.38 mg-atom) of zinc powder. After 5 minutes the mixture was filtered and the filtrate partitioned between 50 mL of saturated ammonium chloride and 50 mL of tetrahydrofuran. The tetrahydrofuran layer was dried over anhydrous sodium sulfate, filtered and concentrated under reduced pressure. The residue was stirred for 3 hours with 30 mL of acetic acid and 0.178 g (1.2 mmole) of triethyl orthoformate. The mixture was concentrated under reduced pressure, diluted with 100 mL of dichloromethane and washed with saturated sodium bicarbonate solution, then brine, dried over anhydrous sodium sulfate and concentrated under reduced pressure. The residue was purified by silica gel chromatography, eluting with dichloromethane-methanol-ammonium hydroxide (92:8:1) to give 0.075 g of 2-(6-{[bis-(3-morpholin-4-yl-propyl)-amino]-methyl}-benzoimidazol-1-yl)-4-(3-chloro-phenyl)-thiazole-5-carboxylic acid amide (I.49) as a light pink solid. MH+/Z=638.

Example 50

4-(3-Chloro-phenyl)-2-(6-{[methyl-(3-morpholin-4-yl-propyl)-amino]-methyl}-benzoimidazol-1-yl)-thiazole-5-carboxylic acid amide (I.50)

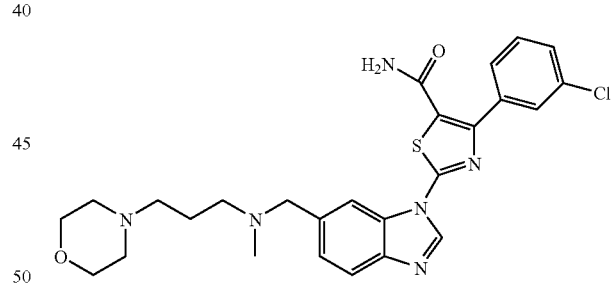

Step 1

A mixture of 0.900 g (2.23 mmole) of 4-(3-chloro-phenyl)-2-(5-formyl-2-nitro-phenylamino)-thiazole-5-carboxylic acid amide (VI.2b), 1.03 g (4.46 mmole) of methyl-(3-morpholin-4-yl-propyl)-amine dihydrochloride and 60 mL of dichloromethane was stirred for 20 minutes, then 1.134 g (5.35 mmole) of sodium triacetoxyborohydride was added. The mixture was stirred for 4 days, then quenched by the addition of 50 mL of saturated sodium bicarbonate solution. The mixture was extracted three times with 50 mL of dichloromethane. The combined dichloromethane layers were washed with 50 mL of brine, dried over anhydrous sodium sulfate, filtered and concentrated under reduced pressure. The residue was purified by silica gel chromatography, eluting with dichloromethane-methanol (90:10) to give 0.830 g of 4-(3-chloro-phenyl)-2-(5-{[methyl-(3-morpholin-4-yl-propyl)-amino]-methyl}-2-nitro-phenylamino)-thiazole-5-carboxylic acid amide (VI.50a).

Step 2

To a mixture of 0.150 g (0.28 mmole) of 4-(3-chloro-phenyl)-2-(5-{[methyl-(3-morpholin-4-yl-propyl)-amino]-methyl}-2-nitro-phenylamino)-thiazole-5-carboxylic acid amide (VI.50a), 20 mL of tetrahydrofuran, and 20 mL of saturated ammonium chloride solution was added 0.089 g (1.38 mg-atom) of zinc powder. After 5 minutes the mixture was filtered and the filtrate partitioned between 50 mL of saturated ammonium chloride and 50 mL of tetrahydrofuran. The tetrahydrofuran layer was dried over anhydrous sodium sulfate, filtered and concentrated under reduced pressure. The residue was stirred for 3 hours with 30 mL of acetic acid and 0.178 g (1.2 mmole) of triethyl orthoformate. The mixture was concentrated under reduced pressure, diluted with 100 mL of dichloromethane and washed with saturated sodium bicarbonate solution, then brine, dried over anhydrous sodium sulfate and concentrated under reduced pressure. The residue was purified by silica gel chromatography, eluting with dichloromethane-methanol-ammonium:hydroxide (92:8:1) to give 0.075 g of 4-(3-chloro-phenyl)-2-(6-{[methyl-(3-morpholin-4-yl-propyl)-amino]-methyl}-benzoimidazol-1-yl)-thiazole-5-carboxylic acid amide (I.50) as a light pink solid. MH+/Z=525.

Biochemical Characterization Assay A

Full-length, active GST-Plk1 was purified from Sf9 insect cells, and full-length GST-p53 was purified in *E. coli*. Anti-phospho p53 antibody was purchased from Cell Signaling Technology. Europium-conjugated anti-rabbit antibody was purchased from PerkinElmer Life and Analytical Sciences. APC-conjugated anti-GST antibody was purchased from Prozyme.

To two microliters of compound (0.6 nM-4 mM) in DMSO or plain DMSO for control wells, 38 microliters of 20 mM HEPES pH 7, 50 mM NaCl, 10 mM $MgCl_2$, 0.5 mM TCEP, 0.1 mM sodium orthovanadate, 0.1 mg/ml BSA, and 0.05% Triton X-100 (Kinase Assay Buffer) were added. Eight microliters of the compound solution were added to a 384-well black microtiter plate, followed by six microliters of GST-p53 (17 ug/ml) and ATP (333 uM) in Kinase Assay Buffer. Six microliters of GST-Plk1 (3 ug/ml) in Kinase Assay Buffer were then added and the solution incubated at 37° C. for 35 minutes. Six microliters of solution containing 43 mM EDTA to stop the reaction and a 1:600 dilution of anti-phospho-p53 antibody in 20 mM HEPES pH 7, 50 mM NaCl, and 0.5 mg/ml BSA (Antibody Binding Buffer) were added and the solution incubated at 37° C. for 30 minutes. Six microliters of solution containing 9 nM europium-conjugated anti-rabbit antibody and 120 nM APC-conjugated anti-GST antibody in Antibody Binding Buffer were then added and the mixture incubated at room temperature for 1.5 hours. The HTRF signal was read on the Envision reader (PerkinElmer Life and Analytical Sciences).

Biochemical Characterization Assay B

Compounds were serially diluted to 6400, 2133, 711, 237, 79, 26, 8.78, 2.93, 0.98 and 0.33 µM in 100% DMSO. Diluted compound was further diluted 20 fold with Kinase Assay Buffer (KAB). Peptide RRRAGALMDASFEEQ-CONH2 (MW 2090) was diluted to 1.2 µM with KAB and ATP was added to 400 µM. PLK1 stock, prepared as described above, was diluted to 3 µg protein/mL with KAB right before it was added to MATRIX 384-Well Polypropylene Black Plates to start the reaction. 20 µL of KAB diluted compounds (or 5% DMSO in KAB for Total and Blank), 20 µL of KAB diluted peptide with ATP and 40 µL of KAB diluted PLK1 solution (KAB without PLK 1 for Blanks) were transferred to each well of the polypropylene plates. The reaction mixtures were incubated at room temperature for 40 minutes. Reactions were stopped by addition of 10 uL Reaction Stopping Buffer (RSB) to each well. Plates were then read on LABCHIP EZ Reader II from Caliper Life Science.

Calculation of IC50

The IC50 values for each compound were generated using an Excel template. The % conversion readings of Total and Blank were used as 0% and 100% inhibition. The percent inhibition values of reactions in the presence of compounds were calculated, and plotted against compound concentrations. All data were fitted into a Dose Response One Site model (4 parameter logistic model) as the following: (A+4B−A)/(1+((x/C)^13)))), with A and B as the bottom and top of the curve (highest and lowest inhibition), respectively, and C as IC50 and D as Hill Coefficient of the compound.

TABLE 1

RESULTS FROM BIOCHEMICAL ASSAYS

| example | R1 | R2 | A | assay A $IC_{50}$ uM | assay B $IC_{50}$ uM |
|---|---|---|---|---|---|
| 1 | H | (piperazine-ethyl structure) | phenyl | 0.167 | |
| 2 | H | (piperazine-ethyl structure) | 3-Cl | 0.013 | |
| 3 | (piperazine-ethyl structure) | H | 3-Cl | 1.103 | |

TABLE 1-continued
RESULTS FROM BIOCHEMICAL ASSAYS
| example | R1 | R2 | A | assay A IC$_{50}$ uM | assay B IC$_{50}$ uM |
|---|---|---|---|---|---|
| 4 | H | 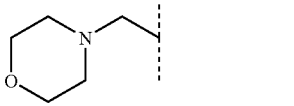 | 3-Cl | 0.306 | |
| 5 | H | 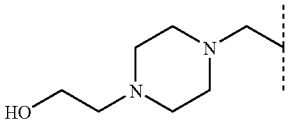 | 3-Cl | 0.091 | |
| 6 | H | 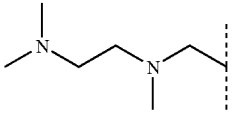 | 3-Cl | | 0.50 |
| 7 | H | 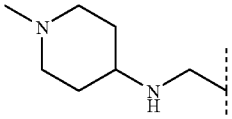 | 3-Cl | 0.443 | |
| 8 | H | 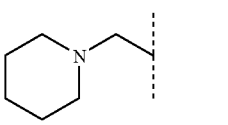 | 3-Cl | 3.444 | |
| 9 | H | 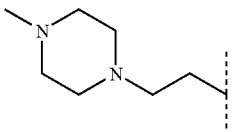 | 3-Cl | 0.109 | |
| 10 | H | 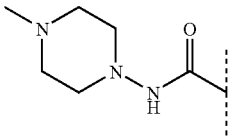 | 3-Cl | 2.019 | |
| 11 | H | 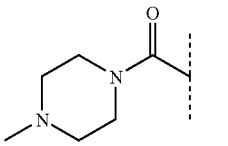 | 3-Cl | 0.215 | |
| 12 | H | 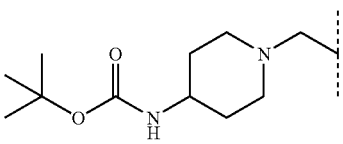 | 3-Cl | | 0.666 |
| 13 | H | 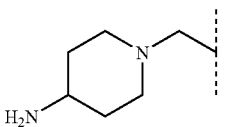 | 3-Cl | | 0.037 |

TABLE 1-continued

RESULTS FROM BIOCHEMICAL ASSAYS

| example | R1 | R2 | A | assay A IC$_{50}$ uM | assay B IC$_{50}$ uM |
|---|---|---|---|---|---|
| 14 | H | (1-methylpiperidine-4-carboxamide linked to piperidin-4-yl via N-H, N-ethyl) | 3-Cl | | 1.482 |
| 15 | H | (tert-butyl (2-methyl-1-oxo-1-((1-ethylpiperidin-4-yl)amino)propan-2-yl)carbamate) | 3-Cl | | 5.272 |
| 16 | H | (2-amino-2-methyl-N-(1-ethylpiperidin-4-yl)propanamide) | 3-Cl | | 1.290 |
| 17 | H | (4-methylpiperazin-1-yl ethyl) | 2-CF$_3$ | 1.138 | |
| 18 | (4-methylpiperazin-1-yl ethyl) | H | 4-Cl | >80 | |
| 19 | H | (4-methylpiperazin-1-yl ethyl) | 4-Cl | 0.499 | |
| 20 | H | (4-methylpiperazin-1-yl ethyl) | 2-Cl | 0.346 | |
| 21 | H | (piperidin-4-yloxy) | 3-Cl | 0.080 | |
| 22 | H | (1-methylpiperidin-4-yloxy) | 3-Cl | 0.018 | |
| 23 | H | (piperidin-4-yl)methoxy | 3-Cl | 0.017 | |

TABLE 1-continued
RESULTS FROM BIOCHEMICAL ASSAYS
| example | R1 | R2 | A | assay A IC$_{50}$ uM | assay B IC$_{50}$ uM |
|---|---|---|---|---|---|
| 24 | H | 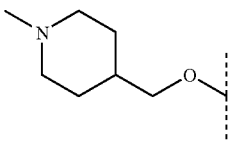 | 3-Cl | | 0.014 |
| 25 | H | 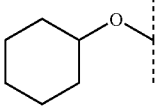 | 3-Cl | 0.660 | |
| 26 | H | 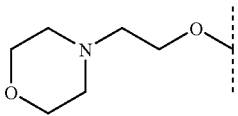 | 3-Cl | 0.166 | |
| 27 | H | 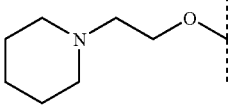 | 3-Cl | | 0.264 |
| 28 | H | 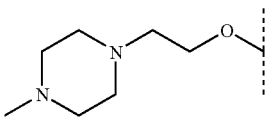 | 3-Cl | | 0.105 |
| 29 | H | 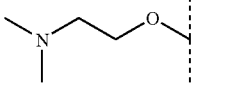 | 3-Cl | | 0.356 |
| 30 | H | 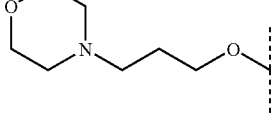 | 3-Cl | 0.021 | |
| 31 | H | 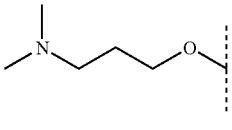 | 3-Cl | 0.161 | |
| 32 | H | 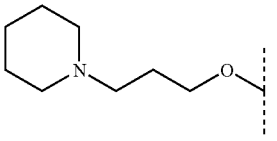 | 3-Cl | | 0.080 |
| 33 | H | 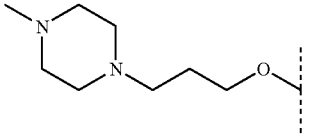 | 3-Cl | 0.032 | |
| 34 | H | 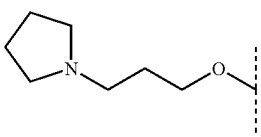 | 3-Cl | | 0.050 |

TABLE 1-continued
RESULTS FROM BIOCHEMICAL ASSAYS
| example | R1 | R2 | A | assay A IC$_{50}$ uM | assay B IC$_{50}$ uM |
|---|---|---|---|---|---|
| 35 | H | 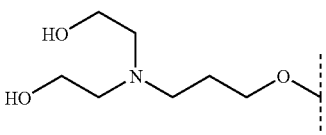 | 3-Cl | | 0.068 |
| 36 | H | 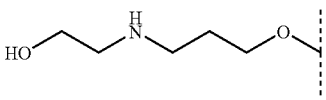 | 3-Cl | | 0.080 |
| 37 | H | 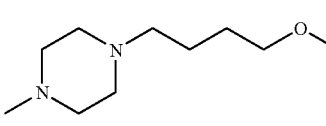 | 3-Cl | | 0.027 |
| 38 | H | 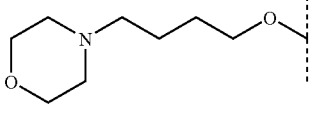 | 3-Cl | | 0.011 |
| 39 | H | 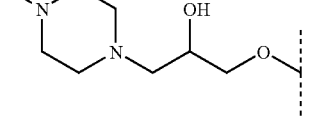 | 3-Cl | | 0.050 |
| 40 | H | 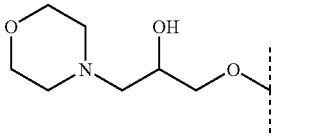 | 3-Cl | | 0.013 |
| 41 | H | 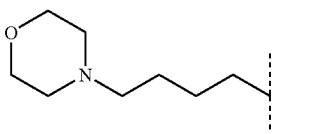 | 3-Cl | | 0.016 |
| 42 | CH$_3$O | 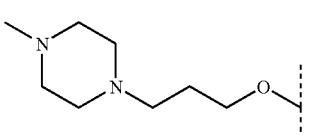 | 3-Cl | 0.019 | 0.06 |
| 43 | CH$_3$O | 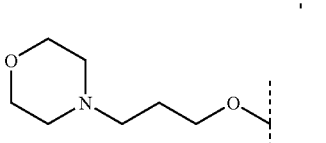 | 3-Cl | | 0.008 |
| 44 | CH$_3$O | 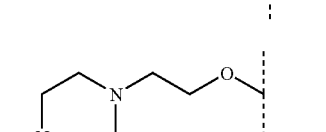 | 3-Cl | | 0.061 |
| 45 | CH$_3$O | 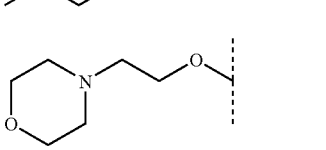 | 3-Cl | | 0.026 |

TABLE 1-continued

RESULTS FROM BIOCHEMICAL ASSAYS

| example | R1 | R2 | A | assay A IC$_{50}$ uM | assay B IC$_{50}$ uM |
|---|---|---|---|---|---|
| 46 | CH$_3$O | (N-methylpiperazinyl-ethyl) | 3-Cl | | 0.013 |
| 47 | H | (N-methylpiperazinyl-ethyl) | 4-CF$_3$ | | 0.661 |
| 48 | H | (N-methylpiperazinyl-ethyl) | 3-CF$_3$ | | 0.059 |
| 49 | H | (bis-morpholinopropyl-amine) | 3-Cl | | 0.566 |
| 50 | H | (morpholinopropyl-methylamino-ethyl) | 3-Cl | | 0.085 |

For A, 2-Cl means 2-chlorophenyl; 3-Cl means 3-chlorophenyl; 4-Cl means 4-chlorophenyl; 2-CF$_3$ means 2-trifluoromethylphenyl; 3-CF$_3$ means 3-trifluoromethylphenyl; 4-CF$_3$ means 4-trifluoromethylphenyl

What is claimed is:
1. A compound of formula (I)

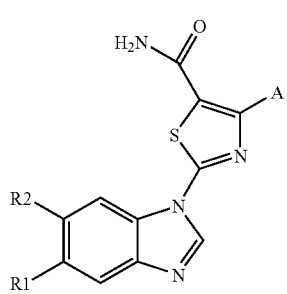

(I)

wherein
A is selected from the group consisting of phenyl, 2-chlorophenyl, 3-chlorophenyl, 4-chlorophenyl, 2-trifluoromethylphenyl, 3-trifluoromethylphenyl, and 4-trifluoromethylphenyl;
R$_1$ is selected from the group consisting of H, and OCH$_3$;
R$_2$ is Z-Q-R$_3$, wherein Z is selected from the group consisting of nothing, O, and C(O)

Q is selected from the group consisting of (CH$_2$)$_m$ and CH$_2$CH(OH)CH$_2$ and m is an integer from 0 to 4;

R$_3$ is selected from the group consisting of

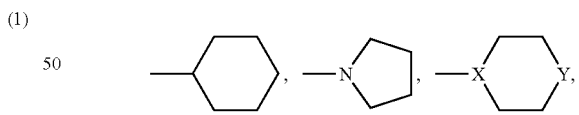

and —NR$_4$, R$_5$;

R$_4$ and R$_5$ are independently selected from the group consisting of H, CH$_3$, (CH$_2$)$_2$OH, (CH$_2$)$_2$,

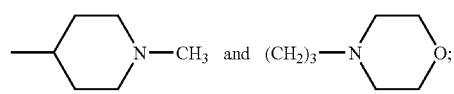

X is selected from the group consisting of CH and N;
Y is selected from the group consisting of O, CHR$_6$, and NR$_7$, wherein

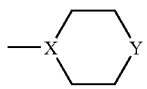

must contain at least one nitrogen atom;
$R_6$ is selected from the group consisting of H, $NH_2$ and $NHC(O)R_8$;
$R_7$ is selected from the group consisting of H, $CH_3$, and $(CH_2)_2OH$;
$R_8$ is selected from the group consisting of OtBu, $OC(CH_3)_2NH_2$, $OC(CH_3)_2NHC(O)OtBu$,
and

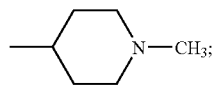

pharmaceutically acceptable salts thereof.

2. A compound of claim 1 wherein
A is 3-chlorophenyl;
$R_2$ is O—$(CH_2)_m$—$R_3$;
$R_3$ is

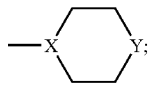

and
Y is $NR_7$.

3. A compound of claim 1 wherein
A is 3-chlorophenyl;
and
$R_2$ is —$(CH_2)_m$—$R_3$.

4. A compound of claim 3 wherein m is 1 and $R_3$ is selected from the group consisting of

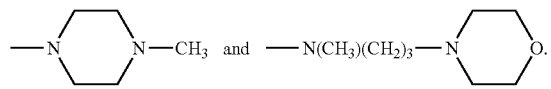

5. A compound of claim 3 wherein $R_3$ is

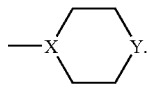

6. A compound of claim 5 wherein X is CH.
7. Compound of claim 5 wherein Y is $CHR_6$.
8. A compound of claim 5 wherein $R_3$ is

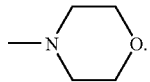

9. A compound of claim 5 wherein $R_3$ is

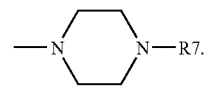

10. A compound of claim 9 wherein $R_7$ is $CH_3$.
11. A compound of claim 3 wherein $R_3$ is $NR_4R_5$.
12. A compound of claim 11 wherein $R_4$ and $R_5$ are both —$CH_2CH_2OH$.
13. A compound of claim 11 wherein $R_4$ is H and $R_5$ is —$CH_2CH_2OH$.
14. A compound of claim 1 selected from the group consisting of:
2-[6-(4-Methyl-piperazin-1-ylmethyl)-benzoimidazol-1-yl]-4-phenyl-thiazole-5-carboxylic acid amide;
4-(3-Chloro-phenyl)-2-[6-(4-methyl-piperazin-1-ylmethyl)-benzoimidazol-1-yl]-thiazole-5-carboxylic acid amide;
4-(3-Chloro-phenyl)-2-(6-morpholin-4-ylmethyl-benzoimidazol-1-yl)-thiazole-5-carboxylic acid amide;
4-(3-Chloro-phenyl)-2-{6-[4-(2-hydroxy-ethyl)-piperazin-1-ylmethyl]-benzoimidazol-1-yl}-thiazole-5-carboxylic acid amide;
4-(3-Chloro-phenyl)-2-(6-{[(2-dimethylamino-ethyl)-methyl-amino]-methyl}-benzoimidazol-1-yl)-thiazole-5-carboxylic acid amide;
4-(3-Chloro-phenyl)-2-{6-[(1-methyl-piperidin-4-ylamino)-methyl]-benzoimidazol-1-yl}-thiazole-5-carboxylic acid amide;
4-(3-Chloro-phenyl)-2-(6-piperidin-1-ylmethyl-benzoimidazol-1-yl)-thiazole-5-carboxylic acid amide;
4-(3-Chloro-phenyl)-2-{6-[2-(4-methyl-piperazin-1-yl)-ethyl]-benzoimidazol-1-yl}-thiazole-5-carboxylic acid amide;
3-[5-Carbamoyl-4-(3-chloro-phenyl)-thiazol-2-yl]-3H-benzoimidazole-5-carboxylic acid (1-methyl-piperidin-4-yl)-amide;
4-(3-Chloro-phenyl)-2-[6-(4-methyl-piperazine-1-carbonyl)-benzoimidazol-1-yl]-thiazole-5-carboxylic acid amide;
1-{3-[5-Carbamoyl-4-(3-chloro-phenyl)-thiazol-2-yl]-3H-benzoimidazol-5-ylmethyl}-piperidin-4-yl)-carbamic acid tert-butyl ester;
2-[6-(4-Amino-piperidin-1-ylmethyl)-benzoimidazol-1-yl]-4-(3-chloro-phenyl)-thiazole-5-carboxylic acid amide;
1-Methyl-piperidine-4-carboxylic acid (1-{3-[5-carbamoyl-4-(3-chloro-phenyl)-thiazol-2-yl]-3H-benzoimidazol-5-ylmethyl}-piperidin-4-yl)-amide;
[1-(1-{3-[5-Carbamoyl-4-(3-chloro-phenyl)-thiazol-2-yl]-3H-benzoimidazol-5-ylmethyl}-piperidin-4-ylcarbamoyl)-1-methyl-ethyl]-carbamic acid tert-butyl ester;
2-{6-[4-(2-Amino-2-methyl-propionylamino)-piperidin-1-ylmethyl]-benzoimidazol-1-yl}-4-(3-chloro-phenyl)-thiazole-5-carboxylic acid amide;
2-[6-(4-Methyl-piperazin-1-ylmethyl)-benzoimidazol-1-yl]-4-(2-trifluoromethyl-phenyl)-thiazole-5-carboxylic acid amide;
4-(4-Chloro-phenyl)-2-[6-(4-methyl-piperazin-1-ylmethyl)-benzoimidazol-1-yl]-thiazole-5-carboxylic acid amide;
4-(2-Chloro-phenyl)-2-[6-(4-methyl-piperazin-1-ylmethyl)-benzoimidazol-1-yl]-thiazole-5-carboxylic acid amide;
4-(3-Chloro-phenyl)-2-[6-(piperidin-4-yloxy)-benzoimidazol-1-yl]-thiazole-5-carboxylic acid amide;

4-(3-Chloro-phenyl)-2-[6-(1-methyl-piperidin-4-yloxy)-benzoimidazol-1-yl]-thiazole-5-carboxylic acid amide;

4-(3-Chloro-phenyl)-2-[6-(piperidin-4-ylmethoxy)-benzoimidazol-1-yl]-thiazole-5-carboxylic acid amide;

4-(3-Chloro-phenyl)-2-[6-(1-methyl-piperidin-4-ylmethoxy)-benzoimidazol-1-yl]-thiazole-5-carboxylic acid amide;

4-(3-Chloro-phenyl)-2-(6-cyclohexyloxy-benzoimidazol-1-yl)-thiazole-5-carboxylic acid amide;

4-(3-Chloro-phenyl)-2-[6-(2-morpholin-4-yl-ethoxy)-benzoimidazol-1-yl]-thiazole-5-carboxylic acid amide;

4-(3-Chloro-phenyl)-2-[6-(2-piperidin-1-yl-ethoxy)-benzoimidazol-1-yl]-thiazole-5-carboxylic acid amide;

4-(3-Chloro-phenyl)-2-{6-[2-(4-methyl-piperazin-1-yl)-ethoxy]-benzoimidazol-1-yl}-thiazole-5-carboxylic acid amide;

4-(3-Chloro-phenyl)-2-[6-(2-dimethylamino-ethoxy)-benzoimidazol-1-yl]-thiazole-5-carboxylic acid amide;

4-(3-Chloro-phenyl)-2-[6-(3-morpholin-4-yl-propoxy)-benzoimidazol-1-yl]-thiazole-5-carboxylic acid amide;

4-(3-Chloro-phenyl)-2-[6-(3-dimethylamino-propoxy)-benzoimidazol-1-yl]-thiazole-5-carboxylic acid amide;

4-(3-Chloro-phenyl)-2-[6-(3-piperidin-1-yl-propoxy)-benzoimidazol-1-yl]-thiazole-5-carboxylic acid amide;

4-(3-Chloro-phenyl)-2-{6-[3-(4-methyl-piperazin-1-yl)-propoxy]-benzoimidazol-1-yl}-thiazole-5-carboxylic acid amide;

4-(3-Chloro-phenyl)-2-[6-(3-pyrrolidin-1-yl-propoxy)-benzoimidazol-1-yl]-thiazole-5-carboxylic acid amide;

2-(6-{3-[Bis-(2-hydroxy-ethyl)-amino]-propoxy}-benzoimidazol-1-yl)-4-(3-chloro-phenyl)-thiazole-5-carboxylic acid amide;

4-(3-Chloro-phenyl)-2-{6-[3-(2-hydroxy-ethylamino)-propoxy]-benzoimidazol-1-yl}-thiazole-5-carboxylic acid amide;

4-(3-Chloro-phenyl)-2-{6-[4-(4-methyl-piperazin-1-yl)-butoxy]-benzoimidazol-1-yl}-thiazole-5-carboxylic acid amide;

4-(3-Chloro-phenyl)-2-[6-(4-morpholin-4-yl-butoxy)-benzoimidazol-1-yl]-thiazole-5-carboxylic acid amide;

4-(3-Chloro-phenyl)-2-{6-[2-hydroxy-3-(4-methyl-piperazin-1-yl)-propoxy]-benzoimidazol-1-yl}-thiazole-5-carboxylic acid amide;

4-(3-Chloro-phenyl)-2-[6-(2-hydroxy-3-morpholin-4-yl-propoxy)-benzoimidazol-1-yl]-thiazole-5-carboxylic acid amide;

4-(3-Chloro-phenyl)-2-[6-(4-morpholin-4-yl-butyl)-benzoimidazol-1-yl]-thiazole-5-carboxylic acid amide;

4-(3-Chloro-phenyl)-2-{5-methoxy-6-[3-(4-methyl-piperazin-1-yl)-propoxy]-benzoimidazol-1-yl}-thiazole-5-carboxylic acid amide;

4-(3-Chloro-phenyl)-2-[5-methoxy-6-(3-morpholin-4-yl-propoxy)-benzoimidazol-1-yl]-thiazole-5-carboxylic acid amide;

4-(3-Chloro-phenyl)-2-{5-methoxy-6-[2-(4-methyl-piperazin-1-yl)-ethoxy]-benzoimidazol-1-yl}-thiazole-5-carboxylic acid amide;

4-(3-Chloro-phenyl)-2-[5-methoxy-6-(2-morpholin-4-yl-ethoxy)-benzoimidazol-1-yl]-thiazole-5-carboxylic acid amide;

4-(3-Chloro-phenyl)-2-[5-methoxy-6-(4-methyl-piperazin-1-ylmethyl)-benzoimidazol-1-yl]-thiazole-5-carboxylic acid amide;

2-[6-(4-Methyl-piperazin-1-ylmethyl)-benzoimidazol-1-yl]-4-(4-trifluoromethyl-phenyl)-thiazole-5-carboxylic acid amide;

2-[6-(4-Methyl-piperazin-1-ylmethyl)-benzoimidazol-1-yl]-4-(3-trifluoromethyl-phenyl)-thiazole-5-carboxylic acid amide;

2-(6-{[Bis-(3-morpholin-4-yl-propyl)-amino]-methyl}-benzoimidazol-1-yl)-4-(3-chloro-phenyl)-thiazole-5-carboxylic acid amide; and 4-(3-Chloro-phenyl)-2-(6-{[methyl-(3-morpholin-4-yl-propyl)-amino]-methyl}-benzoimidazol-1-yl)-thiazole-5-carboxylic acid amide.

15. A composition comprising a compound of claim 1 and one or more members selected from the group consisting of pharmaceutically acceptable carriers and adjuvants.

* * * * *

UNITED STATES PATENT AND TRADEMARK OFFICE
CERTIFICATE OF CORRECTION

| | | |
|---|---|---|
| PATENT NO. | : 8,044,213 B2 | Page 1 of 1 |
| APPLICATION NO. | : 12/634771 | |
| DATED | : October 25, 2011 | |
| INVENTOR(S) | : Cai et al. | |

It is certified that error appears in the above-identified patent and that said Letters Patent is hereby corrected as shown below:

Claim 1, column 84, line 57, delete "sisting of H, CH3, (CH2)2OH,(CH2)2,"
and insert -- sisting of H, CH3, (CH2)2OH, (CH2)2N(CH3)2, --

Claim 1, column 85, line 24, insert -- and -- before pharmaceutically acceptable Claim 7, column 85, line 59, delete "7. Compound" and insert -- 7. A compound --

Signed and Sealed this
Twentieth Day of December, 2011

David J. Kappos
*Director of the United States Patent and Trademark Office*